(12) United States Patent  
Citron et al.

(10) Patent No.: US 8,315,700 B2  
(45) Date of Patent: Nov. 20, 2012

(54) PREVENTING BIOFILM FORMATION ON IMPLANTABLE MEDICAL DEVICES

(75) Inventors: Mark Citron, Montclair, NJ (US); William McJames, Hillsborough, NJ (US)

(73) Assignee: TYRX, Inc., Monmouth Junction, NJ (US)

( * ) Notice: Subject to any disclaimer, the term of this patent is extended or adjusted under 35 U.S.C. 154(b) by 124 days.

(21) Appl. No.: 12/648,126

(22) Filed: Dec. 28, 2009

(65) Prior Publication Data

US 2010/0168808 A1 Jul. 1, 2010

Related U.S. Application Data

(63) Continuation-in-part of application No. 11/936,054, filed on Nov. 6, 2007, which is a continuation-in-part of application No. 11/672,929, filed on Feb. 8, 2007.

(60) Provisional application No. 61/140,918, filed on Dec. 26, 2008, provisional application No. 60/864,597, filed on Nov. 6, 2006, provisional application No. 60/984,254, filed on Oct. 31, 2007, provisional application No. 60/771,827, filed on Feb. 8, 2006.

(51) Int. Cl.  
*A61N 1/02* (2006.01)  
*A61N 1/36* (2006.01)  
*A61N 1/372* (2006.01)  
*A61N 1/39* (2006.01)  
*A61M 5/142* (2006.01)  
*A61F 2/12* (2006.01)

(52) U.S. Cl. .................. 607/5; 607/36; 607/2; 607/151; 623/8

(58) Field of Classification Search .................. None  
See application file for complete search history.

(56) References Cited

U.S. PATENT DOCUMENTS

| | | | |
|---|---|---|---|
| 4,298,997 A | | 11/1981 | Rybka |
| 4,326,532 A | * | 4/1982 | Hammar ............ 604/266 |
| 4,980,449 A | | 12/1990 | Kohn et al. |
| 5,216,115 A | | 6/1993 | Kohn et al. |
| 5,217,493 A | * | 6/1993 | Raad et al. .......... 623/11.11 |
| 5,587,507 A | | 12/1996 | Kohn et al. |
| 5,614,284 A | | 3/1997 | Kranzler et al. |
| 5,670,602 A | | 9/1997 | Kohn et al. |
| 5,676,146 A | | 10/1997 | Scarborough |
| 5,853,745 A | | 12/1998 | Darouiche |

(Continued)

FOREIGN PATENT DOCUMENTS

EP 0971753 B1 10/2005

(Continued)

OTHER PUBLICATIONS

Prevent, WordNet, 2011.*

(Continued)

*Primary Examiner* — Robert A Wax  
*Assistant Examiner* — William Craigo  
(74) *Attorney, Agent, or Firm* — Lerner, David, Littenberg, Krumholz & Mentlik, LLP

(57) ABSTRACT

Biodegradable polymer-coated surgical meshes formed into pouches are described for use with cardiac rhythm management devices (CRMs) and other implantable medical devices. Such meshes are formed into a receptacle, e.g., a pouch or other covering, capable of encasing, surrounding and/or holding the cardiac rhythm management device or other implantable medical device and preventing or retarding the formation of a biofilm.

13 Claims, 19 Drawing Sheets

U.S. PATENT DOCUMENTS

| | | | |
|---|---|---|---|
| 6,120,491 A * | 9/2000 | Kohn et al. | 604/502 |
| 6,548,569 B1 | 4/2003 | Williams et al. | |
| 6,656,488 B2 | 12/2003 | Yi et al. | |
| 6,838,493 B2 | 1/2005 | Williams et al. | |
| 6,887,270 B2 | 5/2005 | Miller et al. | |
| 6,981,944 B2 | 1/2006 | Jamiolkowski et al. | |
| 2002/0072694 A1 | 6/2002 | Snitkin et al. | |
| 2002/0151668 A1 | 10/2002 | James et al. | |
| 2003/0091609 A1 | 5/2003 | Hendriks | |
| 2003/0138488 A1 | 7/2003 | Kohn et al. | |
| 2003/0153983 A1 | 8/2003 | Miller et al. | |
| 2003/0216307 A1 | 11/2003 | Kohn et al. | |
| 2004/0186528 A1 | 9/2004 | Ries | |
| 2004/0209538 A1 | 10/2004 | Klinge et al. | |
| 2004/0254334 A1 | 12/2004 | James et al. | |
| 2005/0008671 A1* | 1/2005 | Van Antwerp | 424/423 |
| 2005/0101692 A1 | 5/2005 | Sohier et al. | |
| 2005/0147690 A1 | 7/2005 | Masters et al. | |
| 2005/0149157 A1 | 7/2005 | Hunter et al. | |
| 2005/0161859 A1 | 7/2005 | Miller et al. | |
| 2005/0163821 A1 | 7/2005 | Sung et al. | |
| 2005/0165203 A1 | 7/2005 | Kohn et al. | |
| 2005/0228471 A1 | 10/2005 | Williams et al. | |
| 2006/0025852 A1 | 2/2006 | Armstrong et al. | |
| 2006/0121179 A1 | 6/2006 | Pacetti | |
| 2007/0198040 A1* | 8/2007 | Buevich et al. | 606/151 |
| 2008/0107709 A1 | 5/2008 | Kohn et al. | |
| 2008/0132922 A1* | 6/2008 | Buevich et al. | 606/151 |
| 2009/0029961 A1* | 1/2009 | Modak et al. | 514/184 |
| 2009/0088548 A1 | 4/2009 | Moses et al. | |
| 2010/0015237 A1 | 1/2010 | Moses et al. | |
| 2010/0074940 A1 | 3/2010 | Schwartz et al. | |
| 2010/0129417 A1 | 5/2010 | Moses et al. | |
| 2010/0130478 A1 | 5/2010 | Moses et al. | |
| 2010/0167992 A1 | 7/2010 | Schwartz et al. | |

FOREIGN PATENT DOCUMENTS

| | | |
|---|---|---|
| JP | 07-000430 A | 1/1995 |
| JP | 2000-512519 A | 9/2000 |
| JP | 2002-500065 A | 1/2002 |
| JP | 2002-522112 A | 7/2002 |
| JP | 2004-524059 A | 8/2004 |
| JP | 2004-535866 A | 12/2004 |
| JP | 2005-152651 A | 6/2005 |
| WO | 9747254 A1 | 12/1997 |
| WO | WO 99/24107 | 5/1999 |
| WO | 9934750 A1 | 7/1999 |
| WO | WO 99/52962 | 10/1999 |
| WO | WO 01/49249 | 7/2001 |
| WO | WO 01/49311 | 7/2001 |
| WO | WO 03/091337 | 11/2003 |
| WO | 2004071485 A1 | 8/2004 |
| WO | 2005/011767 A1 | 2/2005 |
| WO | WO 2008/127411 | 10/2008 |
| WO | WO 2008/136856 | 11/2008 |
| WO | WO 2008/121816 | 12/2008 |
| WO | WO 2009/113972 | 9/2009 |

OTHER PUBLICATIONS

Zoll, Annals of Surgery, Sep. 1964.*

Agostinho, A. et al., "Inhibition of *Staphylococcus aureus* Biofilms by a Novel Antibacterial Envelope for Use with Implantable Cardiac Devices," Clinical and Translational Science, 2009, vol. 2(3), pp. 193-198.

Ajmal, N. et al., "The Effectiveness of Sodium 2-Mercaptoethane Sulfonate (Mesna) in Reducing Capsular Formation around Implants in a Rabbit Model," 2003, Plastic and Reconstructive Surgery, vol. 112(5), pp. 1455-1461.

Bach, A. et al., "Retention of antibacterial activity and bacterial colonization of antiseptic-bonded central venous catheters," J. Antimicrob. Chemother., 1996, vol. 37(2), pp. 315-322.

Darouiche, R. O. et al., "A comparison of two antimicrobial-impregnated central venous cathethers," The New England Journal of Medicine, 1999, vol. 340(1), pp. 1-8.

Darouiche, R. O. et al., "Efficacy of antimicrobial-impregnated silicone sections from penile implants in preventing device colonization in an animal model," Urology, 2002, vol. 59, pp. 303-307.

Darouiche, R. O. et al., "In vivo efficacy of antimicrobe-impregnated saline-filled silicone implants," Plast. Reconstr. Surg., 2002, vol. 109(4), pp. 1352-1357.

Engelmayr, G. C., Jr. et al., "A novel bioreactor for the dynamic flexural stimulation of tissue engineered heart valve biomaterials," Biomaterials, 2003, vol. 24, pp. 2523-2532.

George, S. J. et al., "Antiseptic-impregnated central venous catheters reduce the incidence of bacterial colonization and associated infection in immunocompromised transplant patients," Eur. J. Anaesthesiol., 1997, vol. 14, pp. 428-431.

Greca, F. H. et al., "The influence of differing pore sizes on the biocompatibility of two polypropylene meshes in the repair of abdominal defects," Hernia, 2001, vol. 5, pp. 59-64.

Hambraeus, A. et al., "Bacterial contamination in a modern operating suite, 2. Effect of a zoning system on contamination of floors and other surfaces," J. Hyg., 1978, vol. 80, pp. 57-67.

Hayes, B. B. et al., "Evaluation of percutaneous penetration of natural rubber latex proteins," Toxicol. Sci., 2000, vol. 56, pp. 262-270.

Hospital Infections Program, National Center for Infectious Disease, CDC, "Public Health Focus: Surveillance, Prevention, and Control of Nosocomial Infections," MMWR Weekly, 1992, vol. 41, pp. 783-787.

Khodorova, A. B. et al., "The addition of dilute epinephrine produces equieffectiveness of bupivacaine enantiomers for cutaneous analgesia in the rat," Anesth. Analg., 2000, vol. 91, pp. 410-416.

Kramer, C. et al., "A fatal overdose of transdermally administered fentanyl," J. Am. Osteopath. Assoc., 1998, vol. 98(7), pp. 385-386.

Leblanc, K. A., et al., "Evaluation of continuous infusion of 0.5% bupivacaine by elastomeric pump for postoperative pain management following open inguinal hernia repair," J. Am. Coll. Surg., 2005, vol. 200(2), pp. 198-202.

Maki, D. G. et al., "Prevention of central venous catheter-related bloodstream infection by use of an antiseptic-impregnated catheter: A randomized, controlled trial," Annals of Internal Medicine, 1997, vol. 127(4), pp. 257-266.

Meakins, J. L., "Prevention of postoperative infection," ACS Surgery: Principals and Practice, American College of Surgeons, 2005, pp. 1-20.

Morrow, T. J. et al, "Suppression of bulboreticular unit responses to noxious stimuli by analgesic mesencephalic stimulation," Somatosensory Research, 1983, vol. 1(2), pp. 151-168.

Perencevich, E. N. et.al., "Health and economic impact of surgical site infections diagnosed after hospital discharge," Emerging Infect. Dis., 2003, vol. 9(2), pp. 196-203.

Sanchez, B. et al., "Local anesthetic infusion pumps improve postoperative pain after inguinal hernia repair," The American Surgeon, 2004, vol. 70, pp. 1002-1006.

Segura, M. et al., "A clinical trial on the prevention of catheter-related sepsis using a new hub model," Ann. Surg., 1996, vol. 223(4), pp. 363-369.

Tennenberg, S. et al., "A prospective randomized trial of an antibiotic- and antiseptic-coated central venous catheter in the prevention of catheter-related infections," Arch. Surg., 1997, vol. 132, pp. 1348-1351.

van't Riet, M. et al, "Prevention of adhesion to prosthetic mesh: Comparison of different barriers using an incisional hernia model," Annals of Surgery, 2003, vol. 237, No. 1, pp. 123-128.

Final Office Action for U.S. Appl. No. 11/672,929, mailed Aug. 16, 2010, 19 pages.

Final Office Action for U.S. Appl. No. 11/936,049, mailed Dec. 21, 2010, 20 pages.

Final Office Action for U.S. Appl. No. 12/058,060, mailed Oct. 13, 2010, 19 pages.

Areolar Tissue, The Free Dictionary, May 2011.

Rupp, Clinical Infectious Diseases, vol. 19, 1994.

Darouiche, NEJM, 340, 1999.

Green, Clinical Cornerstone, vol. 3, 2001.

Greca, Hernia, 5, 2001.

TYRX Pharma, Inc. Announces Submission of a Premarket Application for PIVIT CRM, TYRX Press Releases [searched on Apr. 16, 2012], USA, Oct. 16, 2006, URL, http://www.tyrx.com/Collateral/Documents/TyRx%20English-US/10-16-06-pr.pdf.

TyRx Pharama, Inc., TyRx Press Releases, TyRx Announces FDA 510(k) Filing for New Surgical Mesh, USA, May 17, 2005, [searched on May 2, 2012], URL, http://www.tyrx.com/Collateral/Documents/TyRx%20English-US/10-17-05-pr.pdf.

TyRx Pharama, Inc., TyRx Press Releases, TyRx Pharama's Anesthetic Coated Surgical Mesh Combination Product Assigned to "Device" Center at FDA, USA, Jan. 9, 2006, [searched on May 2, 2012], URL, http://www.tyrx.com/Collateral/Documents/TyRx%20English-US/01-09-06-pr.pdf.

TyRx Pharama, Inc., TyRx Press Releases, TyRx Announces FDA 510(k) Filing for New Antibiotic Eluting Surgical Mesh, USA, Jan. 17, 2006, [searched on May 2, 2012] URL, http://www.tyrx.com/Collateral/Documents/TyRx%20English-US/01-17-06-pr.pdf.

* cited by examiner

RABBIT #8245 LEFT –
PACEMAKER WITH AIGIS (S. EPIDERMIDIS)

RABBIT #8245 RIGHT –
PACEMAKER ALONE (S. EPIDERMIDIS)

RABBIT #8245 LEFT
PACEMAKER WITH AIGIS
CONFOCAL IMAGE (S. EPIDERMIDIS)

RABBIT #8245 RIGHT
PACEMAKER ALONE
CONFOCAL IMAGE (S. EPIDERMIDIS)

RABBIT #8247 LEFT –
PACEMAKER WITH AIGIS (S. CAPITIS)
NO GROSS PHOTO AVAILABLE

RABBIT #8247 RIGHT –
PACEMAKER ALONE (S. CAPITIS)

RABBIT #8247 LEFT –
PACEMAKER WITH AIGIS
CONFOCAL IMAGE (S. CAPITIS)

RABBIT #8247 RIGHT –
PACEMAKER ALONE
CONFOCAL IMAGE (S. CAPITIS)

RABBIT #8251 LEFT –
PACEMAKER WITH AIGIS (E. COLI)

RABBIT #8251 RIGHT –
PACEMAKER ALONE (E. COLI)

RABBIT #8251 LEFT –
PACING DEVICE WITH AIGIS
CONFOCAL IMAGE (E. COLI)

RABBIT #8251 RIGHT –
PACEMAKER ALONE
CONFOCAL IMAGE (E. COLI)

RABBIT #8327 LEFT –
PACING DEVICE WITH AIGIS (S. AUREUS)
NO GROSS PHOTO AVAILABLE

RABBIT #8327 RIGHT –
PACEMAKER ALONE (S. AUREUS)
NO GROSS PHOTO AVAILABLE

RABBIT #8327 LEFT –
PACING DEVICE WITH AIGIS
CONFOCAL IMAGE (S. AUREUS)

RABBIT #8327 RIGHT –
PACEMAKER ALONE
CONFOCAL IMAGE (S. AUREUS)

RABBIT #8246 LEFT –
PACEMAKER WITH AIGIS (S. EPIDERMIDIS)

RABBIT #8246 RIGHT –
PACEMAKER ALONE (S. EPIDERMIDIS)

RABBIT #8244 LEFT –
PACEMAKER WITH AIGIS (S. CAPITIS)

RABBIT #8244 RIGHT –
PACEMAKER ALONE (S. CAPITIS)

RABBIT #8248 LEFT –
PACEMAKER WITH AIGIS (E. COLI)

RABBIT #8248 RIGHT –
PACEMAKER ALONE (E. COLI)

RABBIT #8320 LEFT –
PACING DEVICE WITH AIGIS (S. AUREUS)

RABBIT #8320 RIGHT –
PACEMAKER ALONE (S. AUREUS)

RABBIT #9646 LEFT – REPEAT GROUP 1
PACEMAKER ALONE (S. AUREUS)

RABBIT #9646 RIGHT – REPEAT GROUP 1
PACING DEVICE WITH AIGIS (S. AUREUS)

RABBIT #9642 LEFT – REPEAT GROUP 2
PACEMAKER ALONE (S. EPIDERMIDIS)

RABBIT #9642 RIGHT – REPEAT GROUP 2
PACING DEVICE WITH AIGIS (S. EPIDERMIDIS)

RABBIT #8246 LEFT –
PACEMAKER WITH AIGIS (S. EPIDERMIDIS)

RABBIT #8246 RIGHT –
PACEMAKER ALONE (S. EPIDERMIDIS)

RABBIT #8244 LEFT –
PACEMAKER WITH AIGIS (S. CAPITIS)

RABBIT #8244 RIGHT –
PACEMAKER ALONE (S. CAPITIS)
NO PHOTO AVAILABLE

RABBIT #8248 LEFT –
PACEMAKER WITH AIGIS (E. COLI)

RABBIT #8248 RIGHT –
PACEMAKER ALONE (E. COLI)

RABBIT #8320 LEFT —
PACING DEVICE WITH AIGIS (S. AUREUS)

RABBIT #8320 RIGHT —
PACEMAKER ALONE (S. AUREUS)

RABBIT #9646 LEFT (REPEAT GROUP 1) —
PACEMAKER ALONE (S. AUREUS)

RABBIT #9646 RIGHT (REPEAT GROUP 1) —
PACING DEVICE WITH AIGIS (S. AUREUS)

RABBIT #9642 LEFT (REPEAT GROUP 2) —
PACEMAKER ALONE (S. EPIDERMIDIS)

RABBIT #9642 RIGHT (REPEAT GROUP 2) —
PACING DEVICE WITH AIGIS (S. EPIDERMIDIS)

PREVENTING BIOFILM FORMATION ON IMPLANTABLE MEDICAL DEVICES

This application is a continuation-in-part of U.S. Ser. No. 11/936,054, filed Nov. 6, 2007, which is a continuation-in-part of U.S. Ser. No. 11/672,929, filed Feb. 8, 2007. This application claims the benefit of U.S. Provisional Patent Application No. 61/140,918, filed Dec. 26, 2008; U.S. Ser. No. 11/936,054 claims the benefit of U.S. Provisional Application Nos. 60/864,597 filed Nov. 6, 2006 and 60/984,254 filed Oct. 31, 2007; U.S. Ser. No. 11/672,929 claims the benefit of U.S. Provisional Application No. 60/771,827 filed Feb. 8, 2006. Each of the aforementioned applications are incorporated herein by reference in their entirety for all purposes.

BACKGROUND OF THE INVENTION

Prosthetic implants such as meshes, combination mesh products or other porous prostheses are commonly used to provide a physical barrier between types of tissue or extra strength to a physical defect in soft tissue. However, such devices are often associated with post-surgical complications including post-implant infection, pain, excessive scar tissue formation and shrinkage of the prosthesis or mesh. Excessive scar tissue formation, limited patient mobility, and chronic pain are often attributed to the size, shape, and mass of the implant and a variety of efforts have been undertaken to reduce the amount of scar tissue formation. For example, lighter meshes using smaller fibers, larger weaves, and/or larger pore sizes as well as meshes woven from both non-resorbable and resorbable materials are in use to address these concerns.

For treating acute pain and infection, patients with implanted prostheses are typically treated post-operatively with systemic antibiotics and pain medications. Patients will occasionally be given systemic antibiotics prophylactically; however, literature review of clinical trials does not indicate that systemic antibiotics are effective at preventing implant-related infections.

In 1992, it was reported that nosocomial infections involved over 2 million patients each year and cost the healthcare systems over 4.5 billion dollars annually.[1] Today, these numbers are undoubtedly much higher. Surgical site infections, involving approximately 500,000 patients, represent the second most common cause of nosocomial infections and approximately 17% of all hospital-acquired infections.[2] The incidence of infections associated with the placement of pacemakers has been reported as 0.13 to 19.9% at an average cost of $35,000 to treat these complications which most often involves complete removal of the implant.[3,4]

Post-operative infection is tied to a number of different elements: lack of host defense mechanisms, the clinical site where the surgery is performed, the length of the surgery, and bacteria present at the time of device implantation.[5] The general health of the patient (i.e., the host factor) is always important; however, since many patients requiring surgery are compromised in some way—and there is little that can be done to mitigate that factor—controlling the other two factors becomes important.

Studies have shown that patients are exposed to bacterial contamination in the hospital, especially in the operating room (OR) and along the route to the OR.[6] In fact, bacterial counts of up to $7.0 \times 10^4$ CFU/mL[2] have been found in the OR dressing area.[6] In addition, many surgical procedures are not performed in a "formal" OR, but rather are performed in a day-surgery or out-patient surgical center (e.g., procedures such as changing batteries in medical devices are not necessarily carried out in an OR). Recent improvements in air handling and surface cleansing have reduced the environmental levels of infectious agents, but not eliminated them. Consequently, further means to reduce bacterial contamination or to reduce the potential for bacterial infection are desirable.

Controlling the inoculation levels is the third component to the intra- and post-operative surgical infection control triad. One aspect to microbial control is the use antibiotics. For example, one practice advocates the administration of systemic antibiotics within 60 minutes prior to incision, with additional dosing if the surgery exceeds 3 hours.[5] Such pre-incision administration has shown some positive effects on the incidence of infection associated with the placement of pacemakers.[7] Surgeons also routinely wash the surgical site with an antimicrobial agent such as an Iodophor or antibiotic or a combination of agents. None of these procedures have been standardized nor have they been found to be efficacious. An adjunctive approach to managing the potential for implant contamination has been the introduction of antimicrobial agents on implantable medical devices.[8,9]

This approach was initially developed to create a barrier to microbial entry into the body via surface-penetrating devices, such as indwelling catheters,[9-11] The antimicrobial agents were applied in solution as a direct coating on the device to prevent or reduce bacterial colonization of the device and, therefore, reduce the potential for a device-related infection. While a number of clinical trials have demonstrated that antimicrobial coating on devices, such as central venous catheters reduce device colonization, reduction of infection has not been statistically significant although the numerical trends show a reduction in patient infection.[12-18] These results are highly relevant since they tend to establish that, with proper aseptic and surgical techniques as well as administration of appropriate antibiotic therapy, the use of surface-modified devices has a positive impact on the overall procedural/patient outcome.[12,13]

The development of post-operative infection is dependent on many factors, and it is not clear exactly how many colony forming units (CFUs) are required to produce clinical infection. It has been reported that an inoculation of $10^3$ bacteria at the surgical site produces a wound infection rate of 20%.[5] And while current air-handling technology and infection-control procedures have undoubtedly reduced the microbial levels in the hospital setting, microbial contamination of an implantable device is still possible. It is known that bacteria, such as *Staphylococcus* can produce bacteremia within a short time after implantation (i.e., within 90 days) with a device or lay dormant for months before producing an active infection so eradication of the bacterial inoculum at the time of implantation is key and may help to reduce late-stage as well as early-stage device-related infections.[22]

For example, the combination of rifampin and minocycline has demonstrated antimicrobial effectiveness as a coating for catheters and other implanted devices, including use of those drugs in a non-resorbable coating such as silicone and polyurethane.[13, 19-21] The combination of rifampin and minocycline has also been shown to reduce the incidence of clinical infection when used as a prophylactic coating on penile implants.

U.S. Ser. No. 11/672,929 describes a bioresorbable polymer coating on a surgical mesh as a carrier for the antimicrobial agents rifampin and minocycline. Such meshes can be fashioned into a pouch of various sizes and shapes to match the implanted pacemakers, pulse generators, defibrillators and other implantable medical devices. The addition of the antimicrobial agents permits the pouch to deliver antimicrobial agents at the implant site and thus to provide a barrier to microbial colonization of a CRM during surgical implantation as an adjunct to surgical and systemic infection control.

During the period from 1996-2003, there was a 49% rise in the number of new cardiac rhythm medical device (CRM or CRMD implantations but a 310% increase in the number of hospitalizations due to infections related to CRM implants. (2.8 fold increase for pacemakers and 6-fold increase for ICDs). Further, CRM infection increased the risk of in-hospital death more than 2-fold. The challenges faced when treating such implant infections emphasize the critical need to develop improved methods of preventing the infection of implantable devices.

Hence, the incidence of implantable device-related infections continues to pose significant clinical problems, not only with CRMs. but also with other implantable devices such as neurostimulators and infusion pumps are susceptible to infection risks.

The most common bacterial strains involved in the etiology of cardiac device infections include *Staphylococcus aureus* (*S. aureus*), and coagulase-negative *Staphylococci* such as *S. epidermidis*. Staphylococcal species, including methicillin-resistant *S. aureus* (MRSA), account for more than ⅔ of cardiac device infections in most published series. These bacteria are able to adhere to device surfaces and in some cases form a biofilm consisting of a polysaccharide matrix surrounding the microorganisms. This matrix protects the microorganisms from antibiotics and host defenses, making the infection highly resistant to antibiotic regimens. Cardiac device infections by these microorganisms most often occur within the generator pocket, and are believed to be due mainly to local contamination at the time of device implantation. Studies have shown that approximately 30% of the patients with pocket infections also had bacteremia. In most cases, whether the patient presents with bacteremia or not, infection of the intravascular portion of the lead is often present, generally caused by progression of the infection from the generator pocket. Due to the ineffectiveness of systemic antibiotics to penetrate through tissue and reach high enough concentrations to eradicate the localized device contamination and pocket infection, as well as the involvement of generator and leads, the prevailing medical opinion is that surgical removal of the generator and leads is the most effective treatment once a pocket infection is diagnosed. This type of surgical treatment is both costly and risky for patients dependent on the device. The estimated cost to treat each infection is $32,000, with total estimated costs of all device-related infections estimated at $640 million per year, excluding the costs of device replacement.

Meta-analysis of prospective randomized trials suggests a consistent protective effect against CRMD infections by using systemic antibiotics pre- and post-implantation. However, while the use of pre- and post-operative systemic antibiotics is proven effective, several studies demonstrate a lack of consistent compliance with standards for preventing surgical site infections. The lack of compliance, along with a desire to reduce the use of systemic antibiotics to minimize the development of resistant organisms, provides significant motivation to develop a more effective means to prevent the initial infection at the time of implant.

Coating antimicrobial agents directly onto implantable medical devices or impregnating such devices with antimicrobial agents can potentially eliminate or reduce the microorganism burden at implant, and has been proposed to provide a device with "long lasting resistance to staphylococcal biofilm colonization" by coating or impregnating rifampin and minocycline, or rifampin and novobiocin, on the surface of an indwelling medical devices (Abstract, U.S. Pat. No. 5,217,493 and generally, U.S. Pat. Nos. 5,624,704 and 5,902,283). In another example, impregnation of central venous catheters with a combination of rifampin and minocyclin has been associated with a reduction of catheter-associated bacteremia. However, these impregnated devices have minimal capacity to elute the antimicrobial agents into the surrounding tissue and little if any ability to deliver it in more than minuscule quantities by virtue of the methodology employed to coat or impregnate the drugs. These limitations may make prevention or reduction of biofilm formation less effective, and may increase the development of resistant strains by eluting such low quantities of drug such that all organisms are not eradicated.

Pocket infection remains one of the most significant problems facing CRM implants, with reports of 2-8% of implants developing infection. Because the infections typically include biofilm formation on the device surface, antibiotics are largely ineffective in eliminating the etiologic microorganisms because, at least in part, the biofilm protects the bacteria residing within the biofilm from destruction. Novel products aimed at preventing not only device colonization but also biofilm formation at the time the pocket is contaminated may provide an important step in reducing device infections.

The present invention demonstrates that a pouch made of biopolymer/polypropylene mesh incorporated with one or more antimicrobial drugs is effective at preventing bacteria from colonizing the device and forming biofilms.

In addition, the present invention addresses these needs (preventing or inhibiting infections) as well as others, such as pain relief and inhibition or reduction of scar tissue, fibrosis and the like, by providing temporarily stiffened meshes formed into pouches or other receptacles to hold an implantable medical device upon implantation.

SUMMARY OF THE INVENTION

The present invention relates to pouches, coverings and the like made from implantable surgical meshes comprising one or more biodegradable polymer coatings. The mesh pouches of the invention can be shaped as desired into pouches, bags, coverings, shells, skins, receptacles and the like to fit any implantable medical device. Preferred meshes of the invention are comprised of woven polypropylene coated with one or more biodegradable polymer to impart drug elution or other temporary effects.

As used herein, "pouch," "pouches," "mesh pouch," "mesh pouches," "pouch of the invention" and "pouches of the invention" means any pouch, bag, skin, shell, covering, or other receptacle made from an implantable surgical mesh comprising one or more biodegradable polymer coatings and shaped to encapsulate, encase, surround, cover or hold, in whole or in substantial part, an implantable medical device. The pouches of the invention have openings to permit leads and tubes of the IMD to extend unhindered from the IMD though the opening of the pouch. The pouches may also have porosity to accommodate monopolar devices that require the IMD to be electrically grounded to the surrounding tissue. An IMD is substantially encapsulated, encased, surrounded or covered when the pouch can hold the device and at least 20%, 30%, 50%, 60%, 75%, 85%, 90%, 95% or 98% of the device is within the pouch or covered by the pouch.

In accordance with this invention, the coated surgical meshes can be formed to encapsulate a pacemaker, a defibrillator, a generator, an implantable access system, a neurostimulator, or any other implantable device for the purpose of securing them in position, providing pain relief, inhibiting scarring or fibrosis and/or inhibiting bacterial growth. Such coated meshes are formed into an appropriate shape either before or after coating with the biodegradable polymers.

In one aspect, the pouches of the invention may act as medical prostheses (providing support to or "stabilizing" the device and the tissue surrounding the area of implant, e.g., to minimize movement of the device in the body of the patient), and are thus also referred to as medical prostheses.

Hence, the pouches of the invention comprise a mesh and one or more coating which temporarily stiffens the mesh to at least 1.1 times its original stiffness. The coatings on such meshes do not alter the integrity of the mesh and thus allow the mesh to remain porous. In general, the coatings do not substantially alter the porosity of the mesh. More particularly, the pouches of the invention comprise a mesh with one or more coatings with at least one of the coatings comprising a stiffening agent(s) that coats the filaments or fibers of the mesh so to temporarily immobilize the contact points of those filaments or fibers. Again, the coatings on such meshes do not alter the integrity or strength of the underlying mesh and allow the mesh to remain porous after coating. In general, the coatings do not substantially alter the porosity of the mesh. The meshes are capable of substantially reverting to their original stiffness under conditions of use.

The stiffening agents, i.e., as applied in the coatings of the invention, can selectively, partially or fully coat the contact points of the filaments or said fibers of the mesh to create a coating. The contact points generally include the knots of woven meshes. Such coating can be positioned on the mesh in a templated pattern or in an array such as might be deposited with ink jet type technology, including computer controlled deposition techniques. Additionally, the coatings can be applied on one or both sides of the mesh.

In some embodiments, the stiffening agents include hydrogels, either alone or in combination with one or more biodegradable polymers. In some embodiments, the stiffening agent is one or more biodegradable polymers, and can be applied in layers. One or more biodegradable polymers can be used per individual coating layer. Preferred biodegradable polymer comprises one or more tyrosine-derived diphenol monomer units as polyarylates, polycarbonates or polyiminocarbonates.

In another aspect of the invention, the pouches of the invention have at least one of the coatings that further comprise one or more drugs. Such drugs include, but are not limited to, antimicrobial agents, anesthetics, analgesics, anti-inflammatory agents, anti-scarring agents, anti-fibrotic agents, leukotriene inhibitors as well as other classes of drugs, including biological agents such as proteins, growth inhibitors and the like.

The biodegradable polymer coatings are capable of releasing one or more drugs into surrounding bodily tissue and proximal to the device such that the drug reduces or prevents implant- or surgery-related complications. For example, by including an anesthetic agent in the coating that predictably seeps or elutes into the surrounding bodily tissue, bodily fluid, or systemic fluid, one has a useful way to attenuate pain experienced at the implantation site. In another example, replacing the anesthetic agent with an anti-inflammatory agent provides a way to reduce the swelling and inflammation associated implantation of the mesh, device and/or pouch. In yet another example, by delivering an antimicrobial agent in the same manner, one has a way to provide a rate of drug release sufficient to prevent colonization of the mesh pouch, the CRM or other IMD and/or the surgical implantation site by bacteria for at least the period following surgery necessary for initial healing of the surgical incision.

In other embodiments, the pouches of the present invention are suitable for the prevention and/or retardation of biofilm formation on an implantable medical device. In accordance with the invention, the present method is directed to implanting, in a subject, a medical device which is enveloped or covered, in whole or in part, in a polymer pouch (including both fully resorbable and partially resorbable or non-resorbable pouches) which elute one or more antimicrobial agents in amounts effective to prevent or retard biofilm formation on the device, preferably for an extended period of time. In one embodiment the non-resorbable pouch is a polymer-coated polypropylene mesh that elutes drug. In another embodiment, the polymer pouch is a moldable and resorbable composition consisting essentially of (i) one or more one resorbable polymers and (ii) one or more antimicrobial agents in amounts effective to prevent biofilm formation.

The coatings on the pouches of the invention can deliver multiple drugs from one or more independent layers, some of which may contain no drug.

The invention thus provides a method of delivering drugs at controlled rates and for set durations of time using biodegradable, resorbable polymers from a coating on a surgical mesh formed as a pouch of the invention.

DETAILED DESCRIPTION OF THE INVENTION

Figure 1:
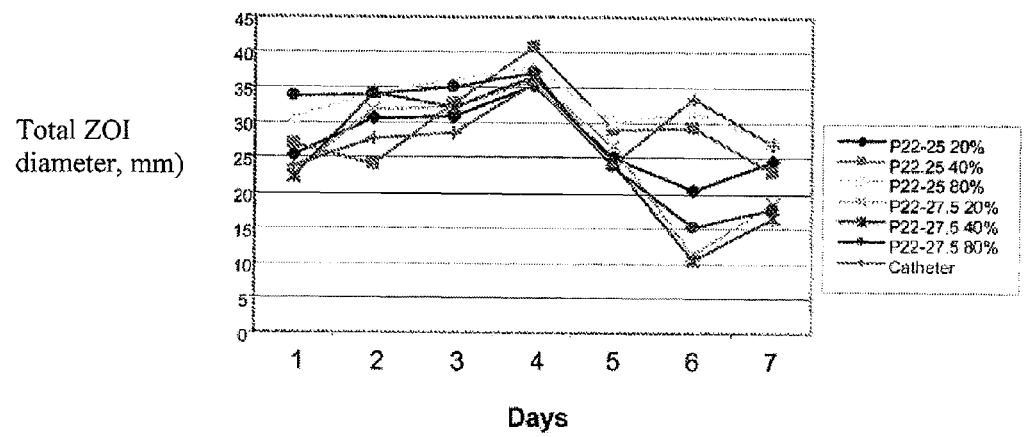
FIG. 1. graphically depicts the zone of inhibition (ZOI) for polyarylate-coated meshes containing rifampin and minocycline hydrochloride that have been incubated on *Staphylococcus aureus* lawns for the indicated times (Example 1). The symbols represent the following meshes: ♦, P22-25 20 passes; ■, P22-25 40 passes; ▲, P22-25 80 passes; x, P22-27.5 20 passes; *, P22-27.5 40 passes; ●, P22-27.5 80 passes; and |, catheter.

All documents cited are herein incorporated by reference in their entirety for all purposes. The citation of any document is not to be construed as an admission that it is prior art with respect to the present invention.

Biofilm formation and development on a medical device occurs in distinct stages. First, the bacterial or fungal cells reversibly attached to a surface (e.g., the surface of a medical device or implant) through weak hydrophobic interactions and electrostatic forces. This attachment step depends upon a number of factors, including the composition or material comprising the device surface, as well as the surface texture, surface charge, and hydrophobicity of the device surface. For example, microbes typically adhere more readily to polymeric surfaces than metallic surfaces, rough surfaces more readily than smooth surfaces, and hydrophobic surfaces more readily than hydrophilic surfaces. The charge of the device surface can also play a role: microorganisms, including staphylococci, are more likely to bind positively-charge polymer surfaces than negatively-charge surfaces. In addition to device factors, host proteins are thought to play a vital role in the attachment of microbes to device surfaces. Implanted devices rapidly become coated with a film of host-derived proteins including fibronectin, fibrinogen fibrin, albumin, collagen, lamina vitronectin, elastin, and von Willebrand factor (vWf). Many of these proteins, most notably fibronectin, fibrinogen fibrin and vWf promote and enhance the binding of Gram-positive cocci, Gram-negative bacilli, and *Candida albicans*. The second stage, irreversible adhesion, occurs when organisms bind irreversibly to a surface via microbial cell surface adhesins and become extremely resistant to extreme shear stress. During the third stage of aggregation, the attached organisms begin to secrete EPS and coalesce to form microcolonies which constitute the basic structural units of all biofilms. Finally, during the subsequent growth and maturation stages, individual microcolonies within the biofilm continue to grow and develop and eventually become separated from other microcolonies.

The growth rate, size and final shape of biofilms are highly organism-specific. Biofilms can comprise Gram-negative, Gram positive bacteria, and/or yeasts. Commonly isolated Gram-positive organisms include *S. aureus, S. epidermis* (and other coagulase-negative staphylococci), enterococci, and streptococci. Frequently isolated Gram-negative bacilli include *Escherichia coli, Klebsiella pneumoniae, Proteus mirabilis*, and *Pseudomonas aeruginosa. Acinetobacter* spp. and *Candida* spp. can also form biofilms. Biofilms formed on medical devices can comprise a single organism or multiple types of organisms, including both bacteria and yeast.

The method of the present invention for preventing and/or retarding biofilm formation on implantable medical devices susceptible to the formation of biofilms, comprises enveloping or covering the medical device with a pouch as described herein, comprising one or more antimicrobial agents (e.g., rifampin and minocyclin), whereby after implantation of the enveloped/covered device, the formation of biofilms prevented or retarded. The method of the present invention is particularly suitable for the prevention or retardation of biofilms for medical devices particularly susceptible to the formation of biofilms (e.g., vascular catheters, explanted catheter leads, cardiovascular rhythm management devices, breast implants, etc.) or for surgical procedures in which biofilm formation is of particular concern or in which it is difficult to avoid contamination of the surgical site with biofilm forming microorganisms.

The pouches of the invention are formed from the coated implantable surgical meshes and comprise a surgical mesh and one or more biodegradable polymer coating layers with each coating layer optionally, and independently, further containing a drug. The physical, mechanical, chemical, and resorption characteristics of the coating enhance the clinical performance of the mesh and the surgeon's ability to implant the device. These characteristics are accomplished by choosing a suitable coating thickness and the biodegradable polymer.

Mesh

A mesh in accordance with the invention is any web or fabric with a construction of knitted, braided, woven or non-woven filaments or fibers that are interlocked in such a way to create a fabric or a fabric-like material. As used in accordance with the present invention, "mesh" also includes any porous prosthesis suitable for temporarily stiffening.

Surgical meshes are well known in the art and any such mesh can be coated as described herein. The meshes used in the present invention are made from biocompatible materials, synthetic or natural, including but not limited to, polypropylene, polyester, polytetrafluoroethylene, polyamides and combinations thereof. One of the advantages of the present invention is that the coatings can be used with any commercially available mesh. A preferred mesh is made from woven polypropylene. Pore sizes of meshes vary. For example the Bard Marlex® mesh has pores of 379±143 micrometers or approx. 0.4 mm, whereas the Johnson and Johnson Vypro® mesh has pores of 3058±62 micrometers or approx. 3 mm.

The stiffening agents of the invention include hydrogels, biodegradable polymers and any other compound capable of imparting temporary stiffness to the mesh in accordance with the invention. Temporary stiffness means that, relative to the corresponding uncoated mesh material, there is an increase in stiffness when one or more coatings are applied in accordance with the invention. Upon use, those coatings then soften or degrade over time in a manner that causes the mesh to revert back to its original stiffness, revert nearly back to its original stiffness or sufficient close to its original stiffness to provide the desired surgical outcome and the expected patient comfort. To determine if the medical prosthesis has temporary stiffness, the prosthesis can be evaluated in vitro or in vivo. For example, a coating can be applied to the mesh and then the mesh left in a physiological solution for a period of time before measuring its stiffness. The time period of stiffness is controlled by the degradation rate (for biodegradable polymers) or absorption ability (for hydrogels). The time period can vary from days, to weeks or even a few months and is most conveniently determined in vitro. Meshes with that revert to their original stiffness in vitro within a reasonable time (from 1 day to 3-4 months) are considered to be temporarily stiffened. Additionally, animal models can be used to assess temporary stiffness by implanting the mesh and then removing it from the animal and determining if its stiffness had changed. Such in vivo results can be correlated with the in vitro results by those of skill in the art. Methods to measure stiffness of a mesh or a coated mesh are known in the art.

A hydrogel is composed of a network of water-soluble polymer chains. Hydrogels are applied as coatings and dried on the mesh. Upon use, e.g., implantation in the body, the hydrogel absorbs water and become soft (hydrogels can contain over 99% water), thereby increasing the flexibility of the mesh and reverting to the original or near original stiffness of the mesh. Typically, hydrogels possess a degree of flexibility very similar to natural tissue, due to their significant water content. Common ingredients for hydrogels, include e.g. polyvinyl alcohol, sodium polyacrylate, acrylate polymers and copolymers with an abundance of hydrophilic groups.

Meshes can have one or more polymer coatings and can optionally include drugs in the coatings. Meshes with a single coating are useful to improve handling of the mesh during surgical implantation and use. Meshes with drugs can be coated with single or multiple layers, depending on the amount of drug to be delivered, the type of drug and desired release rate. Each layer can contain the same or different polymers, the same or different drugs, and the same or different amounts of polymers or drugs. For example, a first coating layer can contain drug, while the second layer coating layer contains either no drug or a lower concentration of drug.

The biodegradable coating deposited onto the surface of the mesh gives the mesh superior handling characteristics relative to uncoated meshes and facilitates surgical insertion because it imparts stiffness to the mesh and thereby improves handling thereof. Over time, however, the coating resorbs, or the stiffening agents degrades or softens, to leave a flexible mesh that provides greater patient comfort without loss of strength.

The surgical mesh can be coated with the biodegradable polymer using standard techniques such as spray or dip coating to achieve a uniform coating having a thickness that provides at least 1.1 to 4.5 and more preferably 1.25 to 2 times the stiffness of the uncoated mesh. In addition, the coating is optimized to provide for a uniform, flexible, non-flaking layer that remains adhered to the mesh throughout the implantation and initial wound healing process. Typically, the polymer coating must maintain its integrity for at least 1 week. Optimal coating solutions are obtained by choosing a biodegradable polymer with a solubility between about 0.01 to about 30% in volatile solvents such as methylene chloride or other chlorinated solvents, THF, various alcohols, or combinations thereof. Additionally, it is preferred to use biodegradable polymers with a molecular weight between about 10,000 and about 200,000 Daltons. Such polymers degrade at rates that maintain sufficient mechanical and physical integrity over about 1 week at 37° C. in an aqueous environment.

Additionally, a biodegradable polymer-coated implantable mesh is described in which the biodegradable polymer layer (i.e., the coating) has a chemical composition that provides relatively good polymer-drug miscibility. The polymer layer can contain between 1-80% drug at room temperature as well as between 1-95%, 2-80%, 2-50%, 5-40%, 5-30%, 5-25% and 10-20% drug or 1, 2, 3, 4, 5, 6, 7, 8, 9, or 10% drug as well as 5% increments from 10-95%, i.e., 10, 15, 20, 25, etc. In one embodiment, the biodegradable polymer coating releases drug for at least 2-3 days. Such release is preferred, for example, when the drug is an analgesic to aide in localized pain management at the surgical site. Such loading and release characteristics can be also be obtained for drug polymer-combinations that do not have good miscibility by using multiple layering techniques.

Additionally, the biodegradable polymer for use with the mesh pouch has a chemical composition complementary to the drug so that the polymer layer can contain between 2-50% drug at room temperature. For certain types of drug, the layer can contain as much as 80-90% drug and acts as drug reservoir (or depot layer) and drug release can be controlled by using multiple layers with varying amounts of drug (from none, to a few percent, saturation or above the solubility limit for the drug in the polymer).

To achieve an analgesic affect, the anesthetic and/or analgesic should be delivered to the injured tissue shortly after surgery or tissue injury. A drug or drugs for inclusion in the coatings on the pouches of the invention include, but are not limited to analgesics, anti-inflammatory agents, anesthetics, antimicrobial agents, antifungal agents, NSAIDs, other biologics (including proteins and nucleic acids) and the like. Antimicrobial and antifungal agents can prevent the mesh pouch, the device and/or the surrounding tissue from being colonized by bacteria. One or more drugs can be incorporated into the polymer coatings on the mesh pouches of the invention.

In another embodiment, a mesh pouch of the invention has a coating comprising an anesthetic such that the anesthetic elutes from the implanted coated mesh to the surrounding tissue of the surgical site for between 1 and 10 days, which typically coincides with the period of acute surgical site pain. In another embodiment, delivery of an antimicrobial drug via a mesh pouch of the invention can create an inhibition zone against bacterial growth and colonization surrounding the implant during the healing process (e.g., usually about 30 days or less) and/or prevent undue fibrotic responses.

Using biodegradable polymer coatings avoids the issue of drug solubility, impregnation or adherence in or to the underlying device since a coating having suitable chemical properties can be deposited onto the mesh, optionally in concert with one or more drugs, to provide for the release of relatively high concentrations of those drugs over extended periods of time. For example, by modulating the chemical composition of the biodegradable polymer coating on the mesh pouch and the coating methodology, a clinically-efficacious amount of anesthetic drug can be loaded onto a mesh pouch to assure sufficient drug elution and to provide surgical site, post-operative pain relief for the patient.

To provide such post-operative, acute pain relief, the mesh pouch should elute from about 30 mg to about 1000 mg of anesthetic over 1-10 days, including, e.g., about 30, 50, 100, 200, 400, 500, 750 or 1000 mg over that time period.

The pouch should elute clinically effective amounts of anesthetic during the acute post-operative period when pain is most noticeable to the patient. This period, defined in several clinical studies, tends to be from 12 hours to 5 days after the operation, with pain greatest around 24 hours and subsiding over a period of several days thereafter. Prior to 12 hours, the patient is usually still under the influence of any local anesthetic injection given during the surgery itself. After the 5-day period, most of the pain related to the surgery itself (i.e., incisional pain and manipulation of fascia, muscle, & nerves) has resolved to a significant extent.

Bupivacaine has a known toxicity profile, duration of onset, and duration of action. Drug monographs recommend the daily dose not to exceed 400 mg. Those of skill in the art can determine the amount of anesthetic to include in a polymer coating or a hydrogel coating to achieve the desired amount and duration of pain relief. Moreover, anesthetics that contain amines, such as lidocaine and bupivacaine, are hydrophobic and are difficult to load in sufficient amounts into the most commonly used plastics employed in the medical device industry, such as polypropylene and other non-resorbable thermoplastics. When in their hydrochloride salt form, anesthetics cannot be effectively loaded in significant concentration into such non-resorbable thermoplastics because of the mismatch in hydrophilicity of the two materials.

There are numerous reports of reduction or complete elimination of narcotic use and pain scores after open hernia repair during days 2-5 with concomitant use of catheter pain pump system. In these cases, the pump delivers either a 0.25% or 0.5% solution of bupivacaine to the subfascial area (Sanchez, 2004; LeBlanc, 2005; and Lau, 2003). At a 2 mL/hour flow rate, this translates into constant "elution" of approximately 120 mg of bupivacaine per day. However, this system purportedly suffers from leakage, so the 120 mg per day may only serve as an extremely rough guide for the amount of bupivacaine that should be delivered to provide adequate post-operative pain relief One of the most well characterized sustained release depot systems for post-operative pain relief reported in the literature is a PLGA microsphere-based sustained release formulation of bupivacaine. This formulation was developed and tested in humans for relief of subcutaneous pain as well as neural blocks. Human trials indicated that subcutaneous pain was relieved via injection of between 90 to 180 mg of bupivacaine which then eluted into the surrounding tissue over a 7-day period, with higher concentrations in the initial 24-hour period followed by a gradual taper of the concentration. Other depot sustained-release technologies have successfully suppressed post-operative pain associated with inguinal hernia repair. For example, external pumps and PLGA microsphere formulations have each purportedly release drug for approximately 72 hours.

To achieve loading at the lower limit of the elution profile, for example, one can choose a relatively hydrophilic biodegradable polymer and combine it with the anesthetic hydrochloride salt so that the anesthetic dissolves in the polymer at a concentration below the anesthetic's saturation limit. Such a formulation provides non-burst release of anesthetic. To achieve loading at the upper limit of the elution profile, one can spray coat a layer of an anesthetic-polymer mixture that contains the anesthetic at a concentration above its saturation limit. In this formulation, the polymer does not act as a control mechanism for release of the anesthetic, but rather acts as a binder to hold the non-dissolved, anesthetic particles together and alters the crystallization kinetics of the drug. A second coating layer, which may or may not contain further anesthetic, is sprayed on top of the first layer. When present in the second coating, the anesthetic concentration is at a higher ratio of polymer to anesthetic, e.g., a concentration at which the anesthetic is soluble in the polymer layer.

The top layer thus can serve to control the release of the drug in the bottom layer (aka depot layer) via the drug-polymer solubility ratio. Moreover, it is possible to alter the release rate of the drug by changing the thickness of the polymer layer and changing the polymer composition according to its water uptake. A polymer that absorbs a significant amount of water within 24 hours will release the contents of the depot layer rapidly. However, a polymer with limited water uptake or variable water uptake (changes as a function of its stage of degradation) will retard release of the water soluble anesthetic agent.

In one embodiment, the biodegradable polymer coating releases drug for at least 2-3 days. Such release is preferred, for example, when the drug is an analgesic to aide in localized pain management at the surgical site. To achieve an analgesic affect, the anesthetic and/or analgesic should be delivered to the injured tissue shortly after surgery or tissue injury.

In another embodiment, the coating comprises an anesthetic such that the anesthetic elutes from the implanted coated mesh to the surrounding tissue of the surgical site for between 1 and 10 days, which typically coincides with the period of acute surgical site pain. In another embodiment, delivery of an antimicrobial drug via a mesh of the invention can create an inhibition zone against bacterial growth and colonization surrounding the implant during the healing process (e.g., usually about 7-30 days or less) and/or prevent undue fibrotic responses.

Using biodegradable polymer coatings avoids the issue of drug solubility, impregnation or adherence in or to the underlying device since a coating having suitable chemical properties can be deposited onto the mesh pouch, optionally in concert with one or more drugs, to provide for the release of relatively high concentrations of those drugs over extended periods of time. For example, by modulating the chemical composition of the biodegradable polymer coating and the coating methodology, a clinically-efficacious amount of anesthetic drug can be loaded onto a mesh pouch to assure sufficient drug elution and to provide surgical site, post-operative pain relief for the patient.

Other elution profiles, with faster or slower drug release over a different (longer or shorter) times, can be achieved by altering the thickness of the layers, the amount of drug in the depot layer and the hydrophilicity of the biodegradable polymer.

Biodegradable Polymers

The coatings on the pouches of the invention are formed from biodegradable polymeric layers that optionally contain one or more drugs. Methods of making biodegradable polymers are well known in the art.

The biodegradable polymers suitable for use in the invention include but are not limited to:

polylactic acid, polyglycolic acid and copolymers and mixtures thereof such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL);

polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PHBT) and copolymers of polyhydroxybutyrate, poly(phosphazene), polyphosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol, polyalkylene oxides, hydroxypropylmethylcellulose, polysaccharides such as hyaluronic acid, chitosan and regenerate cellulose, and proteins such as gelatin and collagen, and mixtures and copolymers thereof, among others as well as PEG derivatives or blends of any of the foregoing.

In some embodiments, biodegradable polymers of the invention have diphenol monomer units that are copolymerized with an appropriate chemical moiety to form a polyarylate, a polycarbonate, a polyiminocarbonate, a polyphosphonate or any other polymer.

The preferred biodegradable polymers are tyrosine-based polyarylates including those described in U.S. Pat. Nos. 4,980,449; 5,099,060; 5,216,115; 5,317,077; 5,587,507; 5,658,995; 5,670,602; 6,048,521; 6,120,491; 6,319,492; 6,475,477; 6,602,497; 6,852,308; 7,056,493; RE37,160E; and RE37,795E; as well as those described in U.S. Patent Publication Nos. 2002/0151668; 2003/0138488; 2003/0216307; 2004/0254334; 2005/0165203; and those described in PCT Publication Nos. WO99/52962; WO 01/49249; WO 01/49311; WO 03/091337. These patents and publications also disclose other polymers containing tyrosine-derived diphenol monomer units or other diphenol monomer units, including polyarylates, polycarbonates, polyiminocarbonates, polythiocarbonates, polyphosphonates and polyethers.

Other biodegradable polymers suitable for use in the methods of the present invention include those described in U.S. application Ser. Nos. 12/499,399; 12/500,852; 12/564,736; 12/598,559; 12/641,996; as well as those described in U.S. Patent Publication No. 2009/0088548.

Likewise, the foregoing patents and publications describe methods for making these polymers, some methods of which may be applicable to synthesizing other biodegradable polymers. Finally, the foregoing patents and publications also describe blends and copolymers with polyalkylene oxides, including polyethylene glycol (PEG). All such polymers are contemplated for use in the present invention.

The representative structures for the foregoing polymers are provide in the above-cited patents and publications which are incorporated herein by reference.

As used herein, DTE is the diphenol monomer desaminotyrosyl-tyrosine ethyl ester; DTBn is the diphenol monomer desaminotyrosyl-tyrosine benzyl ester; DT is the corresponding free acid form, namely desaminotyrosyl-tyrosine. BTE is the diphenol monomer 4-hydroxy benzoic acid-tyrosyl ethyl ester; BT is the corresponding free acid form, namely 4-hydroxy benzoic acid-tyrosine.

P22 is a polyarylate copolymer produced by condensation of DTE with succinate. P22-10, P22-15, P22-20, P22-xx, etc., represents copolymers produced by condensation of (1) a mixture of DTE and DT using the indicated percentage of DT (i.e., 10, 15, 20 and xx % DT, etc.) with (2) succinate.

Additional preferred polyarylates are copolymers of desaminotyrosyl-tyrosine (DT) and an desaminotyrosyl-tyrosyl ester (DT ester), wherein the copolymer comprises from about 0.001% DT to about 80% DT and the ester moiety can be a branched or unbranched alkyl, alkylaryl, or alkylene ether group having up to 18 carbon atoms, any group of which can, optionally have a polyalkylene oxide therein. Similarly, another group of polyarylates are the same as the foregoing but the desaminotyrosyl moiety is replaced by a 4-hydroxybenzoyl moiety. Preferred DT or BT contents include those copolymers with from about 1% to about 30%, from about 5% to about 30% from about 10 to about 30% DT or BT. Preferred diacids (used informing the polyarylates) include succinate, glutarate and glycolic acid.

Additional biodegradable polymers useful for the present invention are the biodegradable, resorbable polyarylates and polycarbonates disclosed in U.S. provisional application Ser. No. 60/733,988, filed Nov. 3, 2005 and in its corresponding PCT Appln. No. PCT/US06/42944, filed Nov. 3, 2006. These polymers, include, but are not limited to, BTE glutarate, DTM glutarate, DT propylamide glutarate, DT glycineamide glutarate, BTE succinate, BTM succinate, BTE succinate PEG, BTM succinate PEG, DTM succinate PEG, DTM succinate, DT N-hydroxysuccinimide succinate, DT glucosamine succinate, DT glucosamine glutarate, DT PEG ester succinate, DT PEG amide succinate, DT PEG ester glutarate and DT PEG ester succinate.

The most preferred polyarylates are the DTE-DT succinate family of polymers, e.g., the P22-xx family of polymers having from 0-50%, 5-50%, 5-40%, 1-30% or 10-30% DT, including but not limited to, about 1, 2, 5, 10, 15, 20, 25, 27.5, 30, 35, 40%, 45% and 50% DT.

Additionally, the polyarylate polymers used in the present invention can have from 0.1-99.9% PEG diacid to promote the degradation process as described in U.S. provisional application Ser. No. 60/733,988. Blends of polyarylates or other biodegradable polymers with polyarylates are also preferred.

Drugs

Any drug, biological agent or active ingredient compatible with the process of preparing the mesh pouches of the invention can be incorporated into one or more layers of the biodegradable polymeric coatings on the mesh. Doses of such drugs and agents are know in the art. Those of skill in the art can readily determine the amount of a particular drug to include in the coatings on the meshes of the invention.

Examples of drugs suitable for use with the present invention include anesthetics, antibiotics (antimicrobials), anti-inflammatory agents, fibrosis-inhibiting agents, anti-scarring agents, leukotriene inhibitors/antagonists, cell growth inhibitors and the like. As used herein, "drugs" is used to include all types of therapeutic agents, whether small molecules or large molecules such as proteins, nucleic acids and the like. The drugs of the invention can be used alone or in combination.

Any pharmaceutically acceptable form of the drugs of the present invention can be employed in the present invention, e.g., the free base or a pharmaceutically acceptable salt or ester thereof. Pharmaceutically acceptable salts, for instance, include sulfate, lactate, acetate, stearate, hydrochloride, tartrate, maleate, citrate, phosphate and the like.

Examples of non-steroidal anti-inflammatories include, but are not limited to, naproxen, ketoprofen, ibuprofen as well as diclofenac; celecoxib; sulindac; diflunisal; piroxicam; indomethacin; etodolac; meloxicam; r-flurbiprofen; mefenamic; nabumetone; tolmetin, and sodium salts of each of the foregoing; ketorolac bromethamine; ketorolac bromethamine tromethamine; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their D, L, and racemic isomers); and the methyl, ethyl, propyl, isopropyl, n-butyl, sec-butyl, t-butyl, esters of acetylsalicylic acid.

Examples of anesthetics include, but are not limited to, lidocaine, bupivacaine, and mepivacaine. Further examples of analgesics, anesthetics and narcotics include, but are not limited to acetaminophen, clonidine, benzodiazepine, the benzodiazepine antagonist flumazenil, lidocaine, tramadol, carbamazepine, meperidine, zaleplon, trimipramine maleate, buprenorphine, nalbuphine, pentazocain, fentanyl, propoxyphene, hydromorphone, methadone, morphine, levorphanol, and hydrocodone. Local anesthetics have weak antibacterial properties and can play a dual role in the prevention of acute pain and infection.

Examples of antimicrobials include, but are not limited to, triclosan, chlorhexidine, rifampin, minocycline (or other tetracycline derivatives), vancomycin, daptomycin, gentamycin, cephalosporins and the like. In preferred embodiments the coatings contain rifampin and another antimicrobial agent, preferably that agent is a tetracycline derivative. In another preferred embodiment, the coatings contain a cephalosporin and another antimicrobial agent. Preferred combinations include rifampin and minocycline, rifampin and gentamycin, and rifampin and minocycline. As used herein, the term antibiotic and antibacterial can be used interchangeably with the term antimicrobial.

Further antimicrobials include aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts ethylsuccinate, and stearate forms thereof; clindamycin; clindamycin hydrochloride, sulfate, or phosphate salt; lincomycin and hydrochloride, sulfate, or phosphate salt thereof; tobramycin and its hydrochloride, sulfate, or phosphate salt; streptomycin and its hydrochloride, sulfate, or phosphate salt; vancomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; minocycline and its hydrochloride, sulfate, or phosphate salt; tetracycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; and clarithromycin.

Examples of antifungals include amphotericin B; pyrimethamine; flucytosine; caspofungin acetate; fluconazole; griseofulvin; terbinafin and its hydrochloride, sulfate, or phosphate salt; ketoconazole; micronazole; clotrimazole; econazole; ciclopirox; naftifine; and itraconazole.

Other drugs that can be incorporated into the coatings on the mesh pouches of the invention include, but are not limited to, keflex, acyclovir, cephradine, malphalen, procaine, ephedrine, adriamycin, daunomycin, plumbagin, atropine, quinine, digoxin, quinidine, biologically active peptides, cephradine, cephalothin, cis-hydroxy-L-proline, melphalan, penicillin V, aspirin, nicotinic acid, chemodeoxycholic acid, chlorambucil, paclitaxel, sirolimus, cyclosporins, 5-fluorouracil and the like.

Examples of anti-inflammatory compound include, but are not limited to, anecortive acetate; tetrahydrocortisol, 4,9(11)-pregnadien-17.alpha., 21-diol-3,20-dione and its -21-acetate salt; 11-epicortisol; 17.alpha.-hydroxyprogesterone; tetrahydrocortexolone; cortisona; cortisone acetate; hydrocortisone; hydrocortisone acetate; fludrocortisone; fludrocortisone acetate; fludrocortisone phosphate; prednisone; prednisolone; prednisolone sodium phosphate; methylprednisolone; methylprednisolone acetate; methylprednisolone, sodium succinate; triamcinolone; triamcinolone-16,21-diacetate; triamcinolone acetonide and its -21-acetate, -21-disodium phosphate, and -21-hemisuccinate forms; triamcinolone benetonide; triamcinolone hexacetonide; fluocinolone and fluocinolone acetate; dexamethasone and its -21-acetate, -21-(3,3-dimethylbutyrate), -21-phosphate disodium salt, -21-diethylaminoacetate, -21-isonicotinate, -21-dipropionate, and -21-palmitate forms; betamethasone and its -21-acetate, -21-adamantoate, -17-benzoate, -17,21-dipropionate, -17-valerate, and -21-phosphate disodium salts; beclomethasone; beclomethasone dipropionate; diflorasone; diflorasone diacetate; mometasone furoate; and acetazolamide.

Examples of leukotriene inhibitors/antagonists include, but are not limited to, leukotriene receptor antagonists such as acitazanolast, iralukast, montelukast, pranlukast, verlukast, zafirlukast, and zileuton.

Another useful drug that can be incorporated into the coatings of the invention is sodium 2-mercaptoethane sulfonate (Mesna). Mesna has been shown to diminish myofibroblast formation in animal studies of capsular contracture with breast implants [Ajmal et al. (2003) Plast. Reconstr. Surg. 112:1455-1461] and may thus act as an anti-fibrosis agent.

Those of ordinary skill in the art will appreciate that any of the foregoing disclosed drugs can be used in combination or mixture in coatings of the present invention.

Coating Methods

In accordance with the invention, one method to coat the mesh with a stiffening agent is to spray a solution of polymer to coat the filaments or fibers of the mesh to temporarily immobilize contact points of the filaments or fibers of said mesh. This method comprises (a) preparing a coating solution comprising a solvent and the stiffening agent; (b) spraying a mesh one or more times to provide an amount of solution on the mesh to produce a coating having a thickness and placement sufficient to temporarily immobilize contact points of the filaments or fibers of the mesh that coats filaments or fibers; and (c) drying the mesh to produce said coating. An example of ratio of coating thickness to polymer coating is shown in the scanning electron micrograph of FIG. 7. When used with a drug (or combination of drugs), the drug is included in the coating solution at the desired concentration.

Spraying can be accomplished by known methods. For example, the coating can be applied to the entire mesh or to that portion of the mesh necessary to stiffen it. One technique is to dip the mesh in the coating material; another is to push the mesh through rollers that transfer the coating on the mesh. Spraying the mesh with microdroplets is also effective. Techniques for selectively coating only those areas necessary to stiffen the mesh include deposition the coating through a template or mask that exposes only the desired areas of coverage for the coating, including dispensing the coating with micro needles or similar means. More preferably the coating can be applied using a photoresist-like mask that expose the desired portions, applying the coating over the photomask and the removing the photomask.

The coated meshes can be laser cut to produce the desired shaped and sized pouches, coverings and the like. The pouches can be shaped to fit relatively snugly or more loosely around the implantable medical device. Two pieces can be sealed, by heat, by ultrasound or other method known in the art, leaving one side open to permit insertion of the device at the time of the surgical procedure and to allow the leads or other wires to extend out of the pouch stick out/protrude.

Additionally, the mesh pouches of the invention have a space or opening sufficient to allow the leads from the device to pass through the pouch. The number of spaces or opening in the pouch that are provided can match the number and placement of the leads or other tubes extending from the CRM or other IMD, as applicable for the relevant device.

In preferred embodiments, the shape and size of the pouch of the invention is similar to that of the CRM or IMD with which it is being used, and the pouch has a sufficient number of openings or spaces to accommodate the leads or tubing of the particular CRM or other IMD.

The pouches of the invention are porous from the mesh but can have additional porosity. For example, additional porosity can be imparted by laser cutting additional holes in the coated mesh porous pouches. Hence, the pouch need not completely encase or surround the IMD. An IMD is thus substantially encapsulated, encased, surrounded or covered when the pouch can hold the device and at least 20%, 30%, 50%, 60%, 75%, 80%, 85%, 90%, 95% or 98% of the device is within the pouch. Porous pouches and partially encased pouches permit contact with tissue and body fluids and are particularly useful with monopole CRM or other IMD devices. Porosity will contribute to the percentage of the IMD covered by the pouch. That is, an IMD is considered to be 50% covered if it is completely surrounded by a pouch that is constructed of a film with 50% voids or holes.

CRMs and Other IMDs

The CRMs and other IMDs used with the pouches of the invention include but are not limited to pacemakers, defibrillators, implantable access systems, neurostimulators, other stimulation devices, ventricular assist devices, infusion pumps or other implantable devices (or implantable components thereof) for delivering medication, hydrating solutions or other fluids, intrathecal delivery systems, pain pumps, or any other implantable system to provide drugs or electrical stimulation to a body part.

Implantable cardiac rhythm management devices (CRMs) are a form of IMDs and are life-long medical device implants. CRMs ensure the heart continually beats at a steady rate. There are two main types of CRM devices: implantable cardiac rhythm management devices and implantable defibrillators.

The ICDs, or implantable cardioverter defibrillator, and pacemakers share common elements. They are permanent implants inserted through relatively minor surgical procedures. Each has 2 basic components: a generator and a lead. The generator is usually placed in a subcutaneous pocket below the skin of the breastbone and the lead is threaded down and into the heart muscle or ventricle. The common elements of placement and design result in shared morbidities, including lead extrusion, lead-tip fibrosis, and infection. Although infection rates are purportedly quite low, infection is a serious problem as any bacterial contamination of the lead, generator, or surgical site can travel directly to the heart via bacterial spreading along the generator and leads. Endocarditis, or an infection of the heart, has reported mortality rates as high as 33%.

An ICD is an electronic device that constantly monitors heart rate and rhythm. When it detects a fast, abnormal heart rhythm, it delivers energy to the heart muscle. This action causes the heart to beat in a normal rhythm again in an attempt to return it to a sinus rhythm.

The ICD has two parts: the lead(s) and a pulse generator. The lead(s) monitor the heart rhythm and deliver energy used for pacing and/or defibrillation (see below for definitions). The lead(s) are directly connected to the heart and the generator. The generator houses the battery and a tiny computer. Energy is stored in the battery until it is needed. The computer receives information on cardiac function via the leads and reacts to that information on the basis of its programming.

The different types of ICDs include, but are not limited to, single chamber ICDs in which a lead is attached in the right ventricle. If needed, energy is delivered to the ventricle to help it contract normally; dual chamber ICDs in which the leads are attached in the right atrium and the right ventricle. Energy is delivered first to the right atrium and then to the right ventricle to ensure that the heart beats in a normal sequence; and biventricular ICDs in which leads are attached in the right atrium, the right ventricle and the left ventricle. a variety of manufacturers (see Table 1). Sizes of the CRMs vary and typically size ranges are listed in Table 1.

TABLE 1

CRM Devices

| Manufacturer | Device | Type | Model | Size (H" × L" × W") |
|---|---|---|---|---|
| Medtronic | EnPulse Pacing system | Pacing system | E2DRO1 | 1.75 × 2 × 0.33 |
| Medtronic | EnPulse Pacing system | Pacing system | E2DR21 | 1.75 × 1.63 × 0.33 |
| Medtronic | EnRhythm Pacing system | Pacing system | P1501DR | 1.77 × 2 × 0.31 |
| Medtronic | AT500 Pacing system | Pacing system | AT501 | 1.75 × 2.38 × 0.33 |
| Medtronic | Kappa DR900 & 700 series | Pacing system | DR900, DR700 | 1.75-2 × 1.75-2 × 0.33 |
| Medtronic | Kappa DR900 & 700 series | Pacing system | SR900, SR700 | 1.5-1.75 × 1.75-2 × 0.33 |
| Medtronic | Sigma | Pacing system | D300, D200, D303, D203 | 1.75 × 2 × 0.33 |
| Medtronic | Sigma | Pacing system | DR300, DR200, DR303, DR306, DR203 | 1.75-2 × 2 × 0.33 |
| Medtronic | Sigma | Pacing system | VDD300, VDD303 | 1.75 × 1.75 × 0.33 |
| Medtronic | Sigma | Pacing system | S300, S200, S100, S303, S203, S103, S106, VVI-103 | 1.63 × 2 × 0.33 |
| Medtronic | Sigma SR | Pacing system | SR300, S200, SR303, SR306, SR203 | 1.63 × 2 × 0.33 |
| Medtronic | Entrust | Defibrillator | D154VRC 35J | 2.44 × 2 × 0.6 |
| Medtronic | Maximo & Marquis family | Defibrillator | | Size of a pager |
| Medtronic | Gem family | Defibrillator | III T, III R, III R, II R, II VR | Size of a pager |
| Guidant | Contak Renewal TR | Pacing system | H120, H125 | 2.13 × 1.77 × 033 |
| St. Jude | Identity | Pacing system | ADx DR, ADx SR, ADx XL, ADx VDR | 1.6-1.73 × 1.73-2.05 × 0.24 |
| St. Jude | Integrity | Pacing system | ADx DR, ADx SR | 1.6-1.73 × 1.73-2.05 × 0.24 |

This arrangement helps the heart beat in a more balanced way and is specifically used for patients with heart failure.

A pacemaker is a small device that sends electrical impulses to the heart muscle to maintain a suitable heart rate and rhythm. A pacemaker can also be used to treat fainting spells (syncope), congestive heart failure, and hypertrophic cardiomyopathy. Pacemakers are generally implanted under the skin of the chest during a minor surgical procedure. The pacemaker is also comprised of leads and a battery-driven pulse generator. The pulse generator resides under the skin of the chest. The leads are wires that are threaded through the veins into the heart and implanted into the heart muscle. They send impulses from the pulse generator to the heart muscle, as well as sense the heart's electrical activity.

Each impulse causes the heart to contract. The pacemaker may have one to three leads, depending on the type of pacemaker needed to treat your heart problem.

The different types of pacemakers include, but are not limited to single chamber pacemakers which use one lead in the upper chambers (atria) or lower chambers (ventricles) of the heart; dual chamber pacemakers which use one lead in the atria and one lead in the ventricles of your heart; and biventricular pacemakers which use three leads: one placed in the right atrium, one placed in the right ventricle, and one placed in the left ventricle (via the coronary sinus vein).

The pouches of the invention can thus be designed to fit a wide range of pacemakers and implantable defibrillators from Implantable neurostimulators are similar to pacemakers in that the devices generate electrical impulses. These devices send electrical signals via leads to the spine and brain to treat pain and other neurological disorders. For example, when the leads are implanted in the spine, the neurostimulation can be used to treat chronic pain (especially back and spinal pain); when the leads are implanted in the brain, the neurostimulation can be used to treat epilepsy and essential tremor including the tremors associated with Parkinson's disease and other neurological disorders. Neurostimulation can be used to treat severe, chronic nausea and vomiting as well as urological disorders. For the former, electrical impulses are sent to the stomach; for the latter, the electrical impulses are sent to the sacral nerves in the lower back. The implant location of theneurostimulator varies by application but, in all cases, is placed under the skin and is susceptible to infection at the time of implantation and post-implantation. Likewise, reintervention and replacement of batteries in the neurostimulators can occur at regular intervals.

The pouches of the invention can thus be designed to fit a wide range of neurostimulators from a variety of manufacturers (see Table 2). Sizes of the neurostimulators vary and typically size ranges are listed in Table 2.

TABLE 2

Neurostimulators

| Manufacturer | Device | Type | Model | Size (H" × L" × W") |
|---|---|---|---|---|
| Medtronic | InterStim INS | Neurostimulation | 3023 | 2.17 × 2.4 × 0.39 |
| Medtronic | InterStim INS II | Neurostimulation | 3058 | 1.7 × 2.0 × 0.3 |
| Medtronic | RESTORE | Neurostimulation | 37711 | 2.56 × 1.93 × 0.6 |
| Advanced Bionics (Boston Scientific) | Precision IPG | Neurostimulation/Spinal Cord Stimulator | | 2.09 × 1.70 × 0.35 |
| Cyberonics | VNS Therapy system | Neurostimulation/Epilepsy | 102 | 2.03 × 2.06 × 0.27 |
| Cyberonics | VNS Therapy system | Neurostimulation/Epilepsy | 102R | 2.03 × 2.32 × 0.27 |
| ANS (St. Jude) | Eon | Neurostimulation | | Comparable to Medtronic Restore |
| ANS (St. Jude) | Genesis RC | Neurostimulation | | Comparable to Medtronic Restore |
| ANS (St. Jude) | Genesis XP | Neurostimulation | | Comparable to Medtronic Restore |

Reported infection rates for first implantation are usually quite low (less than 1%); however, they increase dramatically when a reintervention is necessary. Reintervention often requires the removal of the generator portion of the ICD, pacemaker, neurostimulator, drug pump or other IMD and having a resorbable pouch enhances that process.

Other IMDs for use in the invention are drug pumps, especially pain pumps and intrathecal delivery systems. These devices generally consist of an implantable drug pump and a catheter for dispensing the drug. The implantable drug pump is similar in size to the neurostimulators and CRMs. Further implantable medical devices include, but are not limited to, implantable EGM monitors, implantable access systems, or any other implantable system that utilizes battery power to provide drugs or electrical stimulation to a body part.

Antimicrobial Efficacy

Antimicrobial efficacy of the pouches of the invention can be demonstrated in laboratory (in vitro), for example, using the modified Kirby—Bauer Antibiotic Susceptibility Test (Disk Diffusion Test) (in vitro) to assess bacterial zones of inhibitions or by the Boburden Test Method (in vitro). In such experiments, a small disk of the pouch is cut and used. Antimicrobial efficacy can also be demonstrated in vivo using animal models of infection. For example, a pouch and device combination are implanted in an animal, the surgical site is deliberately infected with a pathogenic microorganism, such as *Staphylococcus aureus* or *Staphylococcus epidermis*, and the animal is monitored for signs of infection and inflammation. At sacrifice, the animal is assessed for inflammation, fibrosis and bacterial colonization of the pouch, device and the surrounding tissues.

Prevention and/or Retardation of Biofilm Formation

In Vitro Model

In the in vitro study, the efficacy of the antibacterial pouch in preventing or retarding the formation of biofilms was assessed using a Center for Disease Control bioreactor model and confirmed by Scanning Electron Microscopy.

In Vivo Model

A reproducible and quantitative model of device infection is used in determining the efficacy of these types of products. The rabbit is frequently chosen for implant studies, and its size (at 2.5 kg or greater) can accommodate up to two subcutaneous implants the size of a typical pacing device. The two-layer closure of the pocket, along with a separate incision site for bacterial inoculation, assures containment of the infection to the pocket with no observable cross-contamination to the contralateral pocket nor the implant insertion site. Examination of the explanted devices in the absence of the pouch indicates the successful development of an infection as evidenced by positive bacterial cultures of the pocket and the device as well as the presence of pus in many cases. In addition, a biofilm-like material is present on the device. The ability to sample the explanted device and pocket by the multiple swabbing technique assures a thorough sampling of all devices areas, and the additional vortex/sonication process allows additional sampling of adherent bacteria in a quantitative manner that would allow demonstration of log-reduction of the number of bacteria present.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety.

Example 1

Antibiotic Release from DTE-DT Succinate Coated Mesh

A. Preparation of Mesh by Spray-Coating

A 1% solution containing a ratio of 1:1:8 rifampin:minocycline:polymer in 9:1 tetrahydrofuran:methanol was spray-coated onto a surgical mesh by repeatedly passing the spray nozzle over each side of the mesh until each side was coated with at least 10 mg of antimicrobial-embedded polymer. Samples were dried for at least 72 hours in a vacuum oven before use.

The polymers are the polyarylates P22-xx having xx being the % DT indicated in Table 3. In Table 3, Rxx or Mxx indicates the percentage by weight of rifampin (R) or minocycline (M) in the coating, i.e., R10M10 means 10% rifampin and 10% minocycline hydrochloride with 80% of the indicated polymer. Table 3 provides a list of these polyarylates with their % DT content, exact sample sizes, final coating weights and drug coating weights.

TABLE 3

Polyarylate Coated Meshes with Rifampin and Minocycline HCl

| Sample No. | Coating Parameters (No. Spray Passes) | | Avg. Coating Wt. per 116 cm$^2$ (mg) | Coating Wt. per cm$^2$ (mg) | Rifampin (μg) | Minocycline HCl (μg) |
|---|---|---|---|---|---|---|
| 1 | P22-25 (20) | R10M10 | 100 | 0.86 | 86 | 86 |
| 2 | P22-25 (40) | R10M10 | 150 | 1.29 | 129 | 129 |
| 3 | P22-25 (80) | R10M10 | 200 | 1.72 | 172 | 172 |
| 4 | P22-27.5 (1) | R10M10 | 20 | 0.17 | 17 | 17 |
| 5 | P22-27.5 (2) | R10M10 | 40 | 0.34 | 34 | 34 |
| 6 | P22-27.5 (3) | R10M10 | 60 | 0.52 | 52 | 52 |

B. Zone of Inhibition (ZOI) Studies

The ZOI for antibiotic coated meshes was determined according to the Kirby-Bauer method. *Staphylococcus epidermidis* or *Staphylococcus aureus* were inoculated into Triplicate Soy Broth (TSB) from a stock culture and incubated at 37° C. until the turbidity reached McFarland #0.5 standard (1-2 hours). Plates were prepared by streaking the bacteria onto on Mueller-Hinton II agar (MHA) three times, each time swabbing the plate from left to right to cover the entire plate and rotating the plate between swabbing to change direction of the streaks.

A pre-cut piece (1-2 cm$^2$) of spray-coated mesh was firmly pressed into the center of pre-warmed Mueller Hinton II agar plates and incubated at 37° C. Pieces were transferred every 24 h to fresh, pre-warmed Mger Hinton II agar plates using sterile forceps. The distance from the sample to the outer edge of the inhibition zone was measured every 24 h and is reported on the bottom row in Table 4 and 5 for each sample. The top row for each sample represents difference between the diameter of the ZOI and the diagonal of the mesh. Table 4 shows the ZOI results for meshes placed on *S. epidermidis* lawns and Table 5 show s the ZOI results for meshes placed on *S. aureus* lawns. Additionally, three pieces were removed every 24 h for analysis of residual minocycline and rifampin.

FIG. 1 shows the total ZOI on *S. aureus* for meshes with 10% each of minocycline hydrochloride and rifampin in a DTE-DT succinate polyarylate coating having 25% or 27.5% DT. The catheter is a COOK SPECTRUM venous catheter impregnated with rifampin and minocycline hydrochloride.

TABLE 4

*S. epidermidis* ZOI

| Sample No. | Coating Parameters | | Day 1 (mm) | Day 2 (mm) | Day 3 (mm) | Day 4 (mm) | Day 6 (mm) | Day 7 (mm) |
|---|---|---|---|---|---|---|---|---|
| 1 | P22-25 | R10M10 | 18.65 | 31.70 | 33.04 | 29.63 | 25.43 | 15.66 |
|   |        |        | 31.30 | 44.36 | 45.70 | 42.29 | 38.08 | 28.31 |
| 2 | P22-25 | R10M10 | 19.28 | 30.59 | 33.67 | 31.74 | 0.60  | 8.56  |
|   |        |        | 32.10 | 43.45 | 46.53 | 44.60 | 13.45 | 21.42 |
| 3 | P22-25 | R10M10 | 26.59 | 34.70 | 30.31 | 31.75 | 23.65 | 17.29 |
|   |        |        | 39.48 | 47.59 | 43.20 | 46.16 | 36.54 | 30.18 |
| 4 | P22-27.5 | R10M10 | 18.33 | 31.58 | 35.25 | 30.45 | 2.08  | 6.72  |
|   |          |        | 31.06 | 44.31 | 47.98 | 43.18 | 14.81 | 19.45 |
| 5 | P22-27.5 | R10M10 | 17.48 | 32.81 | 33.68 | 28.06 | 7.89  | 12.86 |
|   |          |        | 30.17 | 45.51 | 46.38 | 40.76 | 20.59 | 25.56 |
| 6 | P22-27.5 | R10M10 | 31.73 | 29.81 | 35.03 | 24.99 | 12.55 | 16.22 |
|   |          |        | 44.42 | 42.50 | 47.72 | 37.68 | 25.24 | 28.91 |

TABLE 5

*S. aureus* ZOI

| Sample No. | Coating Parameters | | Day 1 (mm) | Day 2 (mm) | Day 3 (mm) | Day 4 (mm) | Day 5 (mm) | Day 7 (mm) |
|---|---|---|---|---|---|---|---|---|
| 1 | P22-25 | R10M10 | 12.75 | 17.90 | 18.22 | 22.44 | 12.35 | 11.94 |
|   |        |        | 25.84 | 30.66 | 30.97 | 35.20 | 25.11 | 24.69 |
| 2 | P22-25 | R10M10 | 14.23 | 11.28 | 20.04 | 28.24 | 16.31 | 10.35 |
|   |        |        | 26.90 | 23.94 | 32.71 | 40.91 | 28.98 | 23.02 |
| 3 | P22-25 | R10M10 | 17.87 | 21.52 | 23.45 | 25.36 | 17.42 | 14.72 |
|   |        |        | 30.57 | 34.22 | 36.15 | 36.02 | 30.12 | 27.42 |
| 4 | P22-27.5 | R10M10 | 9.77  | 19.02 | 19.06 | 23.01 | 13.81 | 5.61  |
|   |          |        | 22.76 | 32.01 | 32.05 | 36.00 | 26.80 | 18.6  |
| 5 | P22-27.5 | R10M10 | 9.70  | 21.77 | 19.55 | 24.00 | 11.84 | 3.89  |
|   |          |        | 22.30 | 34.36 | 35.48 | 36.60 | 24.44 | 16.49 |

TABLE 5-continued

S. aureus ZOI

| Sample No. | Coating Parameters | | Day 1 (mm) | Day 2 (mm) | Day 3 (mm) | Day 4 (mm) | Day 5 (mm) | Day 7 (mm) |
|---|---|---|---|---|---|---|---|---|
| 6 | P22-27.5 | R10M10 | 20.92 | 21.29 | 22.40 | 24.27 | 11.06 | 4.99 |
| | | | 33.68 | 34.05 | 35.15 | 37.02 | 23.82 | 17.75 |

Table 6 shows that the duration of in vitro drug release increases with the hydrophilicity of the resorbable polymer. Solvent cast films were soaked in PBS and antibiotic release was monitored by HPLC.

TABLE 6

Antibiotic Release as a Function of Polymer Hydrophilicity

| Films | | Days releasing Rifampin | Days releasing MinocyclineHCl |
|---|---|---|---|
| P22-15 | R10M10 | 32 | 32 |
| P22-20 | R10M10 | 25 | 25 |
| P22-25 | R10M10 | 7 | 7 |
| P22-27.5 | R10M10 | 10 | 10 |
| P22-30 | R10M10 | 4 | 4 |

Example 2

Bupivacaine Release from DTE-DT Succinate Coated Mesh

A. Preparation of Mesh

Figure 2:
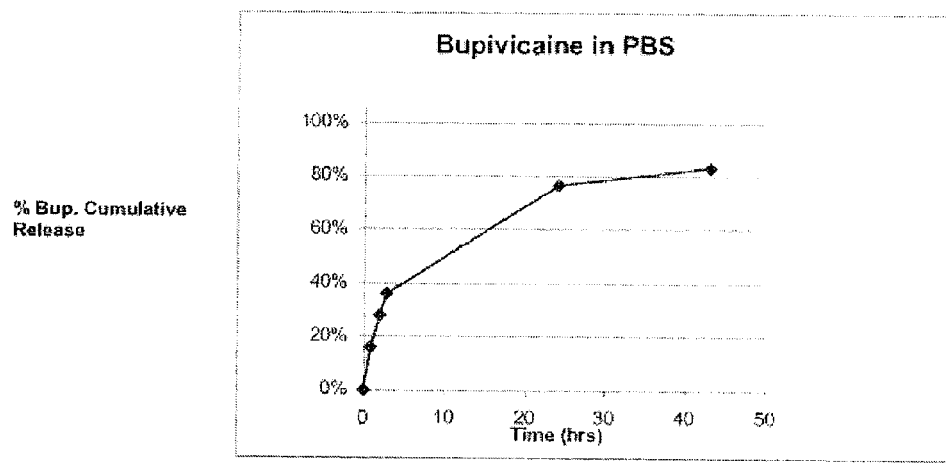
FIG. 2 graphically depicts cumulative bupivacaine release from multilayer polyarylate-coated meshes.

For the experiment shown in FIG. 2, a first depot coating containing 540 mg of bupivacaine HCl as a 4% solution with 1% P22-27.5 polyarylate in a mixture of THF Methanol was spray coated onto a mesh. A second layer consisting of 425 mg of the same polyarylate alone was deposited on top of the first layer.

Figure 3:
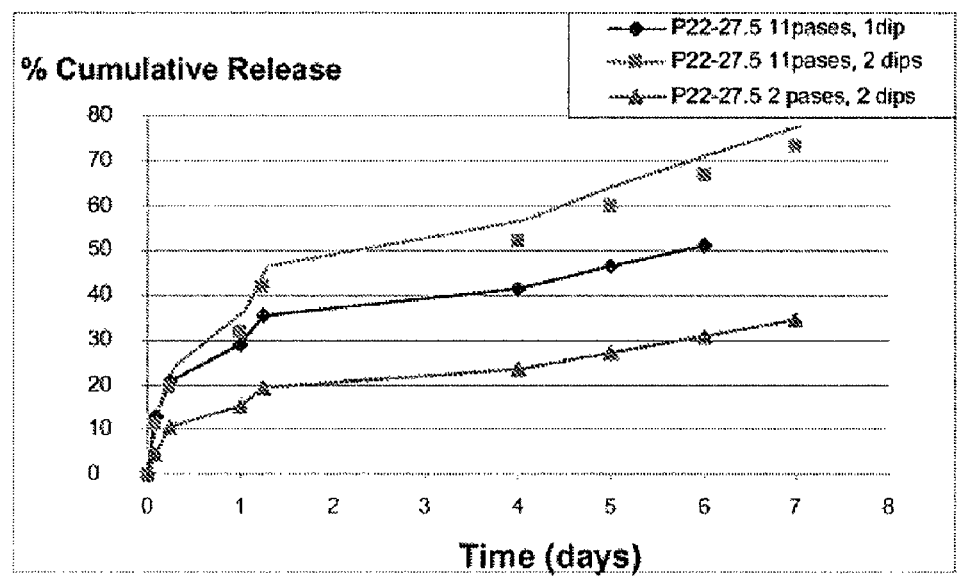
FIG. 3 graphically depicts cumulative bupivacaine release from multilayer polyarylate-coated meshes having various loadings of bupivacaine. The symbols represent the following meshes: ♦, P22-27.5 (11 passes, 1 dip); ■, P22-27.5 (11 passes, 2 dips); and ▲, P22-27.5 (2 passes, 2 dips).

For the experiment shown in FIG. 3, a solution of approximately 4% bupivacaine in DTE-DT succinate polymer having 27.5% DT was sprayed onto a mesh using the indicted number of passes followed by the indicated number of dips into a solution of the same polyarylate in THF:Methanol (9:1)

B. Anesthetic Release

Pre-weighed pieces of mesh were placed in PBS at 37° C. and a sample withdrawn periodically for determination of bupivacaine by HPLC. FIG. 2 shows the cumulative release of bupivacaine into PBS from the multilayer polyarylate coating as a function of time. Nearly 80% of the bupivacaine had been released after 25 hours of incubation.

FIG. 3 is an example of the changes in release characteristics that can be achieved by altering both the amount of drug in the depot layer and the thickness of the outer layer. These coated surgical meshes are much stiffer than their uncoated counterparts.

Example 3

In Vivo Bupivacaine Release from DTE-DT Succinate Coated Meshes

A. Overview

Rats with jugular cannulas for pharmacokinetic studies were surgically implanted with a 1×2 cm P22-27.5 polyarylate-coated mesh containing 7.5 mg of bupivacaine/cm$^2$. Before surgery, baseline pin-prick responses to nociception were measured at the planned surgical incision site, and baseline blood samples were obtained. A hernia was created by incision into the peritoneal cavity during via subcostal laparotomy, and a Lichtenstein non-tension repair was performed using the bupivacaine-impregnated polyarylate-coated mesh. Blood samples were drawn at 3, 6, 24, 48, 72, 96, and 120 hours after implantation. Prior to drawing blood, the rats were subjected to a pin prick test to assess dermal anesthesia from bupivacaine release. The behavioral results indicate that moderate levels of dermal anesthesia appeared from 3 to 120 hours, with the amount at 6 and 48 hours significantly above baseline ($p<0.05$). Pharmacokinetic analysis indicates that the plasma bupivacaine levels fit a one-compartment model with first-order absorption from 0 to 24 hours.

B. Preparation of Surgical Mesh

A polypropylene mesh was spray coated as described in the first paragraph of Example 2. Individual meshes were cut to 1×2 cm, individually packaged, and sterilized by gamma irradiation. The mesh was loaded with 7.5 mg/cm$^2$ of bupivacaine HCl for a total of 15 mg of bupivacaine loaded per 1×2 cm mesh.

C. Surgical Implantation of Mesh

Eight male rats, 59-63 days old and weighing from 250-275 g, were obtained from Taconic Laboratory (Germantown, N.Y.) with an external jugular cannula (SU007). Each rat was anesthetized with isoflurane to a plane of surgical anesthesia, as determined by the absence of a response to toe pinch and corneal reflex and maintained at 2% isoflurane during surgery. The subcostal site was shaved, washed with 10% providone iodine and rinsed with 70% ethanol. Sterile drapes were used to maintain an aseptic surgical field, and sterilized instruments were re-sterilized between rats using a hot-bead sterilizer. A 2.5 cm skin incision was made 0.5 cm caudal to and parallel to the last rib. The underlying subcutaneous space (1 cm on both sides of the incision) was loosened to accommodate the mesh. A 2 cm incision was made through the muscle layers along the same plane as the skin incision, penetrating the peritoneal cavity and the peritoneum was closed with 6-0 Prolene sutures in a continuous suture pattern. Rather than suturing the inner and outer oblique muscles using the classic "tension closure," a Lichtenstein "non-tension" repair was undertaken using the mesh as the repair material. The mesh prepared in Section A was positioned over the incisional hernia, and sutured into the internal and external oblique muscles using 6-0 Prolene sutures. The subcutaneous tissue was then sutured in a continuous pattern with 6 to 8 6-0 Prolene sutures to prevent the rats from accessing the mesh, followed by 6 to 8 skin sutures. Total surgical time was 10 min for anesthetic induction and preparation and 20 min for the surgery.

The rats were allowed to recover in their home cages, and monitored post-surgically until they awoke. Blood samples were drawn for determination of plasma bupivacaine levels at 3, 6, 24, 48, 72, 96, and 120 hours after surgery. The rats were assessed for guarding the incision, and the incision was assessed for signs of inflammation, swelling or other signs of infection. No rats exhibited toxicity or seizures, or were in a moribund state from infection or the release of bupivacaine.

D. Dermal Anesthetic Tests

The nociceptive pin prick test was used to assess dermal anesthesia (Morrow and Casey, 1983; Kramer et al., 1996; Haynes et al., 2000; Khodorova and Strichartz, 2000). Holding the rat in one hand, the other hand was used to apply the pin. Nociception was indicated by a skin-flinch or by a nocifensive (i.e., startle or attempt to escape) response from the rat. While the presence of the mesh interfered with the skin flinch response, nocifensive response remained completely intact.

Figure 4:
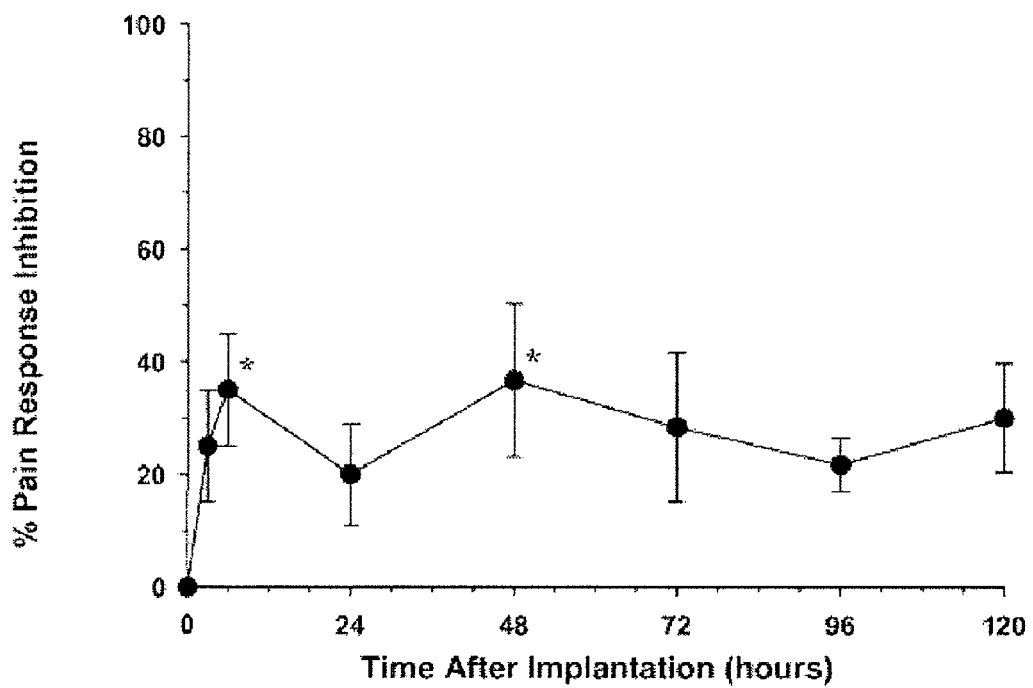
FIG. 4 graphically depicts the time course of dermal anesthesia from 1×2 cm surgically implanted, polyarylate meshes containing 7.5 mg/cm$^2$ bupivacaine. Meshes were implanted in rats by subcostal laparotomy; pin-prick responses were determined and are shown as % pain response inhibition (see Examples for details). The "*" indicates statistically significant response at $p<0.05$ compared to the baseline pin-prick response.
Figure 5:
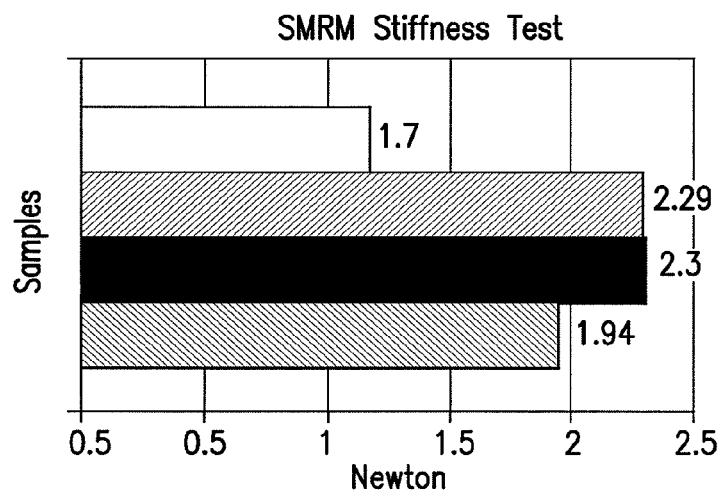
FIG. 5 graphically depicts mesh stiffness. The bars, from top to bottom, represent the stiffness for (1) a PPM3 mesh without a polyarylate coating and without sterilization, (2) a Prolene™ (Ethicon) mesh sterilized with ethylene oxide, (3) a polyarylate-coated PPM3 mesh 12 months after coating and sterilized by gamma irradiation with a nitrogen flush, and (4) a polyarylate-coated PPM3 mesh 12 months after coating and sterilized by gamma irradiation.

Baseline nocifensive responses to 10 applications of the pin from a Buck neurological hammer were obtained at the planned incision site prior to mesh implantation. After surgery, the pin prick test was applied rostral to the incision. The nerves caudal to the incision were transected during the procedure, and therefore did not respond to pin application and were not tested. The post-implantation test was repeated using the same force as before surgery and with 10 pin applications, and the percent inhibition of nocifensive responding was calculated by: [1−(test responses/10 base responses)]× 100. The data was analyzed using repeated measures ANOVA followed by post hoc analysis using the Tukey's test. The results are shown in FIG. 4.

Example 4

Mesh Stiffness

A. Meshes prepared as described in Example 1 were subject to stiffness testing according to the method of TyRx Pharma Inc. Mesh Stiffness Test Protocol, ATM 0410, based on ASTM 4032-94. Meshes were sealed in foil bags before sterilization using gamma irradiation. Where indicated by "Gamma $N_2$", the bags were flushed with nitrogen before sealing and irradiation. Meshes were tested in triplicate. The results are shown in Table 7 and indicate that aging does not affect the flexibility of the coated meshes.

TABLE 7

Stiffness Testing

| Mesh | Sample 1 (Newtons) | Sample 2 (Newtons) | Sample 3 (Newtons) | Average (Newtons) | t-test |
|---|---|---|---|---|---|
| PPM3, Gamma, 12 month aged coating | 1.84 | 2.36 | 1.62 | 1.94 | 0.016 |
| PPM3, Gamma N2 flush, 12 month aged coating | 2.2 | 2.24 | 2.56 | 2.3 | 0.014 |
| Prolene, Ethylene oxide sterilization | 2.78 | 2.16 | 1.94 | 2.29 | 0.019 |
| PPM3, No Sterilization, No Coating | 1.2 | 1.3 | 1 | 1.17 | |

Figure 6:
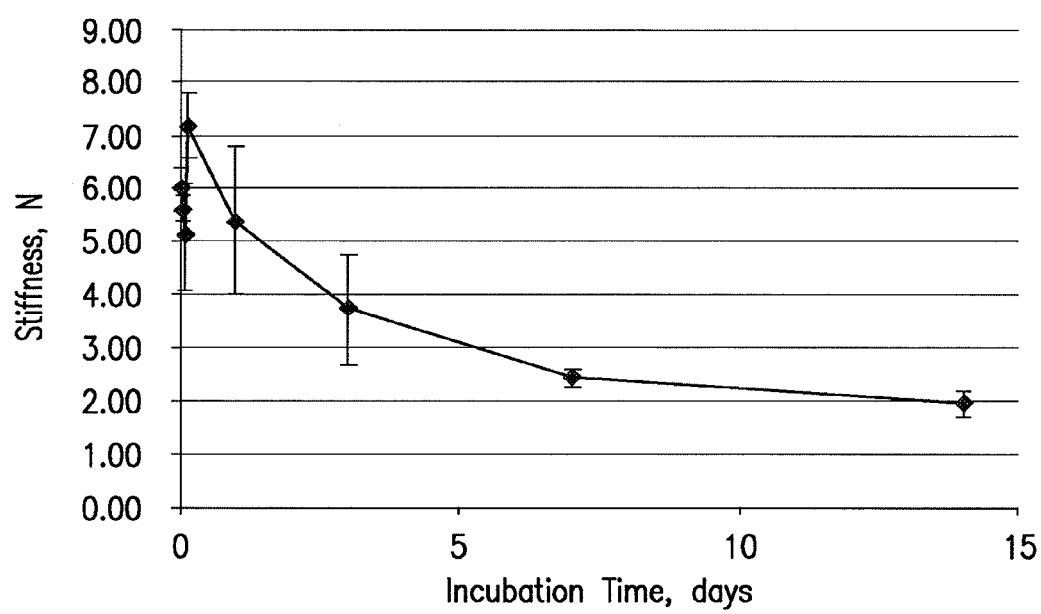
FIG. 6 graphically depicts the change in mesh stiffness over time during the course of polymer degradation for a polymer-coated polypropylene mesh soaking in PBS.

B. Meshes were prepared by spray coating a solution of P22-27.5 onto a PPM3 mesh as generally described in Example 1. The coated meshes were cut into 3" by 3" squares to provide 80 mg polymer coating per square. The squares were incubated in 1 L of 0.01 M PBS for the indicated times then removed for stiffness testing as described in part A of this Example. All experiments were done in triplicate. As a control, non-coated PPM3 meshes were incubated under the same conditions. The stiffness of the control when dry was 1.42±0.23 N when dry and 1.12 N after both 1 hour and 24 hour in 0.01 M PBS. The results are shown in FIG. 6.

Example 5
Micrographs of Coated Meshes

Figure 7:
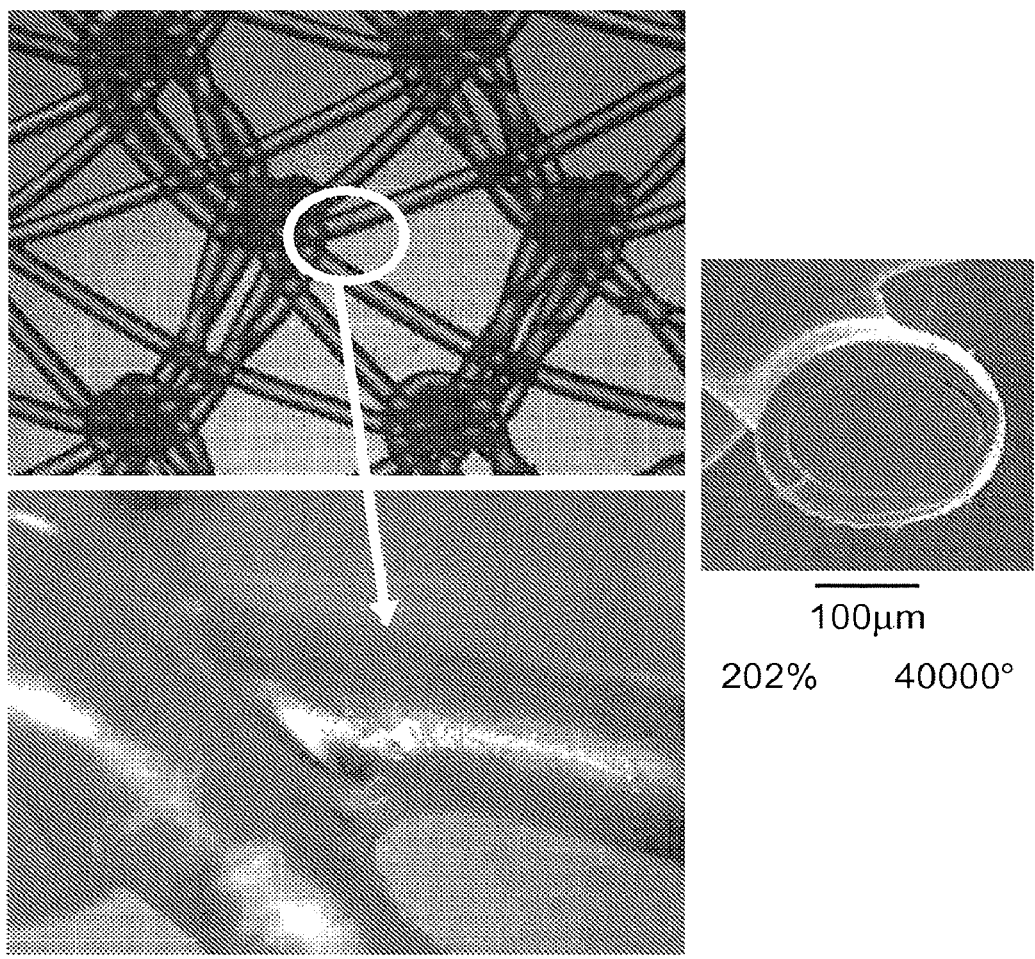
FIG. 7 depicts micrographs of a tyrosine polyarylate-coated mesh. The top left panel shows the woven nature of the mesh and the contact points of the filaments. The bottom left panel demonstrates the coating over the contact points of the mesh filaments. The right panel is a scanning electron micrograph of a coated filament.

A tyrosine polyarylate-coated mesh without antibiotics, i.e., only a polymer coating, was prepared as described in Example 1 and omitting the antibiotics in the spray coating solution. An optical image of the coated mesh is shown in the top left panel of FIG. 7 at a magnification that readily shows the woven nature of the mesh and the contact points of the filaments. A close up of a contact point is shown in the bottom left panel of FIG. 7 and demonstrates that the coating immobilizes the contact points of the mesh filaments. The right panel of FIG. 7 is a scanning electron micrograph of a coated filament.

Figure 8:
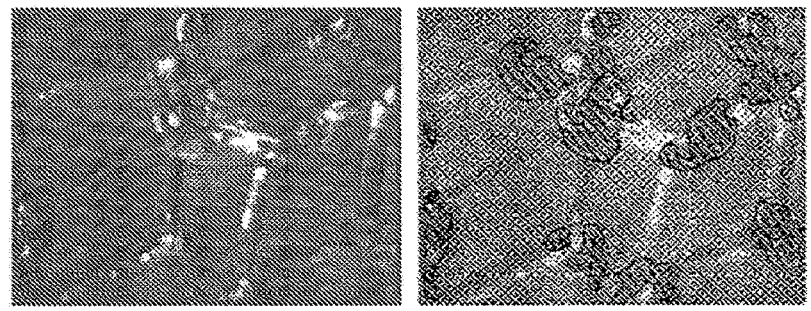
FIG. 8 provides an optical image of a mesh having a tyrosine polyarylate coating containing rifampin and minocycline. On the left, the optical image; on the right, a schematic thereof indicating the areas of intense orange color by the circled areas filled with diagonal lines.

FIG. 8 shows an optical image of a mesh from Example 1, i.e., coated with polymer, rifampin and minocycline. In color, this photograph shows the mesh on a blue background with the filaments appearing greenish with some orange and the knots (or filament contact points) appearing mostly solid orange. The orange color is due to the antibiotics and is more visible on the knots due to the greater surface area of the mesh in that region. The color differentiation is difficult to visualize in the black and white version of this photograph so on the right panel the areas of orange are indicated by circled areas filled with diagonal lines.

Example 6

Antimicrobial, Coated Mesh, Pacemaker Pouch

Figure 9:
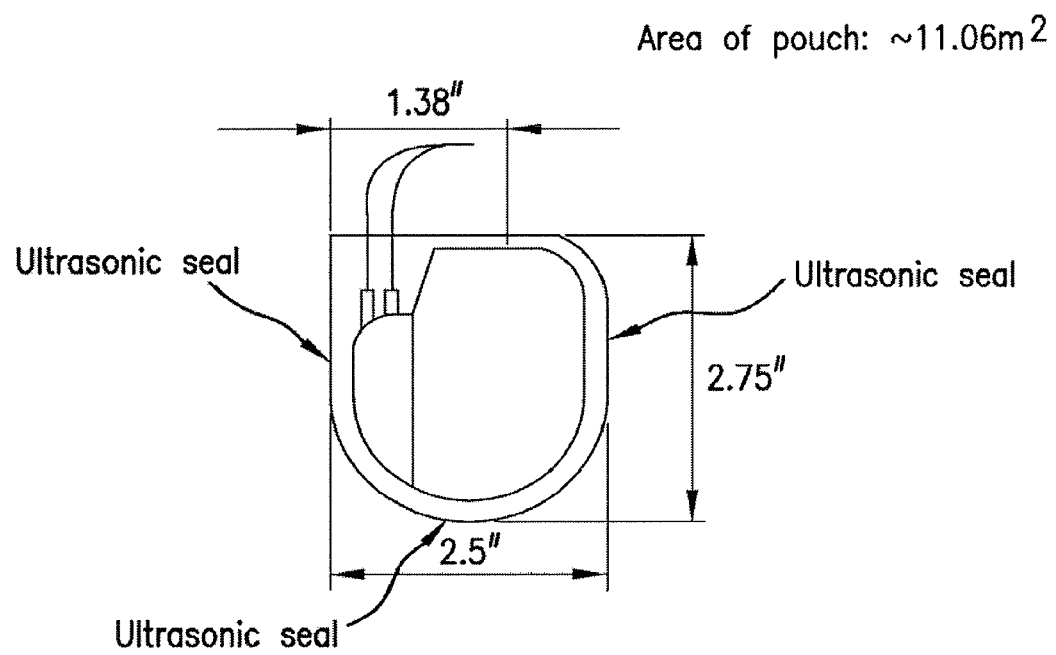
FIG. 9 shows a schematic diagram of a polymer-coated CRM pouch with the CRM inserted in the pouch.
Figure 10:
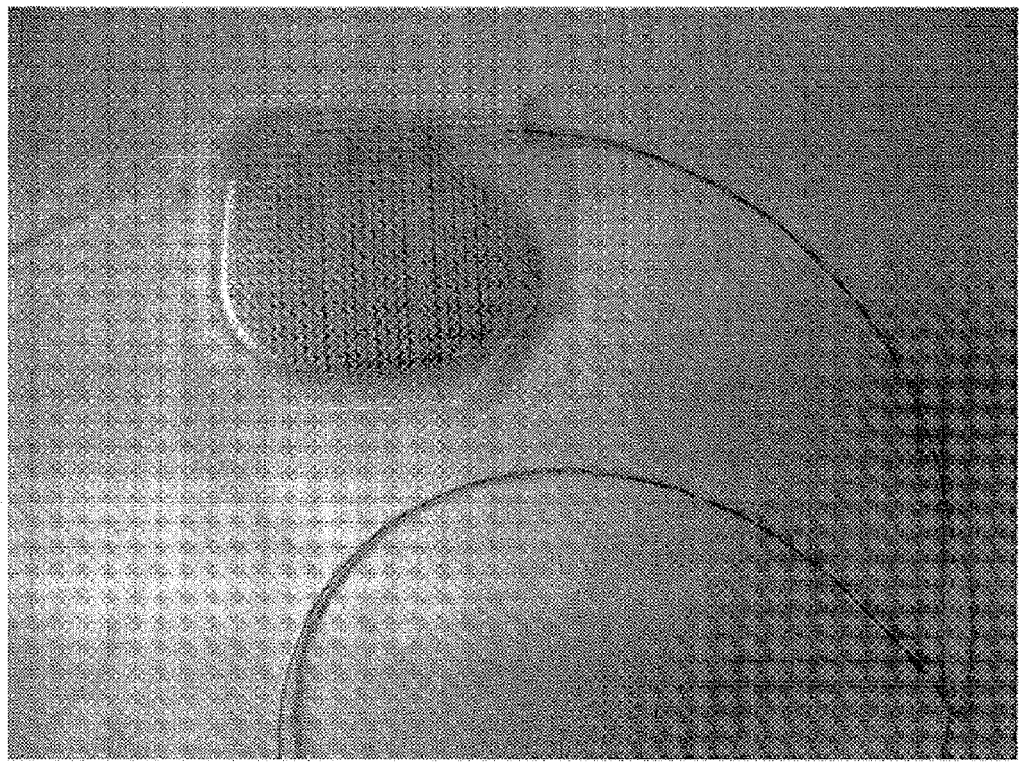
FIG. 10 is a picture of a polymer-coated pouch containing a CRM.
Figure 11:
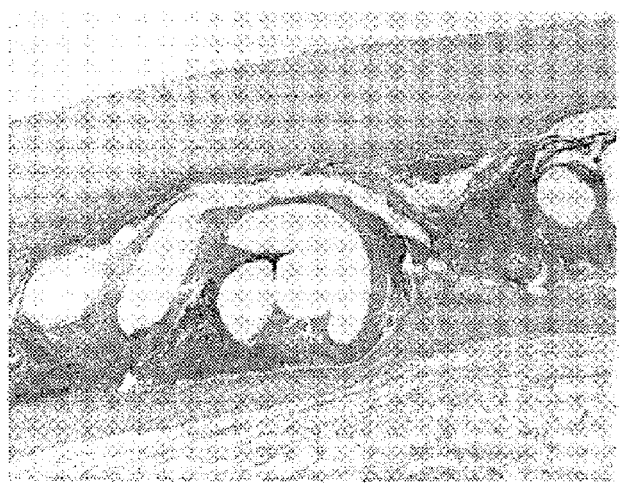
FIG. 11 is a micrograph showing the implant site of a coated-mesh pouch with device at 14 weeks post-implantation (4× magnification).

The antimicrobial pacemaker pouch is a dual component (resorbable and non-resorbable), sterile prosthesis designed to hold a pacemaker pulse generator or defibrillator to create a stable environment when implanted in the body. The pouch is constructed of a non-resorbable mesh comprised of knitted filaments of polypropylene and a bioresorbable polyarylate coating on the mesh containing the antimicrobial agents rifampin and minocycline. The antimicrobial agents are released for a minimum of 7 days followed by full resorption of the polymer, leaving a light-weight permanent mesh incorporated into the tissue and providing a stable environment for the pacemaker or defibrillator (see FIGS. 9 and 10).

The mesh for the pouch can be prepared in the same manner as antimicrobial polymer-coated surgical meshes described in U.S. provisional application 60/771,827, filed Feb. 8, 2006. The pouch is constructed of two pieces of flat, coated mesh placed one on top of the other and sealed and cut into the shape using an ultrasonic weld. This results in the formation of a pouch 2.5"×2.75" in size, sealed on approximately 3 and one-half sides, and coated with approximately 50 to 75 mg of polymer and 6.1 mg of rifampin and 6.1 mg of minocycline (of 86.11 μg/cm$^2$ for each drug). Such pouches can be designed to fit a wide range of pacemakers, implantable defibrillators, neurostimulators and other IMDs (see Table 1 and 2).

Antimicrobial Efficacy

Antimicrobial efficacy was demonstrated in laboratory (in vitro) and in animal (in vivo) testing. Results indicate that coated mesh pouch is effective in preventing microbial colonization of the mesh and generator (see Table 8).

Histological results from a dog study show that the pouch is rapidly incorporated into the tissue surrounding the pacemaker, facilitating the formation of a stable environment for holding the pacemaker (FIG. 3).

TABLE 8

Antimicrobial Efficacy

| Antimicrobial Test | Test Results |
|---|---|
| Dog Implantation Study (in vivo) | No positive cultures (0/4) detected in the coated mesh pouch + generator implant sites compared with 100% positive culture (4/4) for generator alone in response to a $5 \times 10^4$ CFU inoculum of S. aureus |
| Rabbit Implantation Study (in vivo)* | Significantly (p < 0.05) fewer colonized mesh implants (16.6%) compared to Prolene mesh comparator (43.3%) in response to a $10^5$ CFU inoculum of S. aureus* |
| Modified Kirby–Bauer Antibiotic Susceptibility Test (Disk Diffusion Test) (in vitro)* | ZOI > 1010 mm for >7 days against to S. aureus and S. epidermidis and MRSA |
| Boburden Test Method (in vitro)* | No growth to $10^6$ CFU/mL inoculum of S. aureus and, S. epidermidis after 7 days incubation, and no growth to a $10^8$ CFU/mL inoculum of MRSA after 7 days incubation* |

*Testing on antimicrobial mesh alone of the same composition

Example 7

Prevention and/or Inhibition of Biofilms in Vitro

Methods

In the in vitro study, the efficacy of the antibacterial pouch in preventing or inhibiting the formation of biofilms was assessed using a Center for Disease Control bioreactor model and confirmed by Scanning Electron Microscopy.

CDC Biofilm Reactor System: The CDC biofilm reactor (CDC-BR) system was developed by the Centers for Disease Control and Prevention, Atlanta, Ga., to assess biofilm formation and prevention on surfaces and devices. Two CDC-BR model CBR90 bioreactors (Biosurface Technologies Corporation, Bozeman, Mont., USA) were used in this study. The CDC-BR consists of a 1-L bioreactor vessel with eight polypropylene coupon holders that can accommodate three 0.5-inch diameter sample coupons suspended from the reactor lid. A liquid growth medium enters through the top of the vessel lid and exits via aside-arm discharge port. A magnetic stir bar incorporating a mixing blade provides fluid mixing and surface shear. The CDC-BR system, which forms the basis of a standard method for the growth of *Pseudomonas aeruginosa* biofilms on polycarbonate surfaces was adapted to test the ability of *S. aureus* to form biofilms on titanium coupons (mock CRMs) in an antibacterial envelope or non-antibiotic-containing control envelopes.

Two bioreactors were used in the experiments described in this study. All experiments in the study were repeated at least three times. One reactor (experimental) was used to evaluate biofilm formation on titanium coupons enclosed in the antibiotic containing envelope. whereas the other (control) was used to assess biofilm formation on coupons in control envelopes that contained no antibiotics. It was necessary to use two separate reactors for these experiments because the antibiotics in the antibacterial envelope are slowly released and easily diffuse in aqueous solutions.

In the experimental reactor, two sterile titanium coupons were enclosed in the antibacterial envelopes and two others were left unenclosed. Likewise. in the control reactor. two titanium coupons were left exposed, whereas the remaining two coupons were enclosed in non-antibiotic-containing envelopes made from the same polypropylene as used in the antibacterial envelope. Unused ports in the lid assemblies of both reactors were plugged with sterile rubber stoppers.

Bacteria: *S. aureus* ATCC strain 33591 was used in this study. Unless otherwise specified, strain 33591 was grown in tryptic soy broth (TSB; Fisher Scientific Waltham. M.A. USA) or on TSB agar plates. Bacteria were grown at room temperature for all biofilm experiments and at 37° C. for plate count experiments.

Antimicrobial pouch: The antimicrobial pouch used in these studies was the AIGIS$_{RX}$™ antimicrobial envelope manufactured by TyRx Pharma, Inc. This antimicrobial pouch consists of a polypropylene mesh with a coating of 10% minocycline hydrochloride and rifampin in a DTE-27.5% DT succinate polyarylate which was manufactured and formed into a pouch as described in Example 6.

Biofilm formation experiments: Inocula for the bioreactors were prepared by inoculating 800 mL of sterile 10%-strength TSB with overnight cultures of *S. aureus* strain ATCC 33591 and by growing these cultures at room temperature with continuous stirring for 24 hours. After incubation, 400 mL of the culture was added to a sterile experimental reactor and the remaining 400 mL was added to a second sterile control reactor. Sterile 1% TSB was continuously added to each reactor at a rate of 2.7 mL/min using a peristaltic pump.

Reactor fluid samples were removed via the exit ports from both reactors after incubation at room temperature for 24, 48, and 72 hours. After 72 hours of incubation, lid assemblies from both reactors were removed and transferred to beakers containing 400 mL of sterile phosphate buffered saline (PBS) and stirred (washed) for 5 minutes at room temperature. After the wash, the control and experimental coupons and envelopes were removed for microbiological analysis.

Microbiological analysis: After removal from the reactors individual control and experimental envelopes or titanium coupons were placed in 10 mL of PBS and sequentially vortexed (30 seconds at the maximum setting of Maxi max II Barnstead/Thermolyne stirrer [Dubuque, Iowa. USA]), sonicated for 2 minutes and then vortexed again to disaggregate biofilms and create bacterial suspensions. The bacterial suspensions were serially diluted in sterile PBS and the dilutions were spread on Tryptic Soy Agar plates that were incubated at 37'C for 24 hours. The number of colony fanning units (CFU) per sample was determined using standard microbial spread plate count methods. The number of CFU associated with the titanium coupons was expressed as CFU/cm$^2$) the number of bacteria associated with the control and experimental envelopes as CPU/envelope) and the number of bacteria in the reactor fluids as CFU/mL. Statistical analysis of bacterial counts obtained from the control and treatment reactors was conducted using a 2-tailed, Student's t-test.

Scanning electron microscopy (SEM): Exposed and unexposed titanium coupons and experimental and control envelopes were fixed with neutral buffered formalin, dehydrated with a graded ethanol series, and then air-dried. The envelopes were sputter-coated with iridium to make them conductive for SEM analyses. SEM examination of the coupons and envelopes was performed using a Zeiss Supra SSVP field-emission SEM (Thornwood, N.Y., USA).

Results

Biofilm formation with *S. aureus* 33591 ATCC strain 33591: The results from the SEM experiments revealed that *S. aureus* ATCC strain 33591 formed biofilms in the CDC-BR model system. This verified the utility of using the CDC-BR model system to evaluate the effects of the antibacterial envelope on the ability of strain 33591 to form biofilms on mock CRMs.

Figure 12:
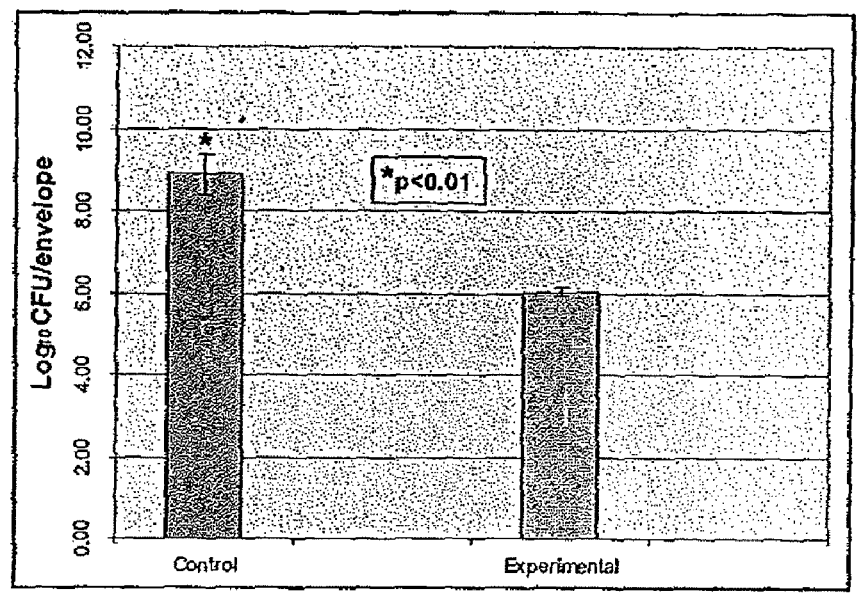
FIG. 12 depicts the number of bacteria associated with experimental (AIGIS$_{Rx}$™) and control envelopes after 72 hours at room temperature. The control and experimental envelopes were removed from the reactors after 72 hours of incubation at room temperature and processed as described to create bacterial suspensions and the number of bacteria associated with each envelope were determined. The numbers of viable bacteria associated with the control and experimental envelopes are expressed as $\log_{10}$ CFU/envelope.
Figure 13:
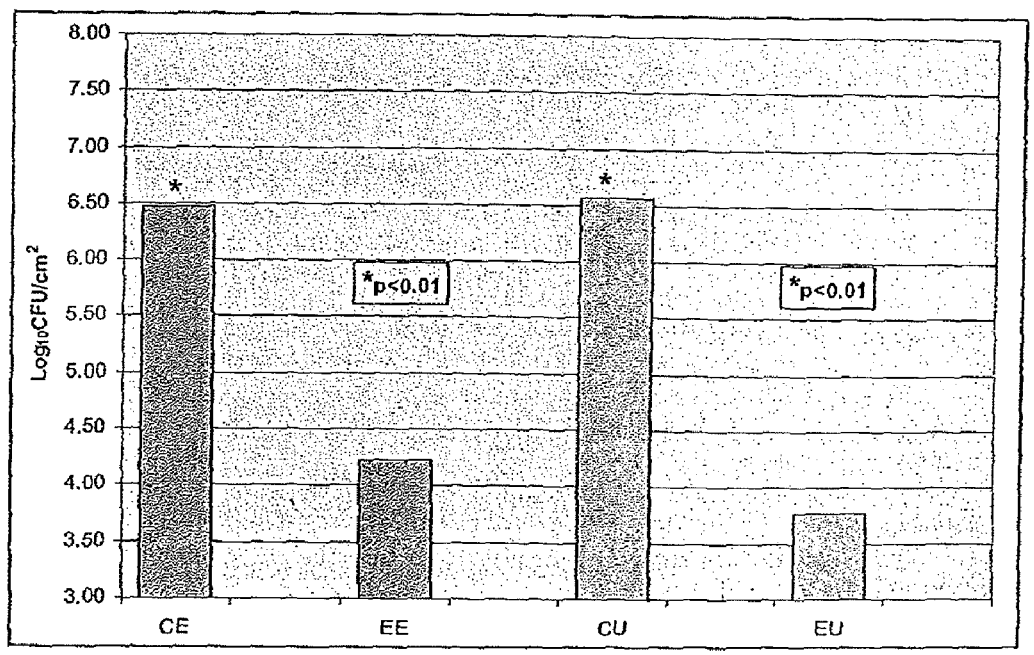
FIG. 13. Number of bacteria associated with enclosed and unenclosed titanium coupons from experimental and control reactors. Titanium coupons were removed from the reactors after 72 hours of incubation at room temperature and processed as described to create bacterial suspensions and determine the number of bacteria associated with the titanium coupons. The numbers of viable bacteria associated with the control and experimental coupons are expressed as $\log_{10}$ CFU/cm$^2$. CE=control/enveloped coupons; EE=experimental/enveloped coupons; CU=control/unenveloped (exposed) coupons; EU=experimental/unenveloped (exposed) coupons.

Microbiological analysis: The analysis of the antibacterial and control envelopes after 72 hours of incubation (FIG. 12) revealed that there was a marked and statistically significant difference (p<0.01) between the number of staphylococci associated with the antibacterial envelope (6.04 $\log_{10}$ CFU/envelope) as compared with the non-antibiotic-containing control envelopes (8.89 $\log_{10}$ CFU/envelope). Similarly, there was a statistically significant difference (p<0.01) in the number of bacteria associated with the titanium coupons enclosed in the antibacterial and control envelopes (mean $\log_{10}$ difference of 2.24 CFU/cm$^2$). Likewise, there was a statistically significant difference ($\log_{10}$ difference of 3.77 CFU/cm$^2$, p<0.01) between the number of bacteria associated with the unenclosed titanium coupons taken from the experimental and control reactors after 72 hours of incubation (FIG. 13).

Figure 14:
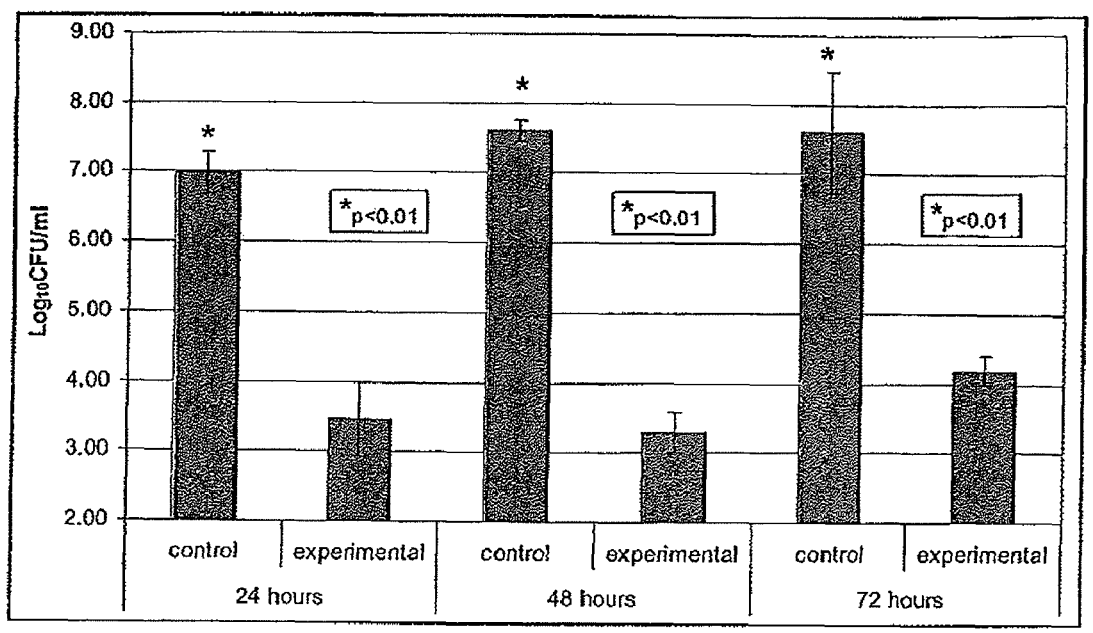
FIG. 14 depicts the number of bacteria in control and experimental reactor fluids after 24, 48, and 72 hours at room temperature. Fluids from the control and experimental reactors were removed after 24, 48, and 72 hours of incubation at room temperature and the number of viable bacteria in the samples was determined. The numbers of viable bacteria found in the control and experimental reactor fluids are expressed as $\log_{10}$ CFU/mL

Finally, there was a statistically significant difference (p<0.01) in the number of bacteria found in the experimental and control reactor fluids after 24. 48. and 72 hours of incubation (FIG. 14). The mean $\log_{10}$ difference (in CFU/mL) between the experimental and the control samples at 24, 48, and 72 hours was 3.52, 4.31, and 3.42, respectively.

The reduction (in CFU/m/L) in reactor fluid samples taken from the experimental and control reactors was confirmed by visual inspection of the reactors after 72 hours of incubation. A There was a marked reduction in bacterial growth (turbidity) in the experimental reactor as compared with the control reactor.

SEM analysis: The SEM analysis revealed that after 72 hours of incubation, there was an observable difference in the staphylococcal biofilms formed on the titanium coupons and envelopes from the control and experimental reactors. Exposed titanium coupons taken from the control reactors were colonized by large numbers of actively dividing staphylococci that formed biofilms. Biofilms also formed on the control-enveloped titanium coupons, but to a lesser extent. Far fewer bacteria were found on both exposed and enveloped titanium coupons from the experimental reactors.

Figure 15:
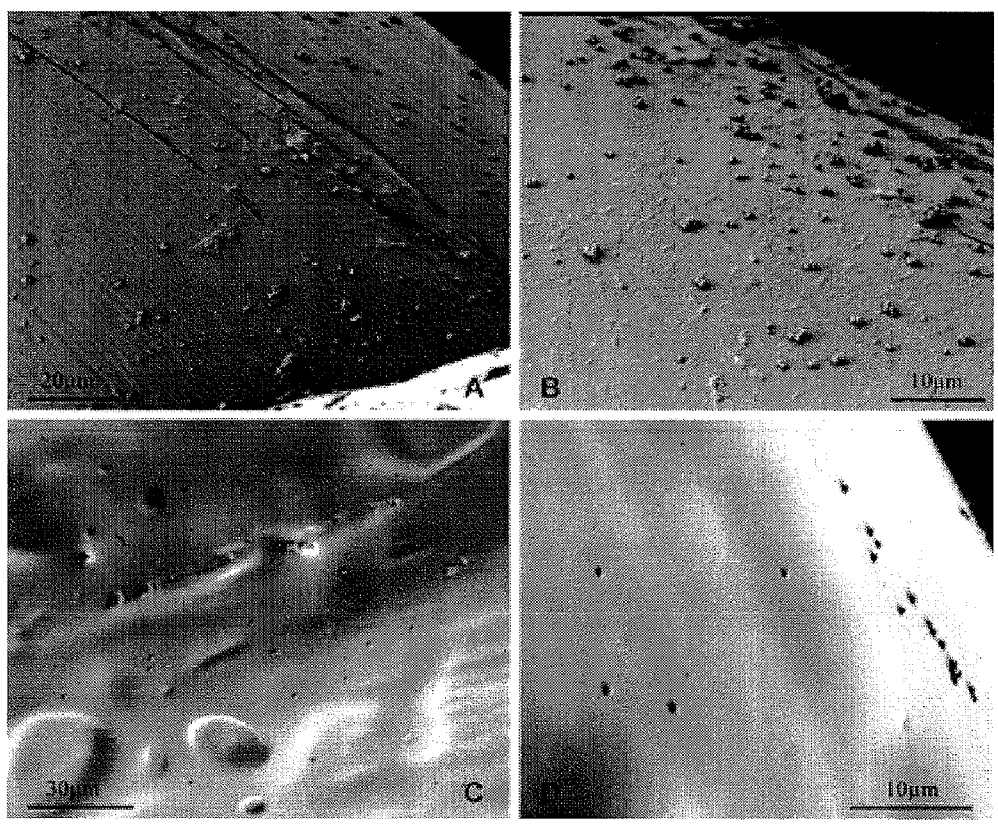
FIG. 15 depicts the *S. aureus* biofilm formation on control and experimental envelopes at different magnifications after 72 hours of incubation at room temperature. (A) Control, 500×: (B) Control 1,500×; (C) Experimental, 500×; (D) Experimental, 1,500×.

The differences in biofilm formation on the experimental (antibacterial envelope) and control envelopes were more pronounced. The control envelopes were heavily colonized with grape-like clusters of dividing staphylococci (FIGS. 15 A and B). In marked contrast, staphylococci. were rarely observed on the antibacterial envelopes, and when present, they were typically observed as single, isolated bacterial cells. (FIGS. 15 C and D).

Example 8

Prevention and/or Inhibition of Biofilms in Vivo

Methods

Bacteria: Bacterial strains were obtained from ATCC (American Type Culture Collection): *Staphylococcus epidermidis* (ATCC #35984), *Staphylococcus capitis* (ATCC #27840), *Escherichia coli* (ATCC #25922), and *Acinetobacter baummanii* (ATCC #43608). One day prior to implant, an aliquot of a specific strain was thawed from frozen stock and grown overnight in liquid trypticase soy broth (TSB) for 16-19 hours. The cultures were washed in saline, and the culture concentration was determined by spectrophotometry and compared to a pre-determined growth curve. Each culture was brought to the desired concentration and prepared in individual 1-mL syringes for inoculation. The bacterial inoculum was checked by plating dilutions of the final culture solution as well as plating dilutions from one additional syringe post-surgery.

Rabbit Infection Model: New Zealand white rabbits. at least 2.5 kg and specific pathogen-free, were weighed and anesthetized using given intramuscular (IM) acepromazine (1 mg/Kg), ketamine (40 mg/kg), and xylazine (2.5 mg/Kg) pre-operatively. The fur on the back of the animals was shaved, and the back of each rabbit was washed with a surgical scrub (e.g., Betadine), wiped with dilute alcohol, painted in Betadine, and draped for surgery. A 2.0-2.5 cm lateral incision along the ventral surface on one side of the spine was created through the dermal layer. A single incision was made parallel to the mid-line of the back, cutting through the fascia and exposing the paravertebral muscle. The fascial membrane and portion of the trapezius muscle was incised with a scalpel creating a nominal implant site. Bleeding was controlled with gauze and pressure. Using blunt dissection, an implant pocket was created along the left lateral wall toward the lateral aspect of the left scapula of the rabbit. The pocket was extended approximately 3-4 cm. A separate, small incision was made just lateral to the first incision, to accept a catheter to be tunneled into the pocket for bacteria delivery.

Once the pocket was created, a bacterial injection cannula was created by removing the distal needle from a butterfly catheter. The 1.5 mm tube was placed into the pocket between the pacing device and the infraspinous fossa of the scapula. The tube was temporarily secured with a purse-string suture. A sterile pacing device (with or without a sterile anti-bacterial pouch, as indicated) was then inserted into the pocket, and the pocket was closed by suturing the subcutaneous layer to the underlying muscle layer using a mattress stitch and 3.0 prolene sutures. A syringe containing an individual bacterial dose was used to inject bacteria into the pocket using the cannula followed by 1.0 mL of sterile saline from a separate sterile syringe. The cannula was removed and the purse-string suture was closed to seal the pocket. The same procedure was performed on the contralateral side, using the same cutaneous incision and tunneling with blunt dissection into the contralateral side. Following device implant, the sub-cutaneous tissues were then closed using 3.0 vicryl sutures and interrupted stitches, the bacterial inoculum and saline rinse were injected into the catheter placed into this contralateral pocket, and the cutaneous tissues were closed using surgical staples or sutures. Animals were observed during post-operative recovery until body temperature was normal and animal was alert and responsive. The rabbits were observed daily throughout the seven day study.

Antimicrobial pouch: The antimicrobial pouch used in these studies was the AIGIS$_{RX}$™ antimicrobial envelope manufactured by TyRx Pharma, Inc. This antimicrobial pouch consists of a polypropylene mesh with a coating of 10% minocycline hydrochloride and rifampin in a DTE-27.5% DT succinate polyarylate which was manufactured and formed into a pouch as described in Example 6.

Necropsy and Bacterial Sampling at Explant: At seven days post-surgery, animals were euthanized using a sodium pentothal injection (Euthasol). The implant site was prepared in the same manner as for the surgical implant assuring that the site was aseptic. The pocket containing the device was entered using aseptic techniques, creating a new incision site just dorsal to the original incision. A digital photo was obtained of the opened implant pocket.

The device was removed and swabbed with a sterile cotton swab. A specific swabbing procedure was developed for use with this study to ensure uniform and thorough sampling. Four swabs were collected for each device to sample distinct areas of the device: Swabs 1 and 2 sampled the front and back face of the device, respectively, by swabbing the complete surface area of the device in a back and forth manner from top to bottom. Swab 3 was used to wipe the sides and bottom of the device, starting at the top left side, along the bottom, and back up the right side to the top. The fourth swab covered the areas surrounding the lead ports.

Two swabs were obtained from the pocket area. One was wiped 3 times around the bottom of the pocket. The second collected other areas of the pocket in which pus existed. Each swab was streaked onto a trypticase soy agar (TSA) plate and cultured for 24-48 hours at 37° C. Plates were examined for presence of bacterial colonies, and the presence of one or more colonies was defined as "positive." Plates were defined as negative if no colonies were observed after 48 hours of culture.

The device was then placed in a sterile plastic bottle with screw top lid with sterile saline+0.5% Tween-80 to cover the device. Bacterial recovery from the device proceeded through a series of vortex and sonication steps. The bottle with the device and saline was vigorously vortexed for 15 seconds, followed by sonication for 5 minutes. The device was transferred to a new sterile jar and fresh saline+0.5% Tween 80. This jar containing the device was vigorously vortexed for 30 seconds, followed by placement in a sonicator bath, and sonication for 5 minutes. Each sonicant solution was transferred to labeled 50 mL sterile tubes, resulting in two sonication samples.

Serial dilutions ($10^{-1}$, $10^{-2}$, and $10^{-3}$) were prepared from each sample (Sonicant 1 and Sonicant 2) and 200 μL was streaked onto a TSA plate. Plates were cultured overnight. All samples were prepared and plated on the day of explant. If bacteria were isolated and grown, the plate was scored as positive, and the colony count was quantified.

Bacterial Strain Identification: A single colony recovered from each device was analyzed by Gram stain and API™ test strips (BioMerieux, France) to determine bacterial strain.

Analysis of Systemic Antibiotic Level: Blood was drawn at study termination, and plasma was collected and frozen for assay of minocycline and rifampin levels. Minocycline (Sigma Aldrich) was stored at approximately 5° C.; rifampin (Sigma Aldrich) was stored at room temperature; and the internal standard, rifabutin (USP) was stored at approximately −20° C. Plasma samples were extracted in acetonitrile, centrifuged, and supernatant was transferred to a 96-well plate and evaporated to dryness under nitrogen. Each well was reconstituted in acetonitrol-water (15:85) and 5 μl was applied to an LC-MS/MS system (Scitex 4000 Q-trap). Samples were run on a Synergy Hydro-RP, 50×2.0 mm, 4 μm column, with mobile phase 1 in 0.5% formic acid in water, and phase B in 0.5% formic acid in acetonitrile-methanol (1:1) at a flow rate of 0.5 mL/minute. Sample concentrations were determined relative to minocycline and rifampin standards run under identical conditions.

Scanning Electron Microscopy (SEM): Explanted devices for SEM were placed in 2% glutaraldehyde fixative solution immediately upon explant. After sufficient time for fixation (overnight), samples were chemically dehydrated using stepwise ethanol dehydration steps (70-100%) followed by immersion in hexamethyldisilazane (HMDS), and allowed to air-dry. Samples were then sputter-coated with gold and viewed on a Hitachi S3500N Variable Pressure Scanning Electron Microscope.

It will be appreciated by those skilled in the art that various omissions, additions and modifications may be made to the invention described above without departing from the scope of the invention, and all such modifications and changes are intended to fall within the scope of the invention, as defined by the appended claims. All references, patents, patent applications or other documents cited are herein incorporated by reference in their entirety.

Example 8a

S. epidermis Challenge

Figure 16:
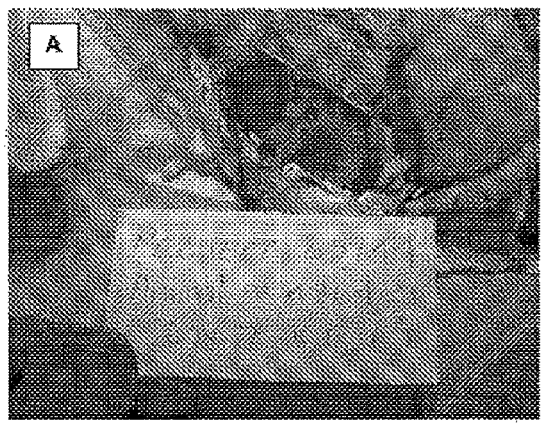
FIG. 16 depicts the explantation and sampling procedure. (A) Aseptic surgical exposure of the implant pocket 7 days after implantation demonstrates a biofilm on the device inoculated with *S. epidermidis*. (B) In contrast to (A), the pocket containing the device within an antimicrobial pouch is free of the biofilm material. (C) Aseptic swabbing of a device implanted without an antimicrobial pouch demonstrates formation of biofilm material, (D) Removal of the device from the antimicrobial pouch demonstrates a device surface free of the biofilm material.
Figure 16:
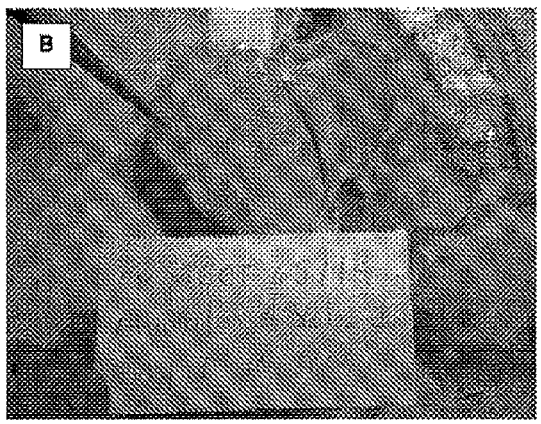
Figure 16:
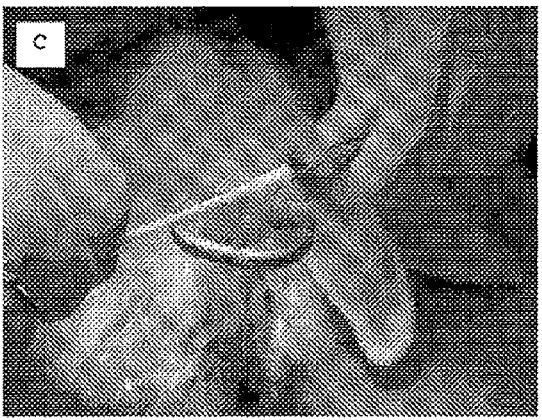
Figure 16:
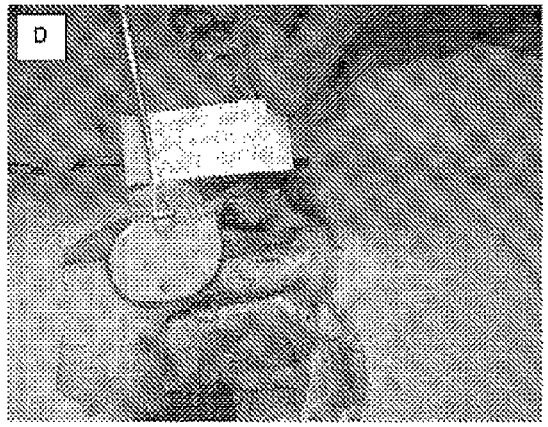

The rabbit model of in vivo device infection was used to assess infection and biofilm formation. One milliliter of approximately $1\times10^{10}$ CFU/mL S. epidermidis was inoculated into subcutaneous pockets containing either a pacing device alone, or a pacing device with the antimicrobial pouch. Pilot studies were initially performed to determine appropriate dose of bacteria needed to create a consistent, non-lethal infection. For the efficacy study, there were 3 animals per group having the device with antimicrobial pouch (n=6) and 3 animals in the control group having the device without an antimicrobial pouch (n=6). Gross observations of the appearance of the device and pocket at explant revealed that each implant pocket containing a device without pouch contained white, pus-like material to varying degrees in the pocket, and white filmy material on the device surface (FIG. 16A). Some erythema of the pocket tissue was present. Each implant pocket containing the device with anti-microbial pouch was void of this white, filmy material (FIG. 16B). A summary of gross observations of signs of clinical infection is presented in Table 9 with "Sign of Infection" defined as presence of white filmy or mucous-like material (pus) on the device.

The presence of some tissue-like material on the devices with pouches was noted, which appeared related to fibrous tissue ingrowth rather than clinical infection. There was host tissue ingrowth into the pouch, with mild erythema of the pocket tissue. When removed from the pouch, the device surface was clear of pus-like material in each device implanted with a pouch.

A summary of bacterial colonization from swabs is presented in Table 10. Each implant from the control group demonstrated two or more positive swabs from the device and/or pocket. In contrast, all swabs from devices and implant pockets from the test group were negative.

Following the swabbing procedure, the devices were subjected to a series of vortex and sonication steps, as detailed above and in Materials and Methods, to dislodge any bacteria that may be adherent to the device. These sonication solutions were serially diluted and plated on TSA plates, and resulting colonies were counted (Table 11). There was extensive colony growth from all device sonication samples in the group without pouches. In contrast, all devices contained within the antimicrobial pouches had negative sonication samples.

TABLE 9

Clinical Observations at Necropsy after *S. epidermidis* Infection

| Group | Animal No. | Implant Side | Sign of Infection* Yes | Sign of Infection* No |
|---|---|---|---|---|
| Device Only | 4864 | Left | ✓ | — |
|  |  | Right | ✓ | — |
|  | 4866 | Left | ✓ | — |
|  |  | Right | ✓ | — |
|  | 4868 | Left | ✓ | — |
|  |  | Right | ✓ | — |
| Device with Pouch | 4861 | Left | — | ✓ |
|  |  | Right | — | ✓ |
|  | 4863 | Left | — | ✓ |
|  |  | Right | — | ✓ |
|  | 4869 | Left | — | ✓ |
|  |  | Right | — | ✓ |

TABLE 10

Swabs (+ = 1 or more colonies per plate)

| Group | Animal No. | Implant Side | Device front | Device back | Device side | Device top | Pocket bottom | Pocket side |
|---|---|---|---|---|---|---|---|---|
| Device only | 4864 | Left | − | − | + | − | − | + |
|  |  | Right | + | + | + | + | + | + |
|  | 4866 | Left | − | + | + | − | − | − |
|  |  | Right | + | + | + | − | + | + |
|  | 4868 | Left | + | + | + | + | + | + |
|  |  | Right | + | + | + | − | + | + |
| Device with pouch | 4861 | Left | − | − | − | − | − | − |
|  |  | Right | − | − | − | − | − | − |
|  | 4863 | Left | − | − | − | − | − | − |
|  |  | Right | − | − | − | − | − | − |
|  | 4869 | Left | − | − | − | − | − | − |
|  |  | Right | − | − | − | − | − | − |

TABLE 11

| Group | Animal No. | Implant Side | Sonication 1 (# of colonies) Undil | $10^{-1}$ | $10^{-2}$ | $10^{-3}$ | CFU mL$^{-1}$ | Sonication 2 (# of colonies) Undil | $10^{-1}$ | $10^{-2}$ | $10^{-3}$ | CFU mL$^{-1}$ | Tissue Homogenate (undiluted) |
|---|---|---|---|---|---|---|---|---|---|---|---|---|---|
| Device Only | 4864 | Left | 47 | 2 | 0 | 0 | 230 | 88 | 7 | 0 | 0 | 440 | 0 |
|  |  | Right | 44 | 2 | 0 | 0 | 220 | 29 | 4 | 0 | 0 | 145 | 136 |
|  | 4866 | Left | 1 | 0 | 0 | 0 | 5 | 1 | 0 | 0 | 0 | 5 | 0 |
|  |  | Right | 28 | 6 | 0 | 0 | 140 | 52 | 6 | 0 | 0 | 260 | 52 |
|  | 4868 | Left | 116 | 8 | 4 | 0 | 580 | 47 | 10 | 1 | 0 | 235 | TNC |
|  |  | Right | 9 | 0 | 0 | 0 | 45 | 6 | 0 | 0 | 0 | 30 | 44 |
| Device with pouch | 4861 | Left | 0 | 0 | 0 | 0 | 0 | 0 | 0 | 0 | 0 | 0 | 0 |
|  |  | Right | 0 | 0 | 0 | 0 | 0 | 0 | 0 | 0 | 0 | 0 | 0 |
|  | 4863 | Left | 0 | 0 | 0 | 0 | 0 | 0 | 0 | 0 | 0 | 0 | 0 |
|  |  | Right | 0 | 0 | 0 | 0 | 0 | 0 | 0 | 0 | 0 | 0 | 0 |
|  | 4869 | Left | 0 | 0 | 0 | 0 | 0 | 0 | 0 | 0 | 0 | 0 | 0 |
|  |  | Right | 0 | 0 | 0 | 0 | 0 | 0 | 1 | 0 | 0 | 2 |

Example 8b

Challenge with Additional Bacterial Strains

To demonstrate efficacy across a range of pathogens, the same implant model was employed using other bacterial strains, including *Escherichia coli* (*E. coli*), *Staphylococcus capitis* (*S. capitis*), and *Acinetobacter baumannii* (*A. baumannii*). A summary of the inoculum dose for each strain and the resulting bacterial recovery results are presented in Table 12. In the table, "+" means signs of clinical infection were observed, as defined by presence of pus- or mucous-like material on device.

Pilot dosing studies were performed to determine the appropriate dose to yield consistent, non-lethal infection. For the *S. capitis* pilot dosing study, only minimal bacteria were recovered following a 7 day implant, though the pocket had signs of clinical infection, suggesting that the host's immune system may have fought the bacteria, leaving a sterile exudate. A two-step design was then used for the efficacy study in which $1 \times 10^8$ CFU/mL was inoculated into 4 animals (2 devices each; n=2 per test and control groups), then explanted at 3 days post-surgery, and $1 \times 10^{10}$ CFU/mL was inoculated into 4 more animals (n=2 per test and control groups) with explants 7 days post-surgery. For the other studies, 3 animals were inoculated per test and control groups (n=6 devices per group).

Each bacterial strain generated significant pocket infection with observable biofilm-like material on the device surfaces and extensive colonies grown from sonicant samples and swabs of the devices implanted without the antimicrobial pouch. In each study, the use of the anti-microbial polymer mesh pouch eradicated bacteria samples by both swabbing and sonication methods.

TABLE 12

| Organism | Innoculum Size | 7 day Clinical Infection | | 7 Day Micro Assessment | |
|---|---|---|---|---|---|
| | | Pacemaker Only | Pacemaker and Pouch | Pacemaker Only | Pacemaker and Pouch |
| A. baummannii | $10^9$ | + | − | + | − |
| S. capitis | $10^9$ | + | − | + | − |
| S. epidermidis | $10^{10}$ | + | − | + | − |
| E. coli | $10^7$ | + | − | + | − |

Systemic Antibiotic Levels: Blood was drawn at termination for the 3- and 7-day S. capitis study to determine if the AIGIS$^{RX}$ antimicrobial pouch resulted in circulating levels of systemic antibiotic. Plasma was collected from the drawn blood, and samples were analyzed for levels of rifampin and minocyline by Covance Laboratories, Inc. (Madison. Wis.). Results of LC-MS/MS analysis demonstrates no detectable level of either antibiotics detected greater than 2 ng/mL in any of the rabbit blood from this study at 3- or 7-days post-implant.

Figure 17:
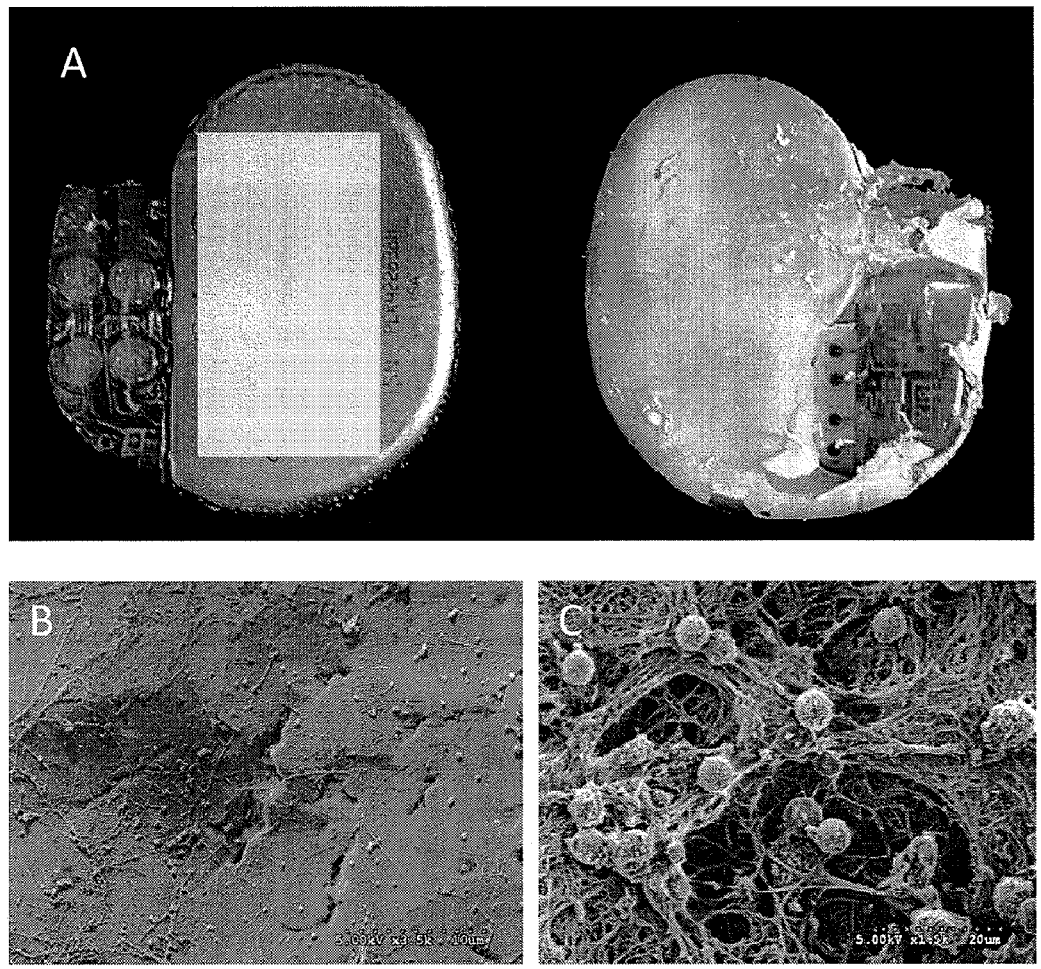
FIG. 17 depicts the macroscopic and scanning electron microscopic analysis of biofilm formation on implanted pacing cans with or without the antimicrobial pouch with *Acinetobacter baummnanii* inoculation. (A) Macroscopic appearance of the pacing devices following dehydration, prior to gold sputter-coating. The pacing can on the left was implanted within an antimicrobial pouch, while the pacing can on the right was implanted without an antimicrobial pouch. (B) SEM of the surface of the device shown on the left in (A), (C) SEM of the surface of the device shown on the right in (A).

SEM of Device Biofilm at Explant: Some devices explanted from the A. baummannii study were processed for scanning electron microscopy immediately following explant. FIG. 17A demonstrates the gross appearance of the dehydrated pacing devices prior to further processing. The pacing can on the left had been implanted within the antimicrobiocrobial pouch, while the device on the right was implanted without an antimicrobial pouch. The biofilm material is evident in the device on the right.

One sample from a test group (with antimicrobial pouch and inoculated with $1\times10^8$ A. baummannii) and one from a control group (device implant only and pocket inoculated with $1\times10^8$ A. baummannii) were each visualized for signs of biofilm on the device surface. Representative images are shown in FIGS. 17B and C. Extensive evidence of bacteria and matrix-like material are evident on the device implanted without the antimicrobial pouch (FIG. 17C), while the surface of the device implanted within the antimicrobial pouch has no evidence of bacteria (FIG. 17B).

Example 9

Prevention and/or Inhibition of Biofilms in Vivo

Method

Creation Of Initial Bacterial Stock: S. aureus was obtained from the American Type Culture Collection (ATCC #29213), S. epidermidis (ATCC 35984), S. capitis (ATCC 27840) and E. coli (ATCC 25922). Master and working stocks were created from this culture and frozen for future use.

Development of Inoculum: One day prior to surgery, a frozen aliquot of S. aureus, S. epidermidis, S. capitis, and E. coli stock was quickly thawed, put into liquid media and placed in a shaking water bath at approximately 37° C. overnight at a sufficient volume to produce required Inoculum. After a 16-19 hour culture period, the cultures were centrifuged, the broth decanted, and the bacterial pellet re-suspended in an appropriate volume of fresh, sterile phosphate-buffered saline (PBS). Optical density of each culture was determined by spectrophotometry. The cultures were diluted to the target concentration of $1.0\times10^7$ CFU/mL (S. aureus and E. coli) and $1.0\times10^{10}$ CFU/mL (S. capitis and S. epidermidis) for inoculation and $1.0\times10^1$ (S. aureus) and $1.0\times10^{11}$ (S. epidermidis) for the repeat of Groups 1 and 2 (Table 13), An aliquot from each concentration was diluted appropriately and inoculated onto trypticase soy agar (TSA) plates to confirm CFU/mL. One mL aliquots of the cultures were loaded into sterile 3 cc syringes for each rabbit to be implanted. Two additional syringes were prepared from each culture as replacements and to culture at the end of the implants to confirm CFU/mL.

Selection of Animals: Animals were selected at random from a larger pool of animals. Animals were of sufficient size to accommodate implants into the paravertebral muscles. Each animal was observed for any signs of disease prior to introduction into the study. Any animals considered unsuitable due to poor health or outlying body weight were excluded from the study.

Animal Preparation: Each rabbit was weighed and the weight recorded to the nearest 0.1 kg. Initially, the rabbits were anesthetized with a combination of ketamine (20 mg/kg) and acepromazine (0.5-1 mg/kg) intramuscular doses to a degree deep enough to prevent muscular movements (surgical plane). Each animal was given an injection of an analgesic (buprenorphine at 0.05-0.1 mg/kg subcutaneously) immediately prior to the implantation procedure. Isoflurane was delivered via nose cone as needed to maintain a surgical plane. The fur on the back of the animals was removed with an electric clipper to expose a sufficient area and the loose fur was removed. The back of each rabbit was washed with a surgical scrub (e.g. Betadine), wiped with dilute alcohol, painted in Betadine, and draped for surgery Test Article Preparation: Aseptic preparation was used for any sterile articles. Two test articles were prepared for each rabbit.

Test Article Administration—Surgical Procedure: A 2.0-2.5 cm lateral incision along the ventral surface of the spine was created through the dermal layer, A single incision was made, parallel to the mid-line of the back, cutting through the fascia and exposing the paravertebral muscle. The fascial membrane was incised with a scalpel creating a nominal implant site. Bleeding was controlled with gauze and pressure. Using blunt dissection, implant pockets were created bilaterally along the lateral wall toward the lateral aspect of the scapula of the rabbit. The pocket extended approximately 3-4 cm toward the hamate process, Once each pocket was created, a single sterile device was inserted into each pocket. A bacterial injection catheter was created by removing the distal needle from a Vacutainer® blood collection set. The 1.5 mm tube was placed into each pocket between the pacing device and the infraspinous fossa of the scapula. The tube was temporarily secured with a purse-string suture.

A pocket surrounding each device was created using a continuous stitch and prolene sutures reconnecting the subcutaneous tissues around the device, The subcutaneous tissues were closed using vicryl sutures and interrupted stitches and the cutaneous tissues were closed, leaving only the distal end of the catheter in the pocket. The previously prepared syringe was used to inject the determined dose of S. aureus, S. epidermidis, S. capitis or E. coli, into each pocket using the catheter followed by 1.0 mL of sterile saline from a separate sterile syringe to flush the catheter. The catheter was removed and the purse-string suture was closed to seal the pocket. Animals were observed daily over the course of 7 days.

Post-Implantation Care: Each animal was given an injection of an analgesic (buprenorphine) immediately following the implantation procedure and again the day after the implantation procedure. The animals were placed on towels and monitored until they were awake and upright. Animals were observed over the course of 7 days.

Clinical Observations: Clinical observations were recorded daily for each animal. Observations were typically cage side, looking for signs of illness, injury, or abnormal behavior.

Animals were weighed and euthanized using a sodium pentothal injection (Euthasol) to effect. The implant site was prepared in the same manner as for the surgical implant assuring that the site was aseptic. The pocket containing the device was entered using aseptic techniques, Digital images of the pocket and device were obtained.

The anti-bacterial pouch or shell ($AIGIS_{Rx}$™) was aseptically removed from each device, if present, and placed into a labeled, saline-filled container. The cardiac pacing devices were placed in freshly prepared 2.5% glutaraldehyde or phosphate-buffered saline. The implant pockets were swabbed once with a sterile cotton swab, and were placed into sterile labeled Whirlpack bags and given to the microbiologist for streaking onto TSA plates. For the repeat of Groups 1 and 2, the cardiac pacing devices from animals 9644 and 9645 were placed in 50 mL sterile saline with 0.5% Tween 80 and underwent a series of two vortex/sonication steps to remove adherent bacteria. The containers with each device were vigorously vortexed for 30 seconds, followed by placement in a sonicator bath and sonication for 5 minutes. The sonicant solution was transferred to a labeled 50 mL sterile tube, and 50 mL fresh saline with 0.5% Tween-80 was added to the mesh in the original container. This container was again vigorously vortexed for 30 seconds, followed by placement in a sonicator bath, and sonication for 5 minutes. The sonicant solution was transferred to a labeled 50 mL sterile tube. The process was repeated resulting in three sonicant solutions per device. Each sonication specimen to be plated was diluted $10^{-1}$, $10^{-2}$ and $10^{-3}$ by serial dilution. Two hundred mL of each dilution and the undiluted sample were plated onto TSA plates, and incubated overnight up to 48 hours to quantify dislodged bacteria.

The swabs were streaked onto TSA plates and incubated up to 48 hours at approximately 37° C. Plates were examined for the presence of colonies, and scored as positive if one or more colonies were present, and negative if no colonies are present.

A resulting colony from each device/animal was identified for bacterial strain via Gram stain, colony morphology, and API™ test strips.

Results

Bacterial Cultures for Inoculum: The *S. aureus, S. epidermidis, S. capitis,* and *E. coli* overnight cultures created to prepare inoculum were successful and yielded viable, colony-forming bacteria. The cultures were diluted or concentrated to prepare each inoculum dose and were plated to quantify actual CFUs, both immediately after inoculum preparation, and again at the end of implant. The actual CFUs were $5.8 \times 10^8$ (*S. aureus*), $4.3 \times 10^9$ (*S. epidermidis*), $1.3 \times 10^{10}$ (*S. capitis*), and $1.2 \times 10^7$ (*E. coli*) CFU/mL from the 4 doses, respectively, at pre-implant, and $5.5 \times 10^6$, $4.9 \times 10^9$, $1.2 \times 10^{10}$ and $1.0 \times 10^7$ CFU/mL for the four doses, respectively, post-implant, which is slightly above the target inoculums of $1 \times 10^{10}$ and $1 \times 10^7$ for *S. capitis* and *E. coli*, and slightly below the target inoculum of $1.0 \times 10^7$ and for $1.0 \times 10^{10}$ for *S. aureus* and *S. epidermidis*. For the repeat of Group 1 and 2, preimplant CFUs were $1.5 \times 10^9$ CFU/mL (*S. aureus*) and $6.0 \times 10^{10}$ (*S. epidermidis*) and $6.3 \times 10^9$ and $4.8 \times 10^{10}$ post-implant. The target inoculums have an inherent variability, and are expected within the bacteria inoculum studied. Mixed colonies were observed on the viability confirmation plates for the repeat of Groups 1 and 2. Colonies appeared to be a mix of *S. aureus* and *S. epidermidis*.

Daily Animal Observations: All animals were successfully implanted with device and *S. aureus, S. epidermidis, S. capitis,* and *E. coli* inoculum as described in Table 14. Clinical observations of animal health are described in Table 15. In the repeat animal study. the urine was noted to be darker in the Group 2 (n=2) animals. This was noted at one observation time-point (Day 7). This finding was not noted in the initial study with *S. aureus* and *S. epidermidis*, and is considered an insignificant finding. No adverse signs of clinical health were observed throughout the study period for any of the animals.

TABLE 13

Preliminary Animal Information

| GROUP # | ANIMAL ID# | BEGINNING WEIGHT (KG) | BACTERIA INOCULATED (TARGET DOSE) | TERMINAL WEIGHT (KG) |
|---|---|---|---|---|
| 1 | 8327 | 2.9 | $1 \times 10^7$ | 3.1 |
| (*S. aureus*) | 8320 | 2.8 | | 3.0 |
| | 9644* | 3.2 | $1 \times 10^8$ | 3.2 |
| | 9646* | 3.7 | | 3.7 |
| 2 | 8245 | 2.7 | $1 \times 10^{10}$ | 2.8 |
| (*S. epidermidis*) | 8246 | 2.5 | | 2.5 |
| | 9642* | 3.7 | $1 \times 10^{11}$ | 3.4 |
| | 9645* | 3.0 | | 2.8 |
| 3 | 8244 | 2.9 | $1 \times 10^{10}$ | 2.9 |
| (*S. capitis*) | 8247 | 3.0 | | 3.1 |
| 4 | 8248 | 2.8 | $1 \times 10^7$ | 3.0 |
| (*E. coli*) | 8251 | 2.7 | | 2.7 |

*Groups 1 and Group 2 were repeated with new animals.

TABLE 14

Implantation of Animals

| | | | IMPLANT | | | |
|---|---|---|---|---|---|---|
| | | | PACING DEVICE (LOT #)* | | BACTERIA INOCULATED (✓) | |
| GROUP | SEX | ANIMAL # | R | L | R | L |
| Group 1 | Male | 8327 | Med SR PJG190296H | KDR703 | ✓ | ✓ |
| | Male | 8320 | KDR401 | KDR401 | ✓ | ✓ |
| | Male | 9644 | NA | NA | ✓ | ✓ |
| | Male | 9646 | NA | NA | ✓ | ✓ |
| Group 2 | Male | 8245 | KDR703 | KDR401 | ✓ | ✓ |
| | Male | 8246 | KDR401 | KDR401 | ✓ | ✓ |
| | Male | 9642 | NA | NA | ✓ | ✓ |
| | Male | 9645 | NA | NA | ✓ | ✓ |
| Group 3 | Male | 8244 | KDR401 | KDR401 | ✓ | ✓ |
| | Male | 8247 | KDR401 | KDR401 | ✓ | ✓ |
| Group 4 | Male | 8248 | KDR401 | KDR401 | ✓ | ✓ |
| | Male | 8251 | KDR401 | KDR401 | ✓ | ✓ |

*The AIGIS envelope was placed in the left side of all animals, and placed on the right side of animals 9644 and 9646 (Group 1) and 9642 and 9645 (Group 2) from the repeat. The AIGIS envelope was placed on the Left side for animals 9644 and 9645, and placed on the Right side of animals 9646 and 9642.
NA: not available

TABLE 15

Daily Animal Observations after Implantation

| ANIMAL # | DAY 1 | DAY 2 | DAY 3 | DAY 4 | DAY 5 | DAY 6 | DAY 7 |
|---|---|---|---|---|---|---|---|
| 8327 | ✓[a] | ✓ | ✓ | ✓ | ✓[b] | ✓[c] | ✓ |
| 8320 | ✓[a] | ✓ | ✓ | ✓ | ✓[b] | ✓[c] | ✓ |
| 9644* | ✓[d] | ✓ | ✓ | ✓ | ✓ | ✓ | ✓ |
| 9646* | ✓[d] | ✓ | ✓ | ✓ | ✓ | ✓ | ✓ |

TABLE 15-continued

Daily Animal Observations after Implantation

| ANIMAL # | DAY 1 | DAY 2 | DAY 3 | DAY 4 | DAY 5 | DAY 6 | DAY 7 |
|---|---|---|---|---|---|---|---|
| 8245 | ✓[a] | ✓ | ✓ | ✓ | ✓ | ✓ | ✓ |
| 8246 | ✓[a] | ✓ | ✓ | ✓ | ✓ | ✓ | ✓ |
| 9642* | ✓[d] | ✓ | ✓ | ✓ | ✓ | ✓ | ✓[e] |
| 9645* | ✓[d] | ✓ | ✓ | ✓ | ✓ | ✓ | ✓[e] |
| 8244 | ✓[a] | ✓ | ✓ | ✓ | ✓ | ✓ | ✓ |
| 8247 | ✓[a] | ✓ | ✓ | ✓ | ✓ | ✓ | ✓ |
| 8248 | ✓[a] | ✓ | ✓ | ✓ | ✓ | ✓ | ✓ |
| 8251 | ✓[a] | ✓ | ✓ | ✓ | ✓ | ✓ | ✓ |

✓ = No abnormalities found
*Groups 1 and Group 2 were repeated (n = 4 animals).
[a]Post-op Buprenex given
[b]Left pocket had thickened feeling
[c]Slightly thicker pocket on left side
[d]Buprenorphene and Rimadyl administered at same dose as day of surgery, fecal matter, no urine present.
[e]Urine appears to be a medium color brown compared to normal urine color of Group 1 animals on their cage papers.

Clinical (Gross) Observations at Explant: All gross observations at explant are presented in Table 16. All incision sites were clean, the test articles were found to be in place, and the pockets were intact. Thin to moderate film capsule formation was observed on the pacemaker only devices in 6/8 animals, with a viscous liquid within the pocket and on the pacemaker was grossly observed on the pacing device in 2/8 animals (Animal #8327 and #8320), while no film was noted on the pacemaker with AIGIS$_{Rx}$™ in these early explants. Pacemaker with AIGIS$_{Rx}$™ articles and control pacing devices for animals 8244, 8246, 8248, 8320, 9646 and 9642 were placed in 2.5% glutaraldehyde and submitted for SEM. Pacemaker with AIGIS$_{Rx}$™ articles and control pacing devices for animals 8245, 8247, 8251, and 8327 were placed in phosphate buffered saline and submitted for confocal microscopy.

TABLE 16

Macroscopic (Gross) Clinical Observations

| ANIMAL # | IMPLANT SIDE | MACROSCOPIC (GROSS) OBSERVATIONS |
|---|---|---|
| 8327 | Right | Incision appears well healed. Viscous liquid within pocket and on pacemaker |
| | Left | Incision appears well healed. Bacterial envelope intact. Removed bacterial envelope, pacing device clean. |
| 8320 | Right | Incision appears well healed. Viscous liquid within pocket and on pacemaker. |
| | Left | Incision appears well healed. Bacterial envelope intact. Removed bacterial envelope, pacing device clean. |
| 9644* | Right | Capsule present, white matter present |
| | Left | No white matter. Thin capsule, clear fluid/slightly red-tinged under envelope. |
| 9646* | Right | Thin capsule, no white matter. |
| | Left | Thin capsule, some white matter. |
| 8245 | Right | Incision appears well healed. Thin layer of film noted around pacing device. |
| | Left | Incision appears well healed. Bacterial envelope intact. Removed bacterial envelope, pacing device clean. |
| 8246 | Right | Incision appears well healed. Thin layer of film noted around pacing device. |
| | Left | Incision appears well healed. Bacterial envelope intact. Removed bacterial envelope, pacing device clean. |
| 9642* | Right | Capsule present, small amount of white matter at bottom of pocket. |
| | Left | Grossly swollen (skin) capsule present, large amount of white matter. |
| 9645* | Right | Capsule present, small white matter at bottom of pocket. |
| | Left | Grossly swollen (skin). Capsule present, large amount of white matter present. |
| 8244 | Right | Incision appears well healed. Moderate layer of film noted around pacing device. |
| | Left | Incision appears well healed. Bacterial envelope intact. Removed bacterial envelope, pacing device clean. |
| 8247 | Right | Incision appears well healed. Moderate layer of film noted around pacing device. |
| | Left | Incision appears well healed. Bacterial envelope intact. Removed bacterial envelope, pacing device clean. |

TABLE 16-continued

Macroscopic (Gross) Clinical Observations

| ANIMAL # | IMPLANT SIDE | MACROSCOPIC (GROSS) OBSERVATIONS |
|---|---|---|
| 8248 | Right | Incision appears well healed. Moderate layer of film noted around pacing device. |
| | Left | Incision appears well healed. Bacterial envelope intact. Removed bacterial envelope, pacing device clean. |
| 8251 | Right | Incision appears well healed. Thin layer of film noted around pacing device. |
| | Left | Incision appears well healed. Bacterial envelope intact. Removed bacterial envelope, pacing device clean. |

*Groups 1 and Group 2 were repeated per Amendment #2 (n = 4 animals)

Swabs and Tissue Samples: A summary of bacterial colonization from swabs is presented in Tables 17-20. Swabs from the pacing device implants (right side) in Group 3 and 4 and the repeat of Group 2 resulted in bacterial growth. Sonicant samples from the pacing device implants (right side) in Group 1 and 2 also resulted in bacterial growth.

Bacterial Identification: One colony from each of the positive samples from each implant was analyzed by Gram stain and API identification. Results are presented in Tables 17-20. Bacteria recovered were determined to be cocci and rods. Gram stain results indicated Gram positive (n=2 of 6) and Gram negative (n=2 of 6). Each colony obtained from the positive swabs was identified as *S. capitis* and *E. coli* by API analysis in Groups 3 and 4. All isolates recovered during the repeat of Groups 1 and 2 were identified to genus *Staphylococcus*.

TABLE 17

Summary of Microbiology Data of the Group Infected with *S. aureus*

| | | | INOCULUM CFU/ML | | | | BACTERIAL IDENTIFICATION* | |
|---|---|---|---|---|---|---|---|---|
| | | | | | | | | API ™ |
| ANIMAL # | IMPLANT | SIDE | TARGET | INITIAL | POST IMPLANT | SWAB | GRAM STAIN | *STAPHYLOCOCCUS* TEST |
| Group 1[1]: *S. aureus* 1 × 10$^7$ CFU/mL | | | | | | | | |
| 8320 | Pacemaker alone | Right | $1.0 \times 10^7$ | $5.8 \times 10^6$ | $5.5 \times 10^6$ | – | N/A | N/A |
| | Pacemaker with AIGIS$_{RX}$™ | Left | $10 \times 10^7$ | | | – | N/A | N/A |
| 8327 | Pacemaker alone | Right | $1.0 \times 10^7$ | $5.8 \times 10^6$ | $5.5 \times 10^6$ | – | N/A | N/A |
| | Pacemaker with AIGIS$_{RX}$™ | Left | $1.0 \times 10^7$ | | | – | N/A | N/A |
| Group 1[2]: *S. aureus* 1 × 10$^8$ CFU/mL | | | | | | | | |
| 9644 | Pacemaker alone | Right | $1.0 \times 10^8$ | $1.5 \times 10^9$ | $6.3 \times 10^9$ | –[3] | GPC | SA |
| | Pacemaker with AIGIS$_{Rx}$™ | Left | $1.0 \times 10^8$ | | | –[3] | N/A | N/A |
| 9646 | Pacemaker with AIGIS$_{Rx}$™ | Right | $1.0 \times 10^8$ | $1.5 \times 10^9$ | $6.3 \times 10^9$ | – | N/A | N/A |
| | Pacemaker alone | Left | $1.0 \times 10^8$ | | | – | N/A | N/A |

[1]Group 1 and Group 2 failed to develop infection in control or test article
[2]Group 1 and Group 2 was repeated.
[3]Isolates obtained from sonicant samples.
*All strain identifications achieved >95% certainty by API tests, unless otherwise noted.
GPC: Gram positive cocci
SA: *Staphylococcus aureus*
N/A: Not Applicable, no recovered bacteria
**Spores or spore-like structures

TABLE 18

Summary of Microbiology Data of the Group Infected with *S. epidermidis*

| ANIMAL # | IMPLANT | SIDE | INOCULUM CFU/ML TARGET | INITIAL | POST IMPLANT | SWAB | GRAM STAIN | BACTERIAL IDENTIFICATION* API™ *STAPHYLOCOCCUS* TEST |
|---|---|---|---|---|---|---|---|---|
| Group 2[1]: *S. epidermidis* $1 \times 10^{10}$ CFU/mL ||||||||||
| 8245 | Pacemaker alone | Right | $1.0 \times 10^{10}$ | $4.3 \times 10^{9}$ | $4.9 \times 10^{9}$ | − | N/A | N/A |
|  | Pacemaker with AIGIS$_{RX}$™ | Left | $1.0 \times 10^{10}$ |  |  | − | N/A | N/A |
| 8246 | Pacemaker alone | Right | $1.0 \times 10^{10}$ | $4.3 \times 10^{9}$ | $4.9 \times 10^{9}$ | − | N/A | N/A |
|  | Pacemaker with AIGIS$_{RX}$™ | Left | $1.0 \times 10^{10}$ |  |  | − | N/A | N/A |
| Group 2[2]: *S. epidermidis* $1 \times 10^{11}$ CFU/mL ||||||||||
| 9642 | Pacemaker with AIGIS$_{RX}$™ | Right | $1.0 \times 10^{11}$ | $6.0 \times 10^{10}$ | $4.8 \times 10^{10}$ | − | N/A | N/A |
|  | Pacemaker alone | Left | $1.0 \times 10^{11}$ |  |  | + | GPC | S |
| 9645 | Pacemaker alone | Right | $1.0 \times 10^{11}$ | $6.0 \times 10^{10}$ | $4.8 \times 10^{10}$ | + | GPC | S |
|  | Pacemaker with AIGIS$_{RX}$™ | Left | $1.0 \times 10^{11}$ |  |  | + | GPC | S |

[1]Group 1 and Group 2 failed to develop infection in control or test article
[2]Group 1 and Group 2 was repeated.
*All strain identifications achieved >95% certainty by API tests, unless otherwise noted.
GPC: Gram positive cocci
GNR: Gram negative rods
SA: *Staphylococcus aureus*
S: *Staphylococcus*
N/A: Not Applicable, no recovered bacteria

TABLE 19

Summary of Microbiology Data of the Groups Infected with *S. capitis* and *E. coli*

| ANIMAL # | IMPLANT | SIDE | INOCULUM CFU/ML TARGET | INITIAL | POST IMPLANT | SWAB | GRAM STAIN | BACTERIAL IDENTIFICATION* API™ *STAPHYLOCOCCUS* TEST |
|---|---|---|---|---|---|---|---|---|
| Group 3: *S. capitis* $1 \times 10^{10}$ CFU/mL ||||||||||
| 8244 | Pacemaker alone | Right | $1.0 \times 10^{10}$ | $1.3 \times 10^{10}$ | $1.2 \times 10^{10}$ | + | GPC | S. |
|  | Pacemaker with AIGIS$_{RX}$™ | Left | $1.0 \times 10^{10}$ |  |  | − | N/A | N/A |
| 8247 | Pacemaker alone | Right | $1.0 \times 10^{10}$ | $1.3 \times 10^{10}$ | $1.2 \times 10^{10}$ | + | GPC | *S. capitis* |
|  | Pacemaker with AIGIS$_{RX}$™ | Left | $1.0 \times 10^{10}$ |  |  | − | N/A | N/A |
| Group 4: *E. coli* $1 \times 10^{7}$ CFU/mL ||||||||||
| 8248 | Pacemaker alone | Right | $1.0 \times 10^{7}$ | $1.2 \times 10^{7}$ | $1.0 \times 10^{7}$ | + | GNR | *E. coli* |
|  | Pacemaker with AIGIS$_{RX}$™ | Left | $1.0 \times 10^{7}$ |  |  | − | N/A | N/A |
| 8251 | Pacemaker alone | Right | $1.0 \times 10^{7}$ | $1.2 \times 10^{7}$ | $1.0 \times 10^{7}$ | + | GNR** | *E. coli* |

TABLE 19-continued

Summary of Microbiology Data of the Groups Infected with *S. capitis* and *E. coli*

| ANIMAL # | IMPLANT | SIDE | INOCULUM CFU/ML | | | BACTERIAL IDENTIFICATION* | | |
|---|---|---|---|---|---|---|---|---|
| | | | TARGET | INITIAL | POST IMPLANT | SWAB | GRAM STAIN | API ™ *STAPHYLOCOCCUS* TEST |
| | Pacemaker with AIGIS$_{RX}$™ | Left | $1.0 \times 10^7$ | | | — | N/A | N/A |

*All strain identifications achieved >95% certainty by API tests, unless otherwise noted.
GPC: Gram positive cocci
GNR: Gram negative rods
S: *Staphylococcus*
N/A: Not Applicable, no recovered bacteria
**Spores or spore-like structure

TABLE 20

Summary of CFU Data by Group

| Animal # | Side | Sonicant 1 | | | | Sonicant 2 | | | | Sonicant 3 | | | |
|---|---|---|---|---|---|---|---|---|---|---|---|---|---|
| | | Dil | CFU/Plate | CFU/mL[1] | CFU/Sonicant[2] | Dil | CFU/Plate | CFU/mL[1] | CFU/Sonicant[2] | Dil | CFU/Plate | CFU/mL[1] | CFU/Sonicant[2] |
| Group 1[3]: *S. aureus* $1 \times 10^8$ CFU/mL | | | | | | | | | | | | | |
| 9644 | Right | Und | 0 | 0.00E+00 | 0.00E+00 | Und | 0 | 0.00E+00 | 0.00E+00 | Und | 185 | 9.25E+02 | 4.63E+04 |
| | | $10^{-1}$ | 0 | | | $10^{-1}$ | 0 | | | $10^{-1}$ | 20 | | |
| | | $10^{-2}$ | 0 | | | $10^{-2}$ | 0 | | | $10^{-2}$ | 3 | | |
| | | $10^{-3}$ | 0 | | | $10^{-3}$ | 0 | | | $10^{-3}$ | 0 | | |
| | Left | Un | 0 | 0.00E+00 | 0.00E+00 | Un | 0 | 0.00E+00 | 0.00E+00 | Un | 0 | 0.00E+00 | 0.00E+00 |
| | | $10^{-1}$ | 0 | | | $10^{-1}$ | 0 | | | $10^{-1}$ | 0 | | |
| | | $10^{-2}$ | 0 | | | $10^{-2}$ | 0 | | | $10^{-2}$ | 0 | | |
| | | $10^{-3}$ | 0 | | | $10^{-3}$ | 0 | | | $10^{-3}$ | 0 | | |
| Group 2[3]: *S. epidermidis* $1 \times 10^{11}$ CFU/mL | | | | | | | | | | | | | |
| 9645 | Right | Und | 11 | 5.50E+01 | 2.75E+03 | Und | 29 | 1.45E+02 | 7.25E+03 | Und | 39 | 1.95E+02 | 9.75E+03 |
| | | $10^{-1}$ | 8 | | | $10^{-1}$ | 4 | | | $10^{-1}$ | 4 | | |
| | | $10^{-2}$ | 1 | | | $10^{-2}$ | 0 | | | $10^{-2}$ | 0 | | |
| | | $10^{-3}$ | 0 | | | $10^{-3}$ | 0 | | | $10^{-3}$ | 0 | | |
| | Left | Und | 0 | 0.00E+00 | 0.00E+00 | Und | 0 | 0.00E+00 | 0.00E+00 | Und | 0 | 0.00E+00 | 0.00E+00 |
| | | $10^{-1}$ | 0 | | | $10^{-1}$ | 0 | | | $10^{-1}$ | 0 | | |
| | | $10^{-2}$ | 0 | | | $10^{-2}$ | 0 | | | $10^{-2}$ | 0 | | |
| | | $10^{-3}$ | 0 | | | $10^{-3}$ | 0 | | | $10^{-3}$ | 0 | | |

Figure 18:
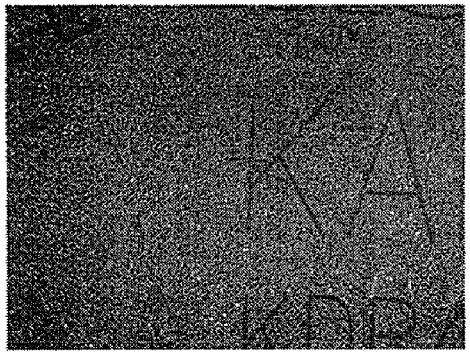
FIG. 18 depicts the confocal microscopy images of the implanted devices with and without the AIGIS$_{Rx}$™.
Figure 18:
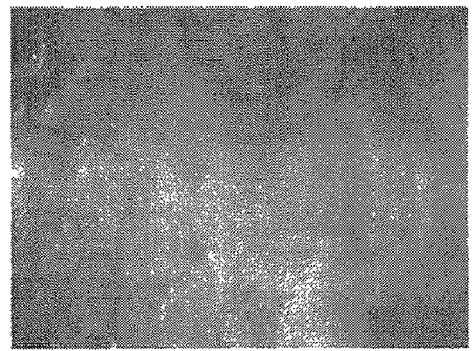
Figure 18:
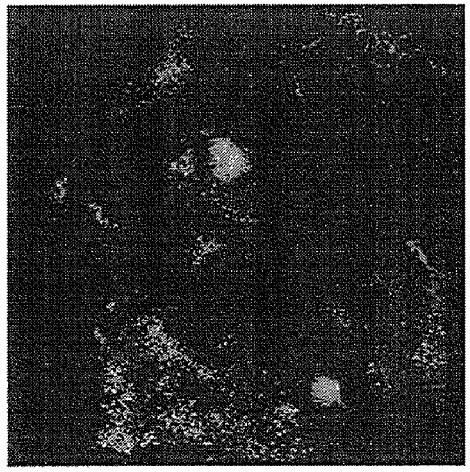
Figure 18:
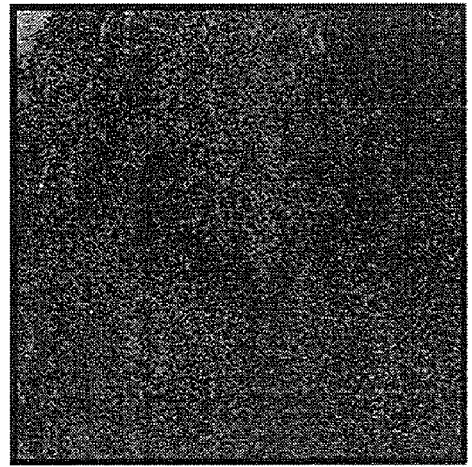
Figure 18:
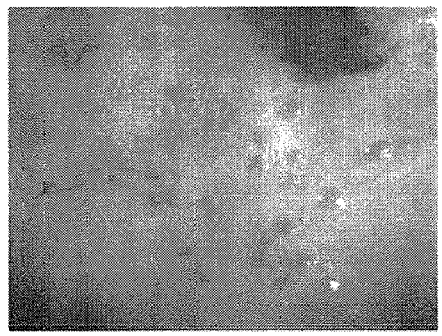
Figure 18:
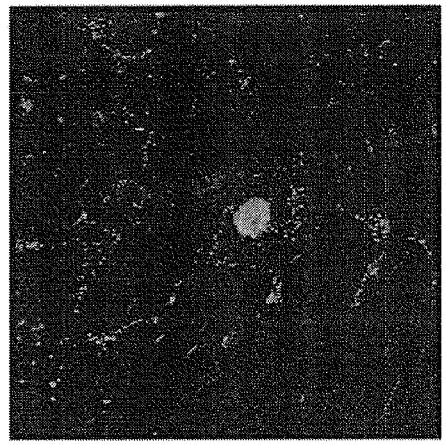
Figure 18:
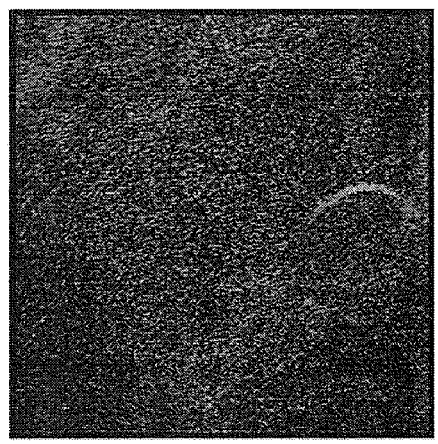
Figure 18:
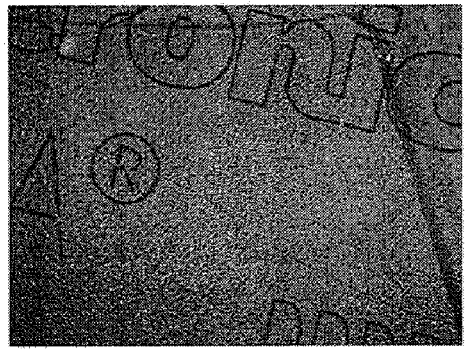
Figure 18:
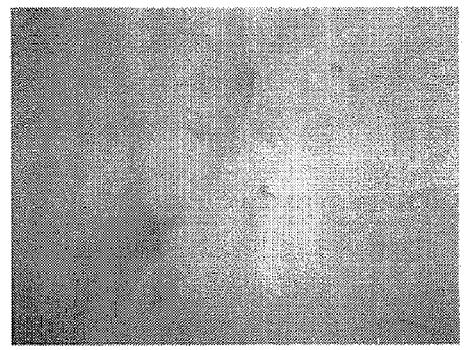
Figure 18:
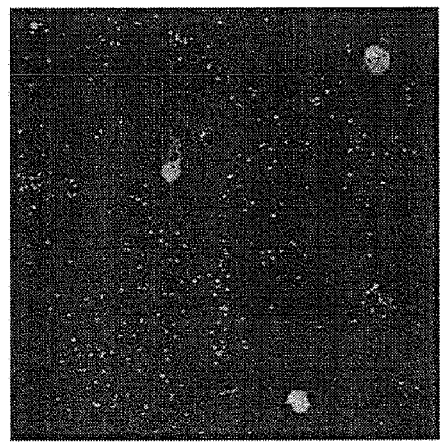
Figure 18:
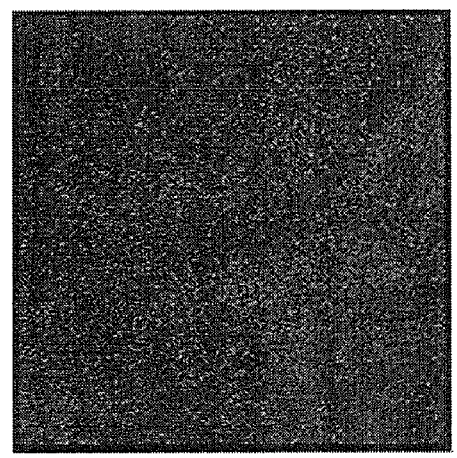
Figure 18:
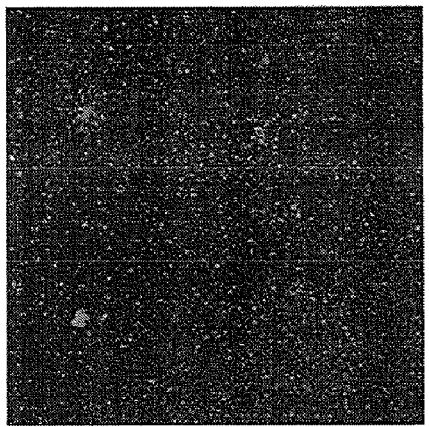
Figure 18:
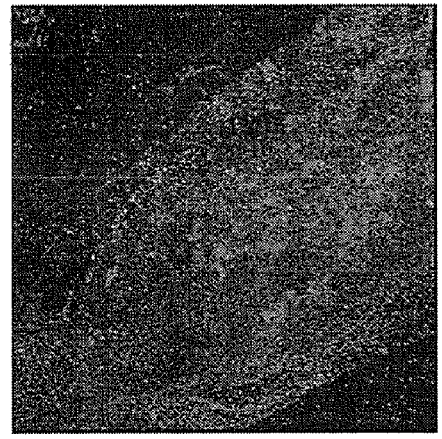

[1] 0.2 mL plated for a given dilution; (a) × 5 × 1.0E+(b); a = cfu/plate (between 30-300 if possible), b = reciprocal of the dilution of (a), an 5 is the reciprical of mL plated to get cfu/mL
[2] 50 mL sterile saline with 0.5% Tween 80 was added per sonicant; (cfu/mL) × total mL of sonicant (25) = total cfu recovered per sonicant.
[3] Group 1 and Group 2 was repeated per Amendment #2.
: number;
Dil: dilution;
CFU: colony forming units;
Und: undiluted Confocal Microscopy: The devices without the AIGIS$_{Rx}$™ envelope were observed to have bacterial infections, whereas the devices with the AIGIS$_{Rx}$™ envelope appeared to have minimal viable bacteria, see FIG. 18.

Figure 19:
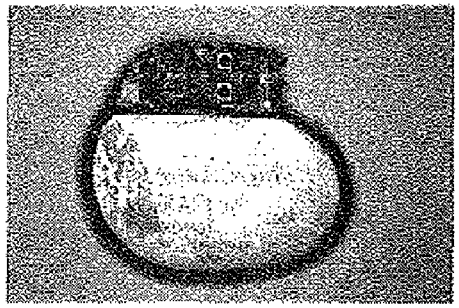
FIG. 19 depicts the gross scanning electron microscopy images of the implanted devices with and without the AIGIS$_{Rx}$™.
Figure 19:
Figure 19:
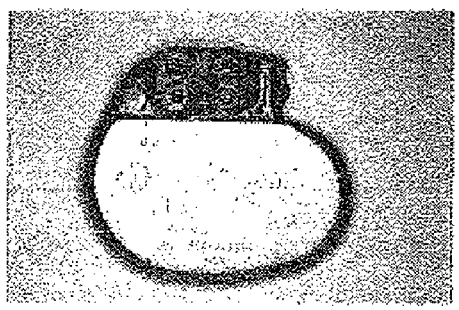
Figure 19:
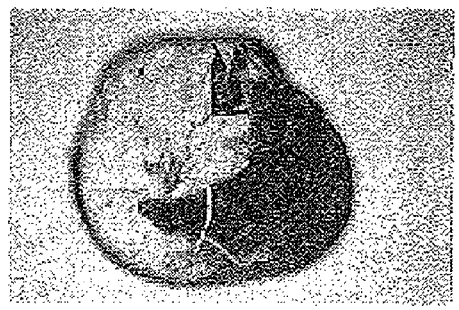
Figure 19:
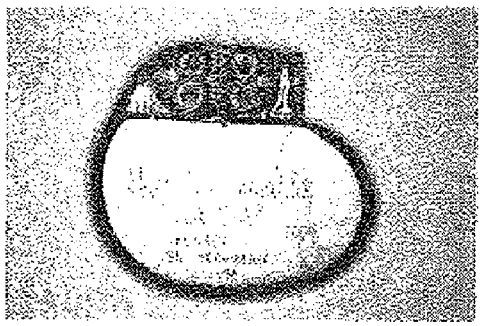
Figure 19:
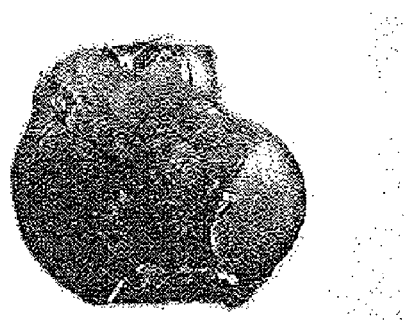
Figure 19:
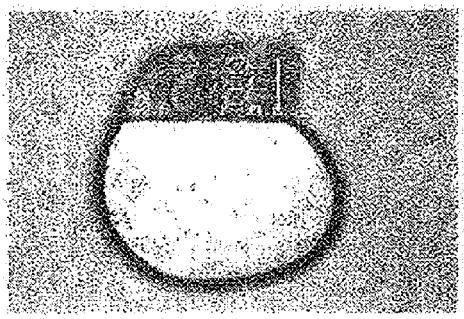
Figure 19:
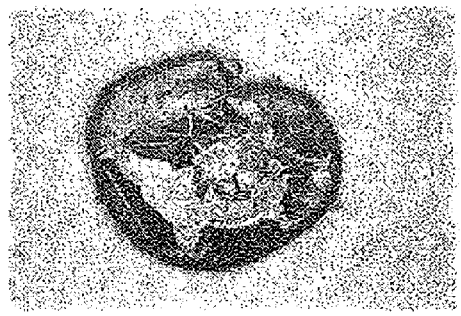
Figure 19:
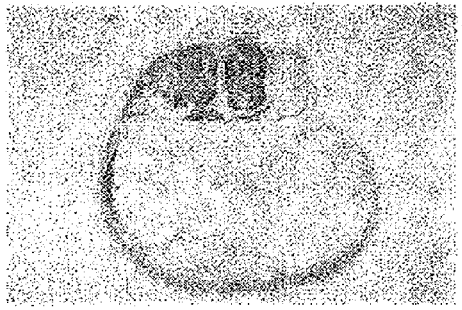
Figure 19:
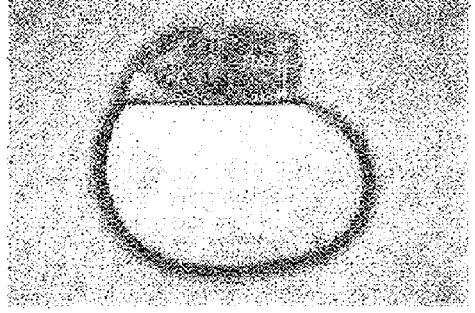
Figure 19:
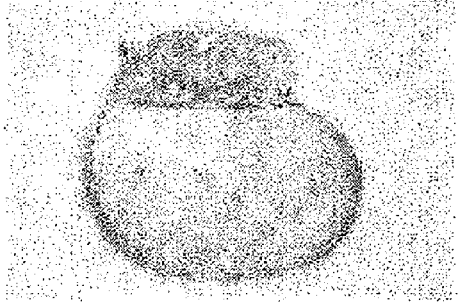
Figure 19:
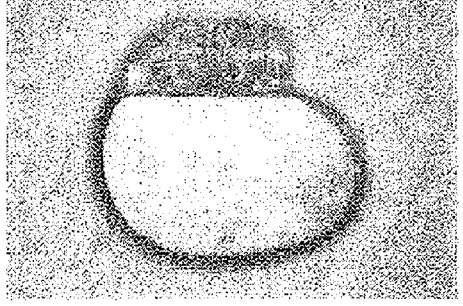
Figure 20:
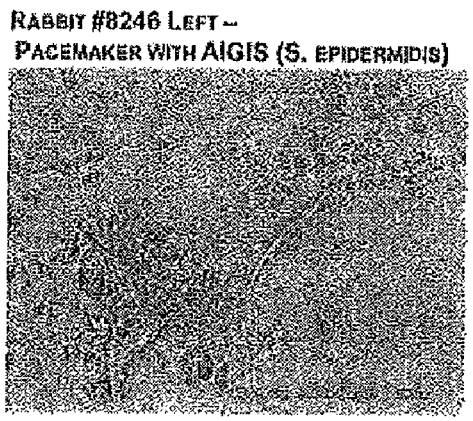
FIG. 20 depicts the scanning electron microscopy images of the implanted devices with and without the AIGIS$_{Rx}$™.
Figure 20:
Figure 20:
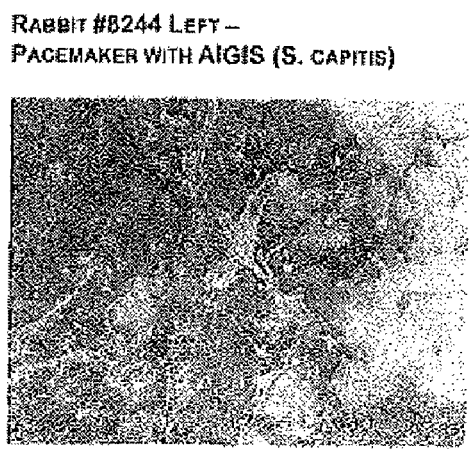
Figure 20:
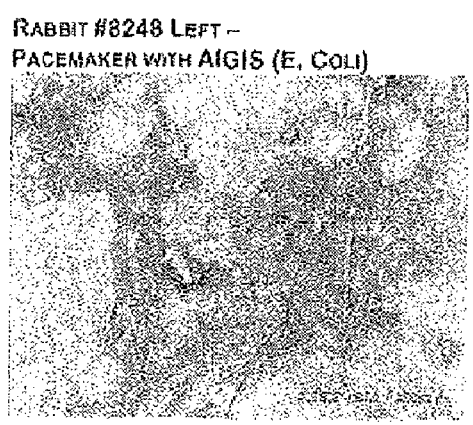
Figure 20:
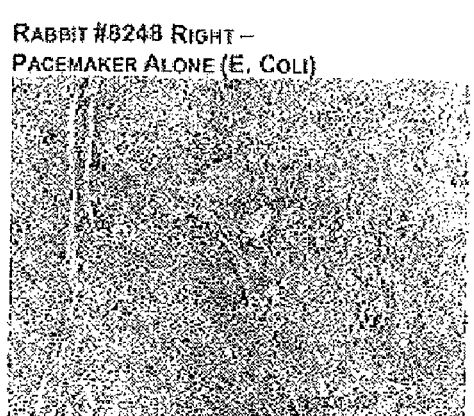
Figure 20:
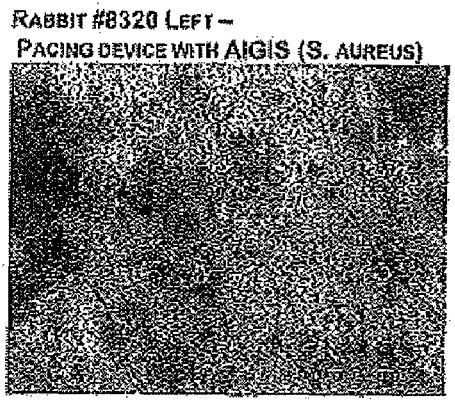
Figure 20:
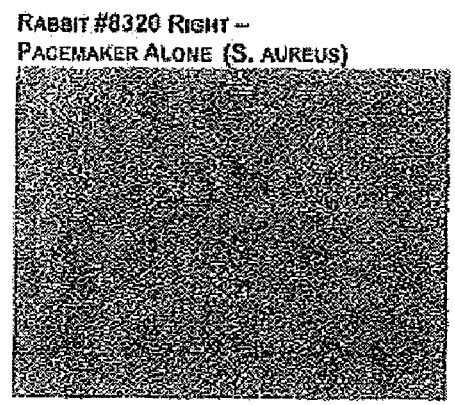
Figure 20:
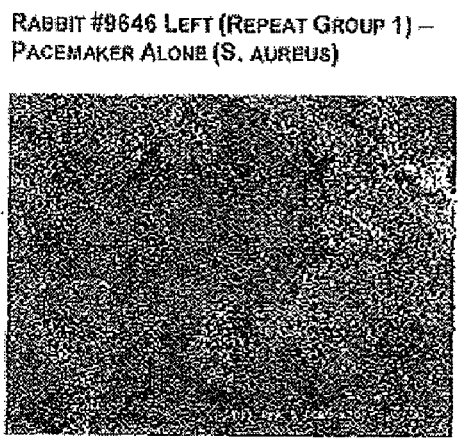
Figure 20:
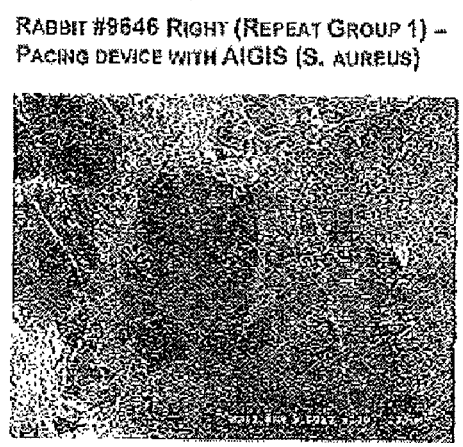
Figure 20:
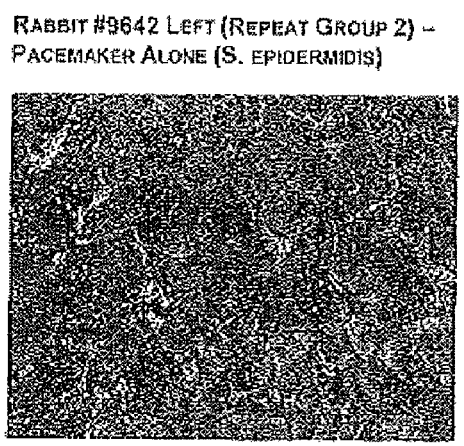
Figure 20:
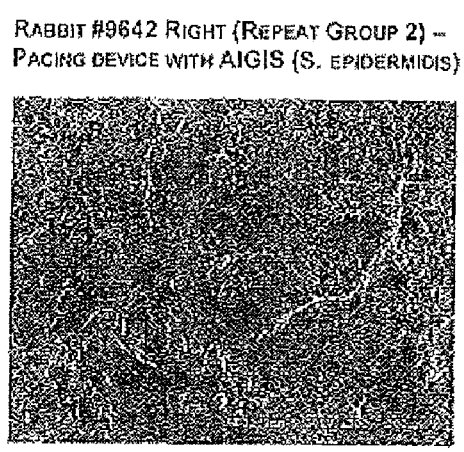

Scanning Electron Microscopy: The pacing devices with the AIGIS$_{Rx}$™ envelope did not appear to have any film surrounds the pacing device when removed from the envelope, see FIGS. 19 and 20.

REFERENCES

Hayes, B. B., Afshari, A., Millecchia, L., Willard, P. A., Povoski, S. P., Meade, B. J., 2000. Evaluation of percutaneous penetration of natural rubber latex proteins. Toxicol. Sci. 56, 262-270.

Khodorova, A. B., Strichartz, G. R., 2000. The addition of dilute epinephrine produces equieffectiveness of bupivacaine enantiomers for cutaneous analgesia in the rat. Anesth. Analg. 91, 410-416.

Kramer, C., Tawney, M., 1998. A fatal overdose of transdermally administered fentanyl. J. Am. Osteopath. Assoc. 98, 385-386.

Lau H, Patil N G, Lee F. Randomized clinical trial of postoperative subfascial infusion with bupivacaine following ambulatory open mesh repair of inguinal hernia. Dig Surg. 2003; 20(4):285-9.

LeBlanc K A, Bellanger D, Rhynes V K, Hausmann M Evaluation of a Continuous Infusion of 0.5% Marcaine via Elastomeric Pump for Postoperative Pain Management Following Open Inguinal Hernia Repair. J Am Coll Surg 2005; 200(2):198-202.

Morrow, T. J., Casey, K. L., 1983. Suppression of bulboreticular unit responses to noxious stimuli by analgesic mesencephalic stimulation. Somatosens. Res. 1, 151-168.

Sanchez B, Waxman K. Local anesthetic infusion pumps improve postoperative pain after inguinal hernia repair. The American Surgeon 2004; 70:1002-6.

Agostinho A, James G, Wazni O, Citron M, Wilkoff B D, Inhibition of *Staphylococcus aureus* Biofilms by a Novel Antibacterial Envelope for Use with Implantable Cardiac Devices, www.ctsjournal.com, vol. 2, issue 3, 193-198 (DOI: 10.1111/j.1752-8062.2009.00123.x)

NUMBERED REFERENCES

1. Hospital Infections Program, National Centre for Infectious Disease, CDC. Public health focus: surveillance, prevention, and control of nosocomial infections. MMWR Weekly, 1992; 41:783-7.
2. Perencevich E N, Sands K E, Cosgrove S E, et. al. Health and economic impact of surgical site infections diagnosed after hospital discharge. Emerging Infect Dis, 2003; 9:196-203.
3. Baddour L M, Bettmenn M A, Bolger A F, et. al. Nonvalvular cardiovascular device-related infections. Circulation, 2003; 108:2015-31.
4. Darouiche R O, Treatment of infections associated with surgical implants. NEJM, 2004; 350:1422-9.
5. Meakins J L, Prevention of Postoperative Infection. In ACS Surgery: Principals and Practice. American College of Surgeons, 2005.
6. Hambraeus A, Bengtsson S, Laurell G. Bacterial contamination in a modern operating suite, 2.effect of a zoning system on contamination of floors and other surfaces. J Hyg, 1978; 80:57-67.
7. Da Costa A, Kirkorian G, Cucherat M, et. al. Antibiotic prophylaxis for permanent pacemaker implantation: a meta-analysis. Circulation, 1998; 97:1796-1801.
8. Darouiche R O, Antimicrobial approaches for preventing infections associated with surgical implants. Clin Infect Dis 2003; 36:1284-9.
9. Pearson M L and Abrutyn E, Reducing the risk for catheter-related infections: a new strategy. Ann Intern Med, 1997; 127:304-6.
10. Donlon R M, Biofilms and device-associated infections. Emerg Infect Dis, 2001; 7:277-81.
11. Maki D G and Tambyah P A, Engineering out the risk of infection with urinary catheters. Emerg Infect Dis, 2001; 7:342-7.
12. Maki D G, Stolz S M, Wheeler S and Mermel L A. Prevention of central venous catheter-related blood stream infection by use of an antiseptic-impregnated catheter: a randomized, controlled trial. Ann Intern Med, 1997:127: 257-66.
13. Raad I, Darouiche R, Dupuis J, et. al., Central venous catheters coated with minocycline and rifampin for the prevention of catheter-related colonization and bloodstream infections: a randomized, double-blind trial. Ann Intern Med, 1997; 127:267-74.
14. Collin G R. Decreasing catheter colonization through the use of an antiseptic-impregnated catheter: a continuous quality improvement project. Chest, 1999; 115:1632-40.
15. Tennenberg S, Lieser M, McCurdy B, Boomer G, Howington E, Newman C, Wolf I. A prospective randomized trial of an antibiotic- and antiseptic-coated central venous catheter in the prevention of catheter-related infections. Arch Surg, 1997; 132:1348-51.
16. George S J, Vuddamalay P, Boscoe M J. Antiseptic-impregnated central venous catheters reduce the incidence of bacterial colonization and associated infection in immunocompromised transplant patients. Eur J Anaesthesiol, 1997; 14:428-31.
17. Segura M, Alvarez-Lerma F, Tellado J M, Jimenez-Ferreres J, Oms L, Rello J, Baro T, Sanchez R, Morera A, Mariscal D, Marrugat J, Sitges-Serra A. A clinical trial on the prevention of catheter-related sepsis using a new hub model. Ann Surg, 1996; 223:363-9.
18. Bach A, Schmidt H, Bottiger B, Schreiber B, Bohrer H, Motsch J, Martin E, Sonntag H G. Retention of antibacterial activity and bacterial colonization of antiseptic-bonded central venous catheters. J Antimicrob Chemother, 1996; 37:315-22.
19. Li H, Fairfax M R, Dubocq F, et. al. Antibacterial activity of antibiotic coated silicon grafts. J Urol, 1998; 160: 1910-3.
20. Darouiche R O, Mansouri N D, Raad H. Efficacy of antimicrobial-impregnated silicone sections from penile implants in preventing device colonization in an animal model. Urology, 2002; 59:303-7.
21. Darouiche R O, Meade R, Mansouri N D, Netscher D T. In vivo efficacy of antimicrobial-impregnated saline-filled silicone implants. Plast Reconstr Surg, 2002; 109:1352-7.
22. Chamis A L, Peterson G E, Cabell C H, et. al. *Staphylococcus aureus* bacteremia in patients with permanent pacemakers of implantable cardioverter-defibrillators. Circulation, 2001; 104:1029-33.

We claim:

1. A method of retarding biofilm formation on an implantable medical device which comprises: (a) enveloping or covering said device, in whole or in part, in a polymer pouch comprising a polymer-coated mesh pouch comprising one or more resorbable polymers comprising tyrosine-based polyarylates coated on the mesh and including one or more antimicrobial agents in amounts effective to retard biofilm formation; and (b) implanting said enveloped device in a subject.

2. The method of claim 1, wherein the polymer-coated mesh pouch comprises one or more resorbable polymers coated on the mesh.

3. The method of claim 1, wherein the one or more antimicrobial agents inhibit biofilm formation by one or more of *Staphylococcus aureus*, *Staphylococcus epidermidis*, *Escherichia coli* or *Acinetobacter baummanii*.

4. The method of claim 2, wherein the one or more antimicrobial agents inhibit biofilm formation by one or more of *Staphylococcus aureus*, *Staphylococcus epidermidis*, *Escherichia coli* or *Acinetobacter baummanii*.

5. The method of claim 1, wherein said implantable medical device is a cardiac rhythm management device (CRMD), a neurostimulator, a pulse generator, a drug pump or infusion device, a physiological monitoring device, or a textured or smooth breast implant.

6. The method of claim 5, wherein the implantable medical device is a CRMD selected from the group consisting of a pacemaker, a defibrillator, an implantable cardioverter defibrillator (ICD), and a cardiac resynchronization therapy defibrillator (CRT device).

7. The method of claim 1, wherein said coating comprises two or more layers, and at least one layer of the coating comprises at least one antimicrobial agent and at least one biocompatible polymer.

8. The method of claim 1, wherein the at least one antimicrobial agent comprises rifampin and minocycline.

9. The method of claim 2, wherein the at least one antimicrobial agent comprises rifampin and minocycline.

10. The method of claim 9, wherein the amounts of rifampin and minocycline in the coating ranges from about 60-90 µg/cm$^2$ for each of rifampin and minocycline.

11. The method of claim 10, wherein the coating comprises about 0.5-1.0 mg resorbable polymer/cm$^2$.

12. The method of claim 9, wherein the tyrosine-based polyarylates comprise a DTE-27.5% DT succinate polyarylate.

13. The method of claim 11, wherein the resorbable polymer is DTE-27.5% DT succinate polyarylate.

* * * * *